(12) United States Patent
Gomes et al.

(10) Patent No.: US 9,988,662 B2
(45) Date of Patent: Jun. 5, 2018

(54) USE OF LOW TEMPERATURE AND/OR LOW PH IN CELL CULTURE

(75) Inventors: Jose Manuel Gomes, Chelmsford, MA (US); Gregory Walter Hiller, Wakefield, MA (US)

(73) Assignee: Wyeth LLC, New York, NY (US)

( * ) Notice: Subject to any disclaimer, the term of this patent is extended or adjusted under 35 U.S.C. 154(b) by 1193 days.

(21) Appl. No.: 12/107,264

(22) Filed: Apr. 22, 2008

(65) Prior Publication Data

US 2008/0269132 A1   Oct. 30, 2008

Related U.S. Application Data

(60) Provisional application No. 60/913,382, filed on Apr. 23, 2007.

(51) Int. Cl.
| | | |
|---|---|---|
| *C12P 21/00* | (2006.01) | |
| *C12P 21/02* | (2006.01) | |
| *C07K 14/705* | (2006.01) | |

(52) U.S. Cl.
CPC ........ *C12P 21/02* (2013.01); *C07K 14/70578* (2013.01); *C12P 21/005* (2013.01); *C12N 2500/33* (2013.01); *C12N 2510/02* (2013.01)

(58) Field of Classification Search
CPC .. C07D 417/12; C07D 487/04; C07D 405/14; C07D 413/12; C07D 491/04; C07D 495/04; C07D 207/09; C07D 207/12; C07D 207/27; C07D 265/30; C07D 265/32; C07D 403/12; C07D 413/04; C07D 413/14; C07D 493/04; C07K 2317/41; C07K 16/32; C07K 2317/14; C07K 2319/30; C07K 16/00; C07K 16/241; C07K 2317/524; C07K 14/44; C07K 14/70503; C07K 14/70578; C07K 16/1027; C07K 16/18; C07K 16/2863; C07K 16/4291; C07K 2317/02; C12N 2510/02; C12N 5/0018; C12N 2500/20; C12N 2500/34; C12N 5/0037; C12N 2500/24; C12N 2500/25; C12N 2500/30; C12N 2500/32; C12N 2500/38; C12N 2500/50; C12N 2500/60; C12N 2500/74; C12N 2500/76; C12N 2500/90; C12N 2501/10; C12N 2501/33; C12N 2511/00; C12N 2500/33; C12P 21/005; C12P 21/02
See application file for complete search history.

(56) References Cited

U.S. PATENT DOCUMENTS

| | | | |
|---|---|---|---|
| 4,816,567 A | 3/1989 | Cabilly et al. | |
| 5,225,538 A | 7/1993 | Capon et al. | |
| 5,399,677 A | 3/1995 | Wolfman et al. | |
| 5,428,130 A | 6/1995 | Capon et al. | |
| 5,455,165 A | 10/1995 | Capon et al. | |
| 5,514,582 A | 5/1996 | Capon et al. | |
| 5,516,964 A | 5/1996 | Umansky et al. | |
| 5,610,033 A | 3/1997 | Rasmussen et al. | |
| 5,633,162 A | 5/1997 | Keen et al. | |
| 5,705,364 A | 1/1998 | Etcheverry et al. | |
| 5,710,023 A | 1/1998 | Collins et al. | |
| 5,714,147 A | 2/1998 | Capon et al. | |
| 5,976,833 A | 11/1999 | Furukawa et al. | |
| 6,136,310 A | 10/2000 | Hanna et al. | |
| 6,924,124 B1 | 8/2005 | Singh | |
| 2003/0064630 A1 | 4/2003 | Pocrass | |
| 2003/0118592 A1 | 6/2003 | Ledbetter et al. | |
| 2003/0133939 A1 | 7/2003 | Ledbetter et al. | |
| 2003/0175951 A1 | 9/2003 | Behrendt et al. | |
| 2004/0058445 A1 | 3/2004 | Ledbetter et al. | |
| 2004/0058800 A1 | 3/2004 | Hasuyama et al. | |
| 2004/0077086 A1 | 4/2004 | Reiter et al. | |
| 2004/0265964 A1 | 12/2004 | Allen et al. | |
| 2005/0136049 A1 | 6/2005 | Ledbetter et al. | |
| 2005/0175614 A1 | 8/2005 | Ledbetter et al. | |
| 2005/0180970 A1 | 8/2005 | Ledbetter et al. | |
| 2005/0186216 A1 | 8/2005 | Ledbetter et al. | |
| 2005/0202012 A1 | 9/2005 | Ledbetter et al. | |
| 2005/0202023 A1 | 9/2005 | Ledbetter et al. | |
| 2005/0202028 A1 | 9/2005 | Ledbetter et al. | |
| 2005/0202534 A1 | 9/2005 | Ledbetter et al. | |
| 2005/0238646 A1 | 10/2005 | Ledbetter et al. | |
| 2006/0121568 A1 | 6/2006 | Drapeau et al. | |
| 2007/0002159 A1 | 1/2007 | Olsen et al. | |
| 2009/0042253 A1 | 2/2009 | Hiller | |

FOREIGN PATENT DOCUMENTS

| | | |
|---|---|---|
| EP | 417014 | 3/1991 |
| EP | 417563 | 3/1991 |
| EP | 0433225 | 6/1991 |

(Continued)

OTHER PUBLICATIONS

Yoon Sung Kwan et al (2005) Biotechnology and Bioengineering 89(3):345-356, "*Effect of Culture pH on Erythropoietin Production by Chinese Hamster Ovary Cells Grown in Suspension at 32.5 and 37.0° C.*"
Borys M C et al (1993) Bio/technology 11(6):720-724, "*Culture pH affects expression rates and glycosylation of recombinant mouse placental lactogen proteins by Chinese hamster ovary (CHO) cells*".
Bird et al (1988) Science 242: 423-426, "*Single-Chain Antigen-Binding Proteins*".
Chuppa et al. *Fermentor Temperature as a Tool for Control of High-Density Perfusion Cultures of Mammalian Cells.* Biotechnology & Bioengineering. vol. 55(2) (pp. 328-338), 1997.
Trummer et al. *Process parameter shifting: Part I. Effect of DOT, pH, and temperature on the performance of Epo-Fc expressing CHO cells cultivated in controlled batch bioreactors.* Biotechnology & Bioengineering. vol. 94(6) (pp. 1033-1044), 2006.
International Search Report, dated Jul. 7, 2008.
U.S. Appl. No. 60/954,922, filed Aug. 9, 2007, Hiller.

(Continued)

*Primary Examiner* — Deborah K Ware
(74) *Attorney, Agent, or Firm* — Stephen E. Moyer

(57) ABSTRACT

The present disclosure provides a method of reducing protein misfolding and aggregation in the cell culture by growing the cell culture at a reduced temperature and/or reduced pH. As a result, the quality of the protein produced in the cell culture is greatly improved. Thus, the present disclosure facilitates improvements in the efficacy of therapeutic proteins produced in cell culture.

11 Claims, 45 Drawing Sheets

(56) References Cited

FOREIGN PATENT DOCUMENTS

| WO | WO 9404678 | 8/1993 |
|---|---|---|
| WO | WO 00/36092 | 6/2000 |
| WO | WO 2003064630 A2 | 8/2003 |
| WO | WO 03/083066 | 10/2003 |
| WO | WO 2004/008100 | 1/2004 |
| WO | WO 2004058800 A2 | 7/2004 |
| WO | WO 2006/026447 | 3/2006 |

OTHER PUBLICATIONS

Bork et al (2007) FEBS Letters 581(22):4195-4198, "*Enhanced Sialylation of EPO by Overexpression of UDP-GlcNAc2-epimerase/ManAc Kinase of Containing a Sialuria Mutation in CHO Cells*".
Clackson et al (1991) Nature 352: 624-628, "*Making antibody fragments using phage display libraries*".
Dooley et al (2006) PNAS USA 103:1846-1851, "*First molecular and biochemical analysis of in vivo affinity maturation in an ectothermic vertebrate*".
Helenius et al (2001) Science 291: 2364-2369, "*Intracellular Functions of N-Linked Glycans*".
Huston et al (1988) PNAS USA 85:5879-5883, "*Protein engineering of antibody binding sites: Recovery of specific activity in an anti-digoxin single-chain Fv analogue produced in Escherichia coli*".
Jefferis, Royston (2005) Biotechnology Prog. 21: 11-16, "*Glycosylation of Recombinant Antibody Therapeutics*".
Kohler et al (1975) Nature 256:495-499, "*Continuous cultures of fused cells secreting antibody of predefined specificity*".
Kohno et al (1990) Meth Enzymol. 185:187-195, "*Refolding of Recombinant Proteins*".
Kostelny et al (1992) J. Immunol 148:1547-1553, "*Formation of a Bispecific Antibody by the use of Leucine Zippers*".
Marks et al (1991) J. Mol. Biol 222:581-597, "*By-passing Immunization Human Antibodies from V gene Libraries Displayed on Phage*".
Naismith and Sprang (1996) J. Inflamm 47:1-7, "*Tumor Necrosis Factor Receptor Superfamily*".
Parodi, Armando (2000) Biochem J. 348:1-13, "*Role of N-oligosaccharide endoplasmic reticulum processing reaction in glycoprotein folding and degradation*".
Parodi, Armando (2000) Annu Rev. Biochem 69:69-93, "*Protein Glucosylation and Its Role in Protein Folding*".
Songsivilai & Lachmann (1990) Clin Exp Immunol 79:315-321, "*Bispecific antibody: a tool for diagnosis and treatment of disease*".
Solá et al (2007) Cell. Mol. Life Science 64(16):2133-2152, "*Modulation of Protein Biophysical Properties by Chemical Glycosylation: Biochemical Insights and Biomedical Implications*".
Solá and Griebenow (2006) FEBS Letters 580(6):1685-1690, "*Chemical Glycosylation: New Insights on the Interalation Between Protein Structural Mobility, Thermodynamic Stability, and Catalysis*".
Mather et al (1999) Encyclopedia of Bioprocess Technology: Fermentation Biocatalysis and Bioseparation vol. 2: 777-785.
Schatz, S. et al., "*Higher Expression of Fab Antibody Fragments in a CHU Cell Line at Reduced Temperature*," Biotechnology and Bioengineering 84(4):433-438, 2003.
Trummer, T., et al., 2006, "Process Parameter Shifting: Part II. Biphasic Cultivation—A Tool for Enhancing the Volumetric Productivity of Batch Processes Using Epo-Fc Expressing CHO Cells," Biotechnology and Bioengineering, vol. 94/6:1045-1052.
Zanghi, J.A. et al., "Bicarbonate concentration and osmolality are key determinants in the inhibition of CHO cell polysialyation under elevated pCO(2) or pH", Biotechnology and Bioengineering, 1999, vol. 65 No. 2: 182-191.
Rognoni, F., et al., Influence of osmolarity and pH increase to achieve a reduction of monoclonal antibodies aggregates in a production process, Cytotechnology 29: 11-25, 1999.

USE OF LOW TEMPERATURE AND/OR LOW PH IN CELL CULTURE

This application claims the benefit of U.S. Provisional Application Ser. No. 60/913,382, filed Apr. 23, 2007, which is incorporated herein by reference in its entirety.

BACKGROUND OF THE INVENTION

Field of the Invention

The present invention provides methods of improving protein production by cultured cells, especially mammalian cells. Specifically, the present invention relates to methods of preparing a protein product(s), e.g., a glycoprotein product(s), wherein the protein product characteristics are controlled by manipulating the cell culture environment. The invention also relates to methods of improving the therapeutic efficacy and/or immunogenicity of the protein product(s), e.g., the glycoprotein product(s), produced in mammalian cells, e.g., by manipulating protein glycosylation and decreasing protein aggregation and misfolding, by reducing the temperature and/or the pH of the cell culture.

Related Background Art

A large proportion of biotechnology products, whether commercially available or in development, are protein therapeutics. There is a large and increasing demand for production of proteins in animal cell cultures and for improved methods related to such production. Such improved methods are needed because the cellular machinery of an animal cell is generally required to produce many forms of protein therapeutics, such as posttranslationally modified proteins, particularly glycosylated proteins.

A common problem encountered in large-scale therapeutic protein production methods is that a significant portion of protein product is produced in either misfolded or aggregated form, i.e., in high molecular weight aggregate ("HMWA") form. For instance, recombinant overexpression of polypeptides in cells may overload the endoplasmic reticulum (ER) machinery, allowing an increased number of misfolded and/or aggregated proteins to evade degradative pathways and to exit the ER. Thus, current protein production methods may result in a large proportion of product which is aggregated, nonfunctional, and thus, unusable as produced. The presence of misfolded and/or aggregated protein is undesirable because it may lead to adverse events upon administration, including but not limited to, a potential for immunogenicity upon administration (e.g., complement activation or anaphylaxis). Thus, excessive therapeutic protein misfolding and/or aggregation may lead to failure in, e.g., clinical trials. Therefore, there is a need in the art for new methods of limiting or reducing protein misfolding and/or aggregation.

Protein glycosylation is a common posttranslational modification process by which complex sugar moieties are added onto a protein through the actions of a series of specialized enzymes—glycotransferases and glycosidases—in the ER. This process can control proper folding of the newly synthesized polypeptides such that only the correctly folded polypeptides exit the ER, whereas the misfolded proteins are degraded. Patterns of protein glycosylation affect protein targeting, structure, thermodynamic stability, and enzymatic activity (see, e.g., Solá et al. (2007) *Cell. Mol. Life Sci.* 64:2133-52; Sola and Griebenow (2006) *FEBS Lett.* 580:1685-90). For instance, N-glycan sialylation is associated with an increase in the lifetime of glycoproteins because such glycoproteins are not recognized by asialoglycoprotein receptors, which target nonsialylated proteins for degradation (see, e.g., Bork et al. (2007) *FEBS Letters* 581:4195-98). Thus, alterations in protein glycosylation may affect the quality and efficacy of the product.

Moreover, aberrant protein glycosylation may result in immunogenicity of the final therapeutic protein product. Proteins produced under nonnatural, suboptimal conditions can acquire sugars and sugar patterns not found naturally on human proteins, and thus result in immunogenic reaction in the subject (Jefferis (2006) *Biotechnol. Prog.* 21:11-16). Such nonnatural glycosylations are especially prevalent in protein therapeutics, such as antibody therapeutics or Fc-fusion protein therapeutics, e.g., soluble receptor Fc-fusion protein therapeutics.

For these reasons, the FDA requires that glycoform profiles of therapeutic proteins be maintained within strict limits. Thus, there is a need in the pharmaceutical industry for a method of therapeutic protein production in the cell culture that enables control of the level of protein glycosylation.

SUMMARY OF THE INVENTION

Thus, the invention is a method of producing a protein in a cell culture comprising at least one of: (a) growing cells in the cell culture at a reduced temperature; and (b) growing cells in the cell culture at a reduced pH; so that production of misfolded proteins and/or aggregated proteins is reduced. In embodiments, cells are grown in the cell culture at a reduced temperature and at a reduced pH.

In preferred embodiments, the invention is directed to modifying pH and temperature parameters to reduce production of misfolded and/or aggregated proteins in mammalian cell culture, and especially Chinese Hamster Ovary ("CHO") cell culture. In preferred embodiments the cell culture produces a protein (the "produced protein") that is a soluble receptor, such as, without limitation TNFR-Fc or sIL-13R proteins. In these preferred embodiments, the reduced temperature may be in a range of 27.0° C. to less than 30.0° C. In still other preferred embodiment, the reduced pH is in a range of 6.80 to less than 7.00. A combination of pH and temperature in the aforesaid ranges may also be used.

In another aspect, the invention is a method of producing a protein in a cell culture, wherein the level of protein glycosylation of the produced protein is controlled by modifying the temperature and/or the pH of the cell culture. Thus, the level of glycosylation, such as, without limitation, N-glycan sialylation, may be increased by increasing temperature and/or pH, or decreased by decreasing temperature and/or pH.

In another aspect, the invention is a method of producing a therapeutic protein controlling the parameters described above. In still another aspect, the invention is a pharmaceutical composition comprising a therapeutic protein made by such method and a pharmaceutically acceptable carrier.

BRIEF DESCRIPTION OF THE DRAWINGS

FIG. 4A depicts cell-specific productivities, represented by cumulative average Qp (X-axis; Cum. Avg. Qp [normalized mg/$e^9$ cells/day]), normalized to average harvest day cumulative average Qp, of the cell culture of CHO cells transfected with TNFR-Fc grown either at 27.0° C. [♦], 28.0° C. [▲], 29.0° C. [■], or 30.0° C. [○] over time (X-axis; culture time [d]); while

Figure 5A:
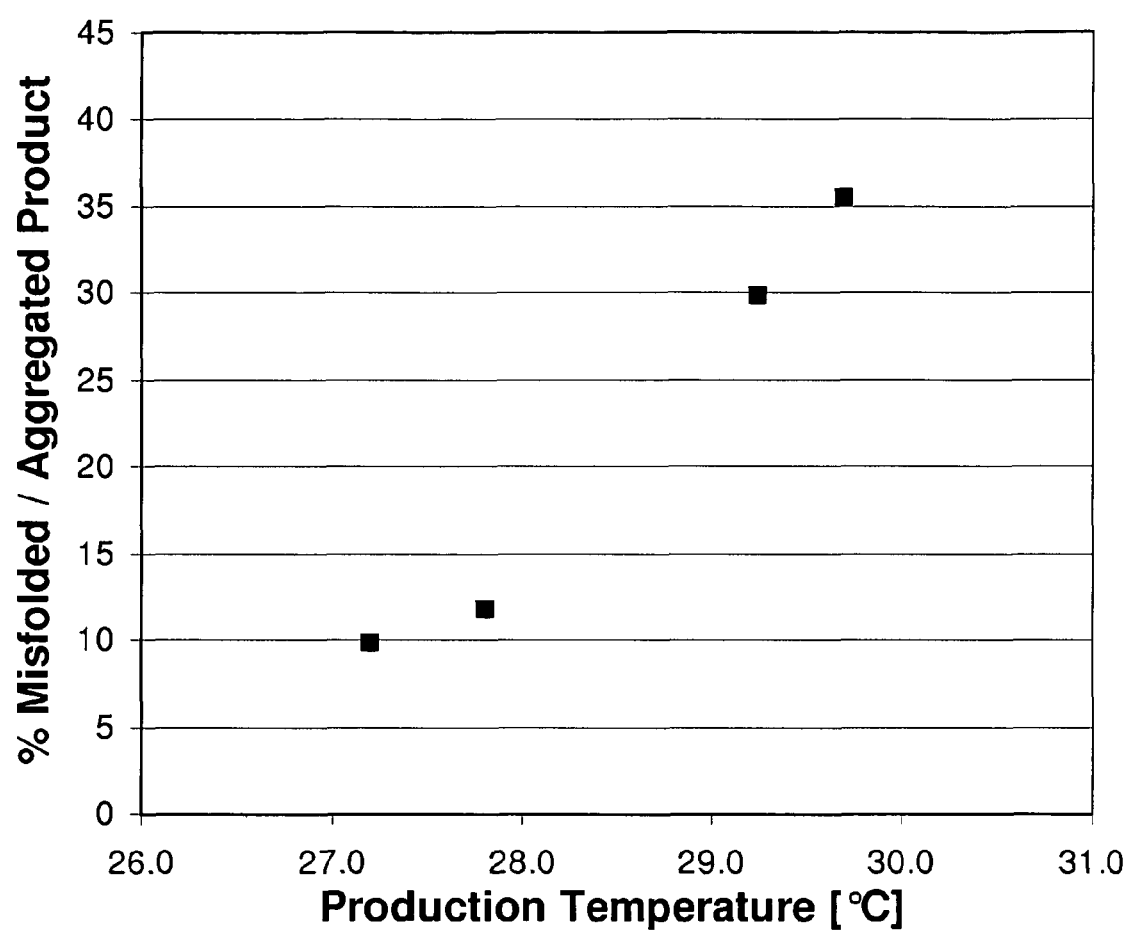
Figure 5B:
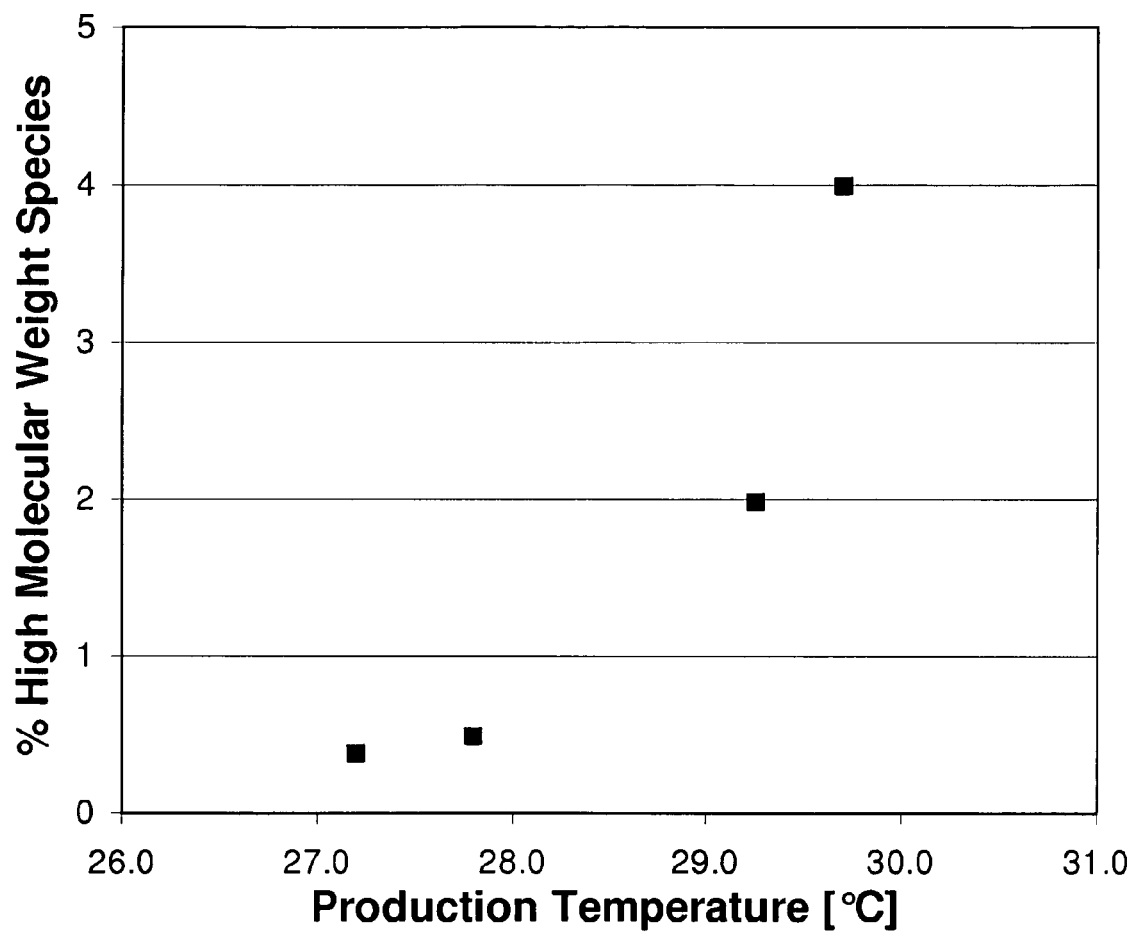

The effect of varying production temperatures (X-axis; [° C.]) in the cell culture of CHO cells transfected with TNFR-Fc on the production of misfolded and/or aggregated TNFR-Fc (Y-axis; % misfolded/aggregated product) is demonstrated in FIG. 5A; while the effect of temperatures on the production of HMWA (Y-axis; % high molecular weight species) is demonstrated in FIG. 5B.

Figure 6A:
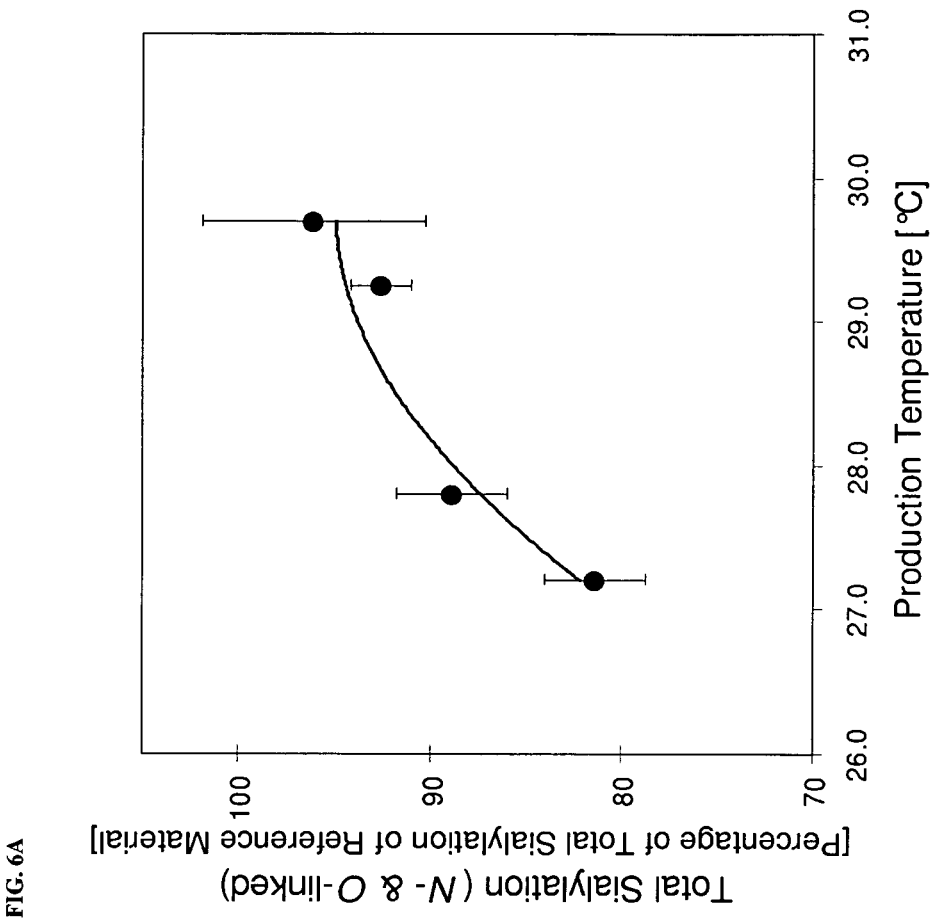
Figure 6B:
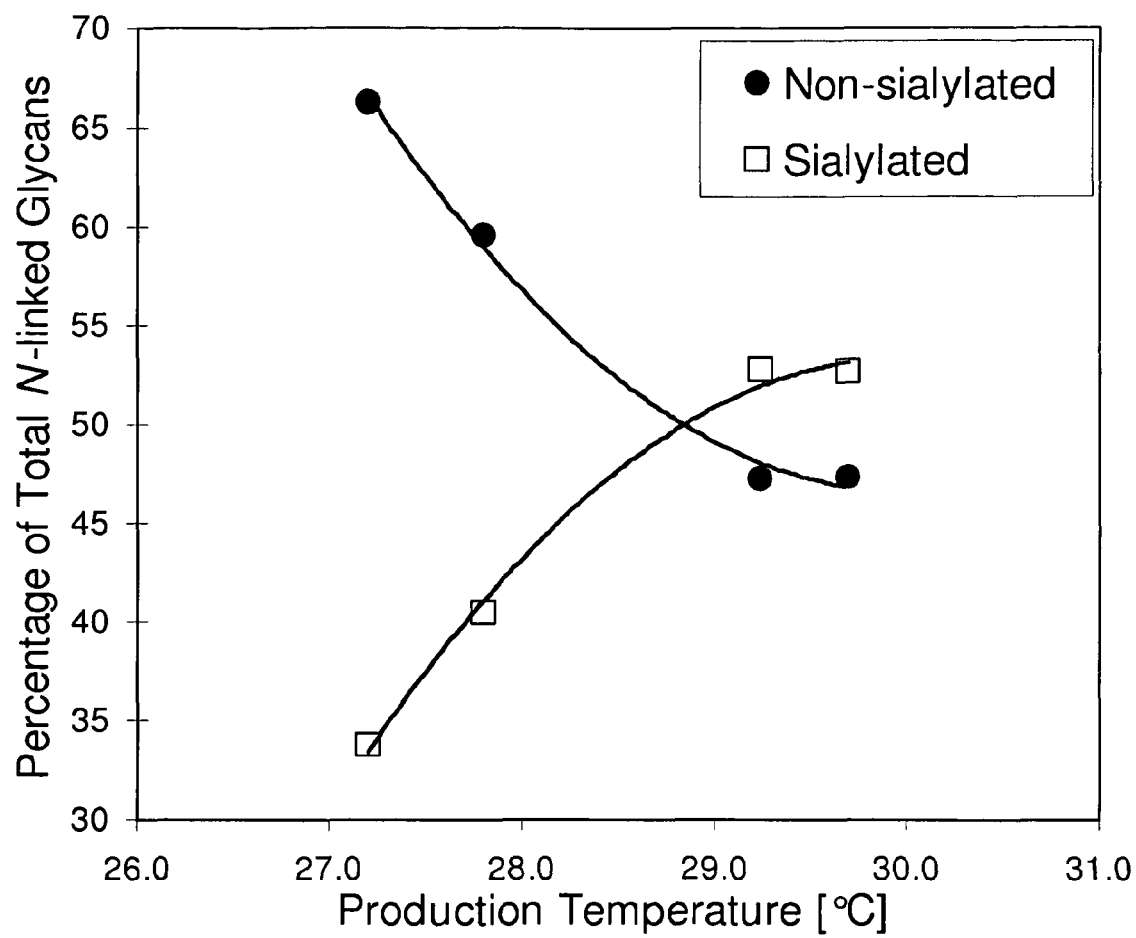

The effect of varying production temperatures (X-axis; temperature [° C.]) in the cell culture of CHO cells transfected with TNFR-Fc on the percentage of total sialylation (N- and O-linked sialylation) of TNFR-Fc (Y-axis; percentage of total sialylation of reference material) is demonstrated in FIG. 6A. The reference material used was a specific aliquot of TNFR-Fc with known and preferable glycosylation pattern to which the assay results may be compared. FIG. 6B demonstrates the effect of varying production temperatures (X-axis; temperature [° C.]) in the cell culture of the same cells on the percentage of total sialylated (□) or non-sialylated (●) N-linked glycans (Y-axis; Percentage of Total N-linked Glycans).

Figure 7:
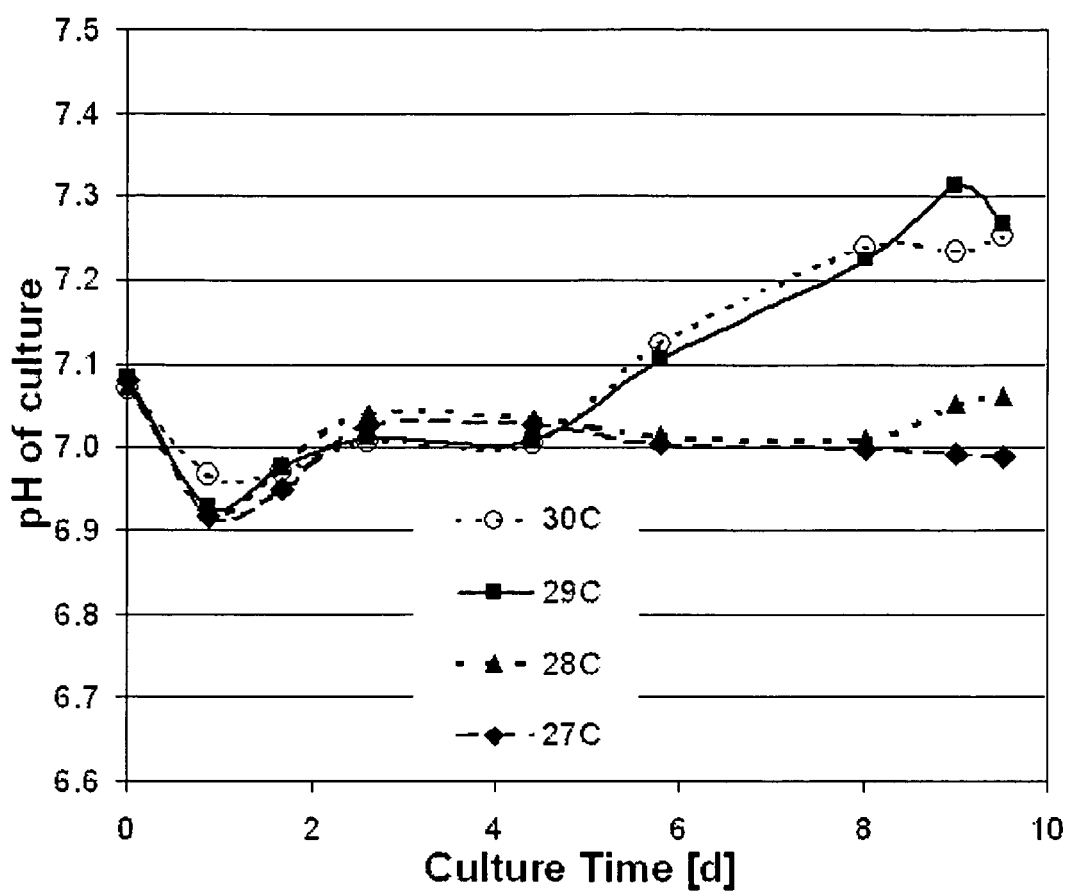

FIG. 7 demonstrates the effect of growing cells at different temperatures (27.0° C. [♦], 28.0° C. [▲], 29.0° C. [■], or 30.0° C. [○]) on the pH of the CHO cell culture (Y-axis) over time (X-axis; culture time [d]).

Figure 8A:
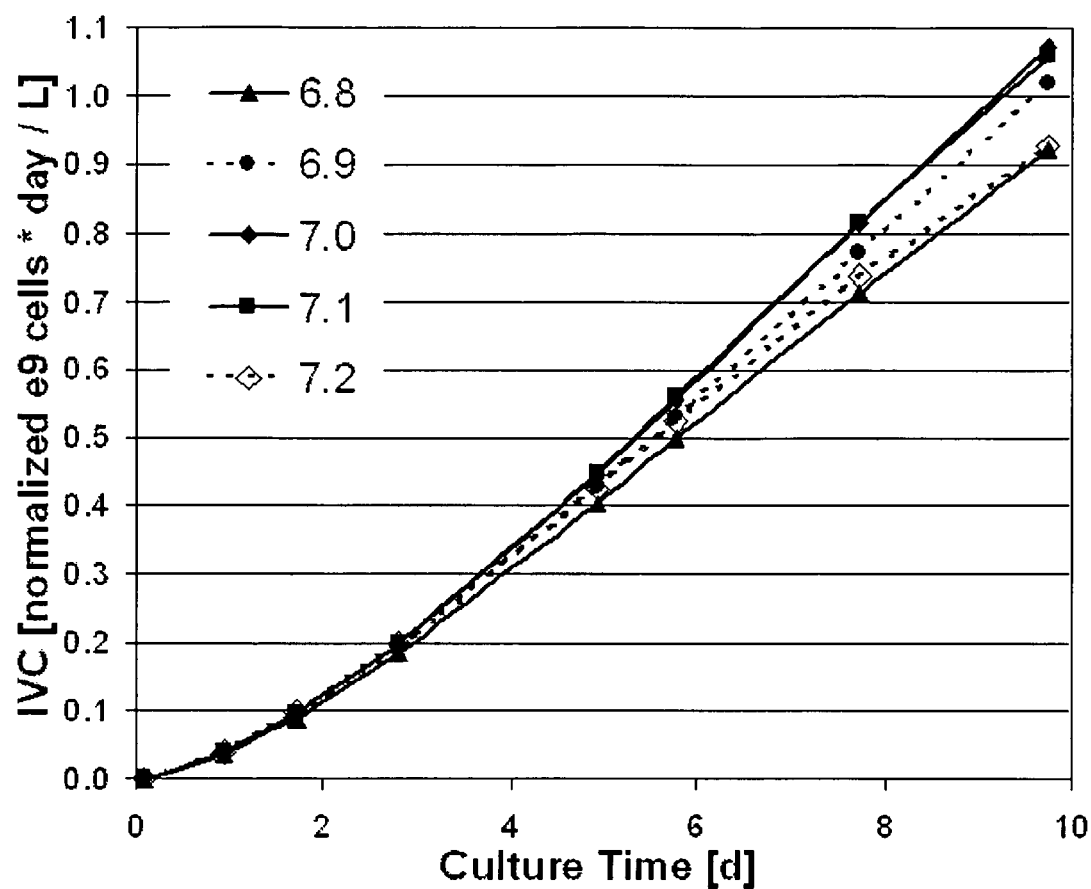
Figure 8B:
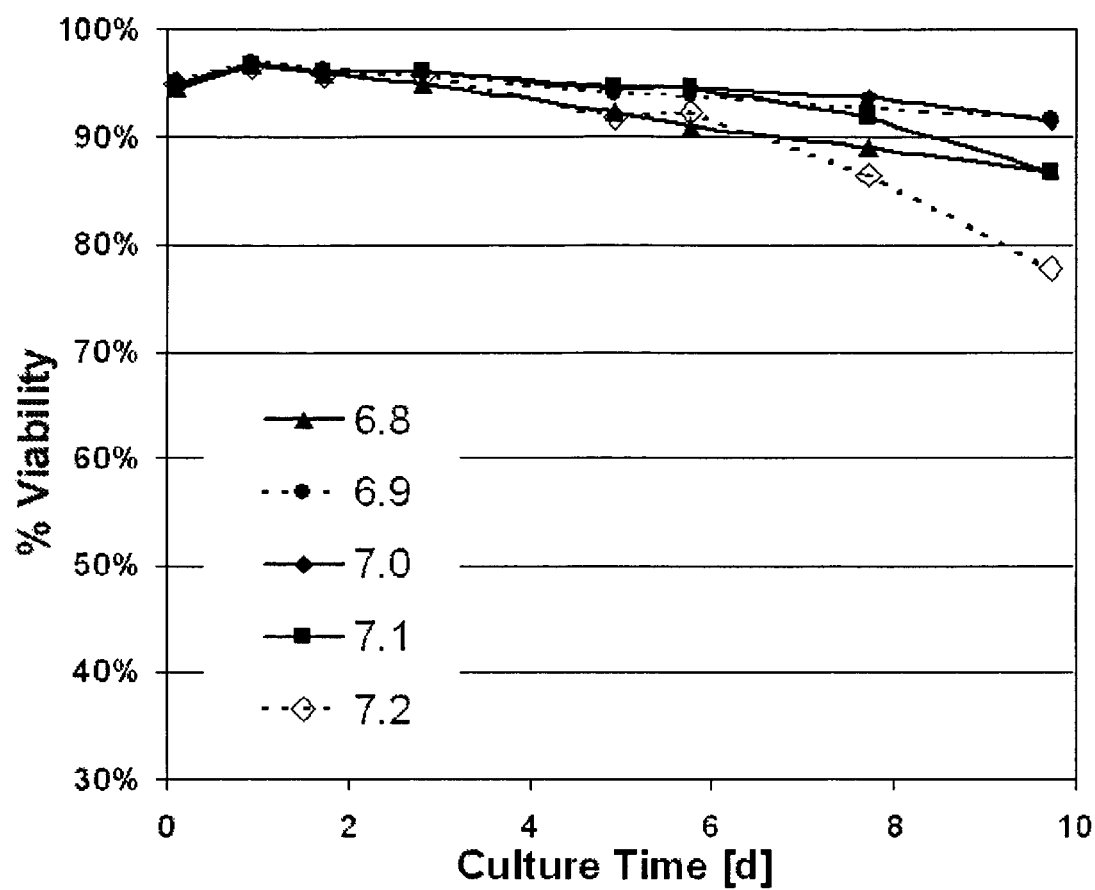

FIG. 8A represents integrated viable cell numbers (Y-axis; IVC [normalized $e^9$ cells*day/L]), normalized to average harvest day IVC, of the CHO cells transfected with TNFR-Fc grown at pH set point of either 7.20 [◊], 7.10 [■], 7.00 [♦], 6.90 [●], or 6.80 [▲] over time (X-axis; culture time [d]); while FIG. 8B represents cell viability (Y-axis) of the same cells over time (X-axis; culture time [d]).

Figure 9A:
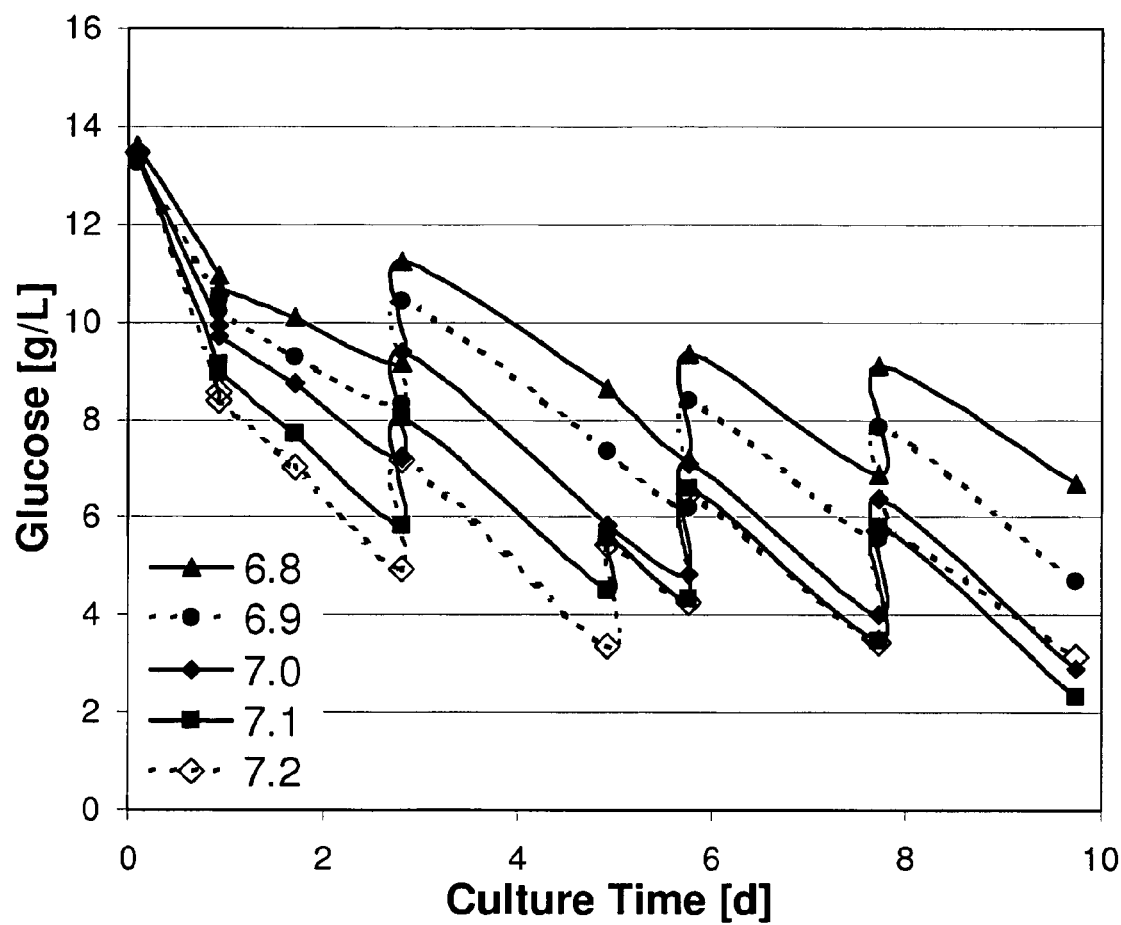
Figure 9B:
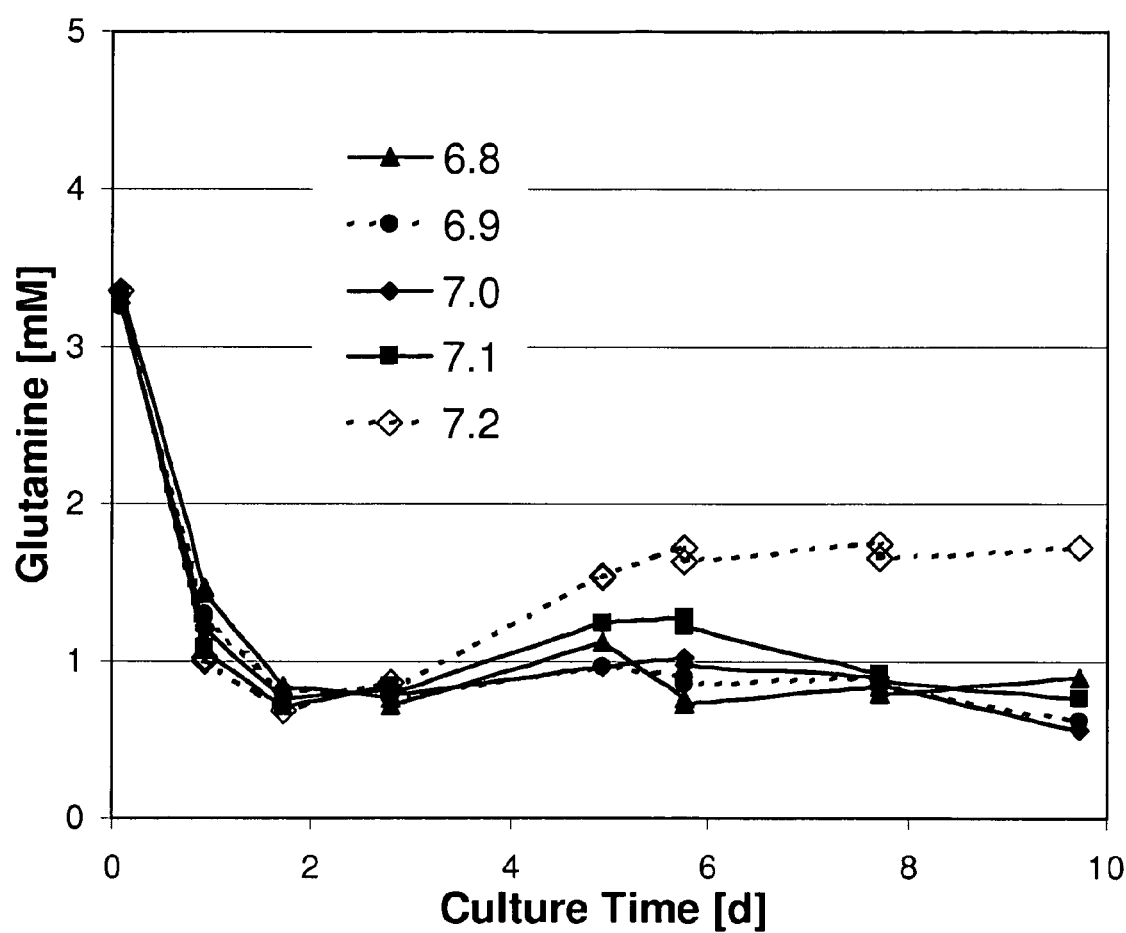

FIG. 9A represents glucose profile (Y-axis; glucose [g/L]) of the cell culture of CHO cells transfected with TNFR-Fc, grown at either pH set point of either 7.20 [◊], 7.10 [■], 7.00 [♦], 6.90 [●], or 6.80 [▲] over time (X-axis; culture time [d]); while FIG. 9B represents glutamine profile (Y-axis; glutamine [mM]) of the same cells over time (X-axis; culture time [d]).

Figure 10A:
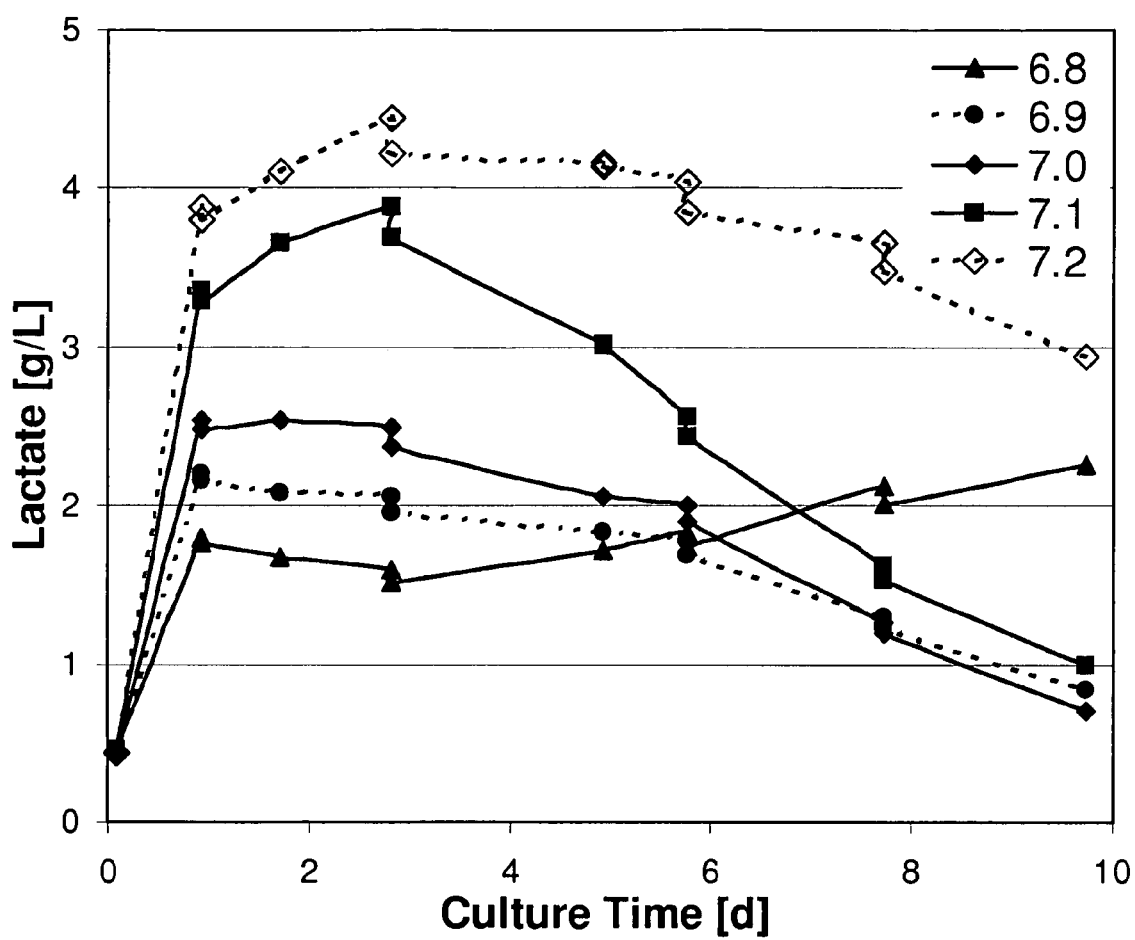
Figure 10B:
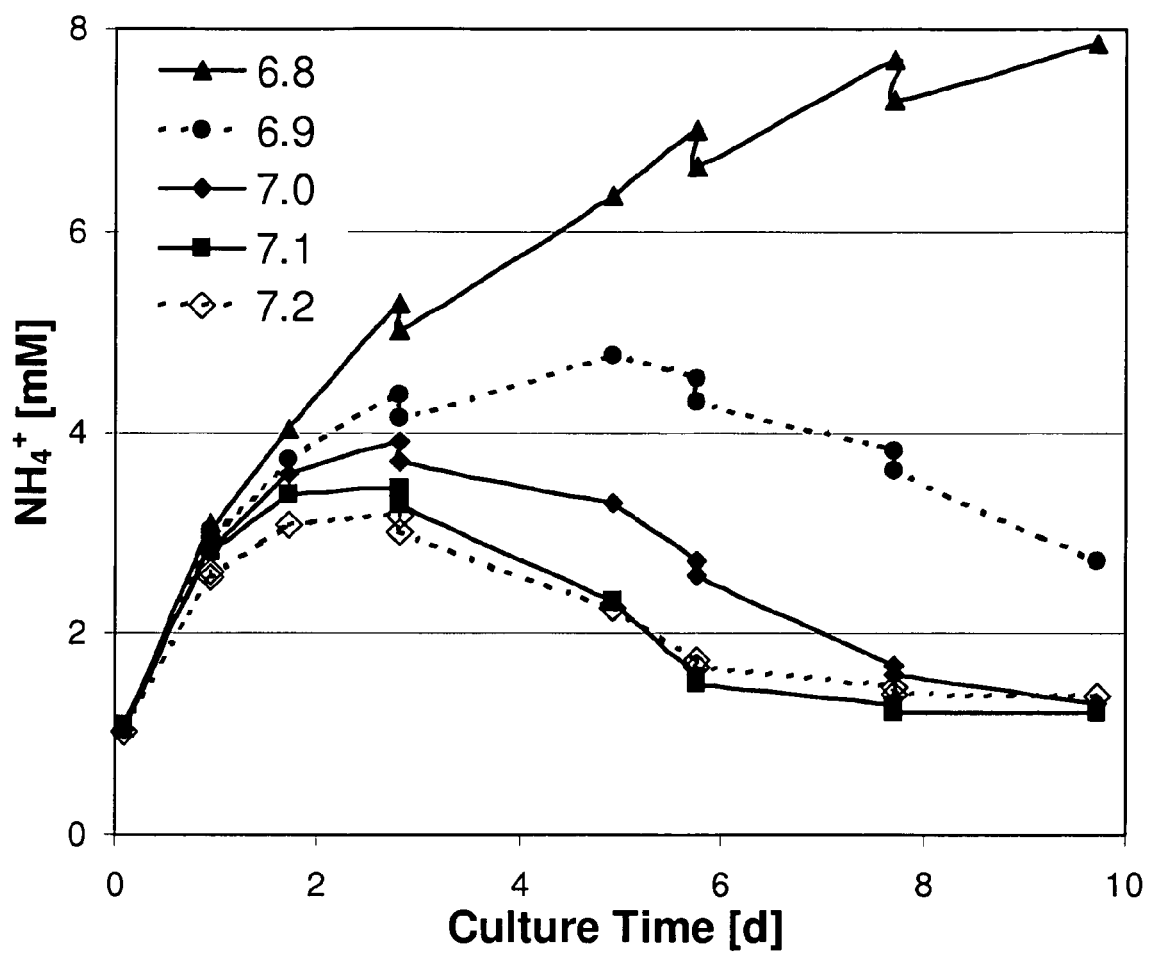

FIG. 10A represents lactate concentration in the media (Y-axis; lactate [g/L]) of the cell culture of CHO cells transfected with TNFR-Fc grown at pH set point of either 7.20 [◊], 7.10 [■], 7.00 [♦], 6.90 [●], or 6.80 [▲] over time (X-axis; culture time [d]); while FIG. 10B represents ammonium profile (Y-axis; $NH_4^+$ [mM]) of the same cells over time (X-axis; culture time [d]).

Figure 11A:
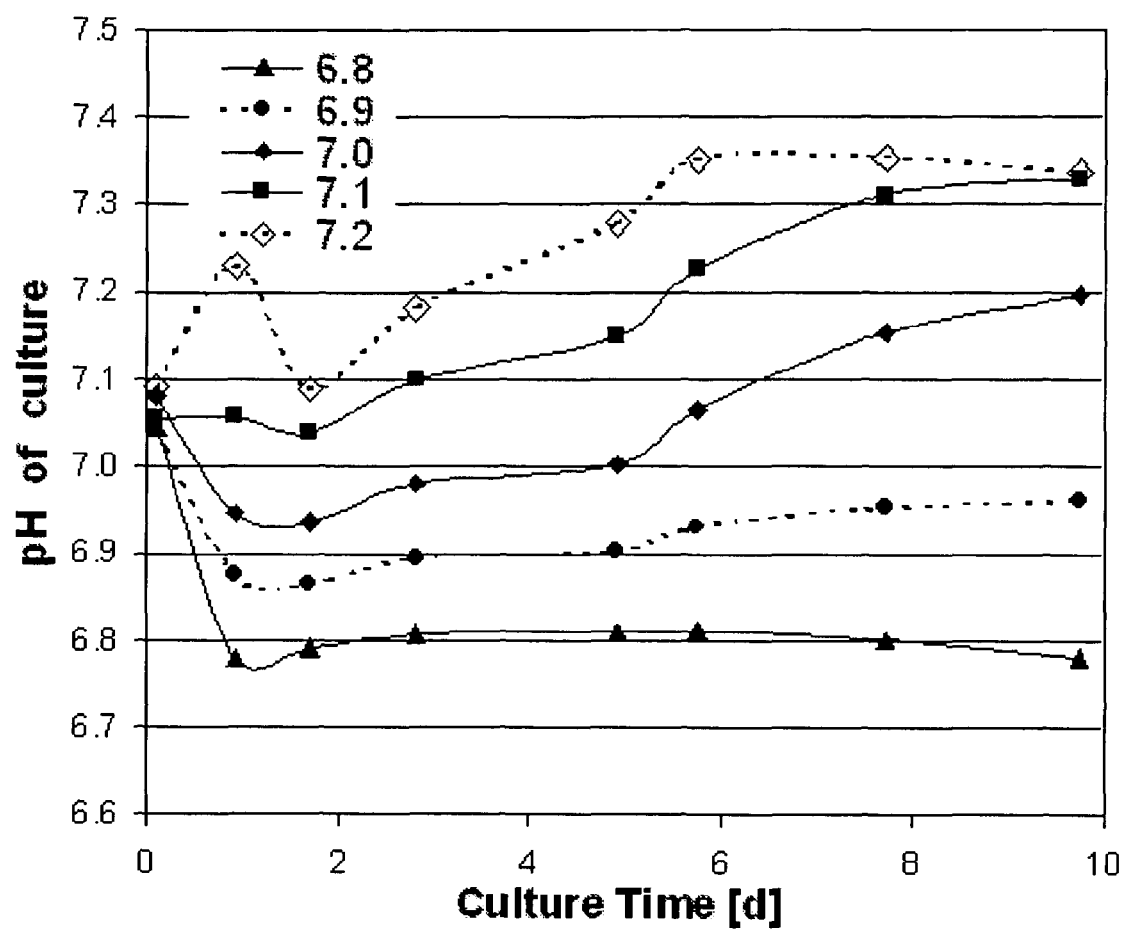
Figure 11B:
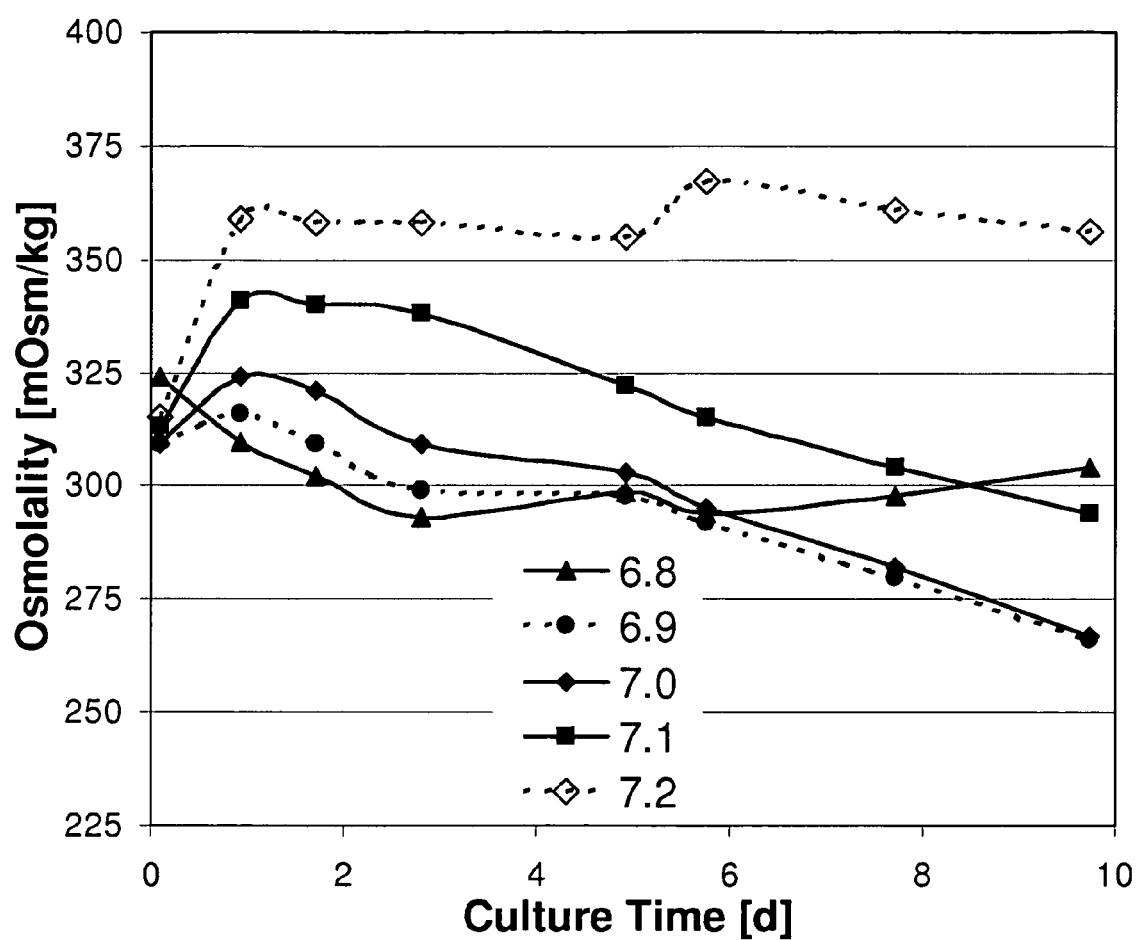

FIG. 11A represents deviations of the pH of the cell culture from the pH set point (X-axis; pH of culture), where the CHO cells transfected with TNFR-Fc were grown at a pH set point of either 7.20 [◊], 7.10 [■], 7.00 [♦], 6.90 [●], or 6.80 [▲] over time (X-axis; culture time [d]). FIG. 11B represents osmolarity (X-axis; osmolarity [mOsm/kg]) of the same cells grown at a pH set point of either 7.20 [◊], 7.10 [■], 7.00 [♦], 6.90 [●], or 6.80 [▲] over time (X-axis; culture time [d]).

Figure 12A:
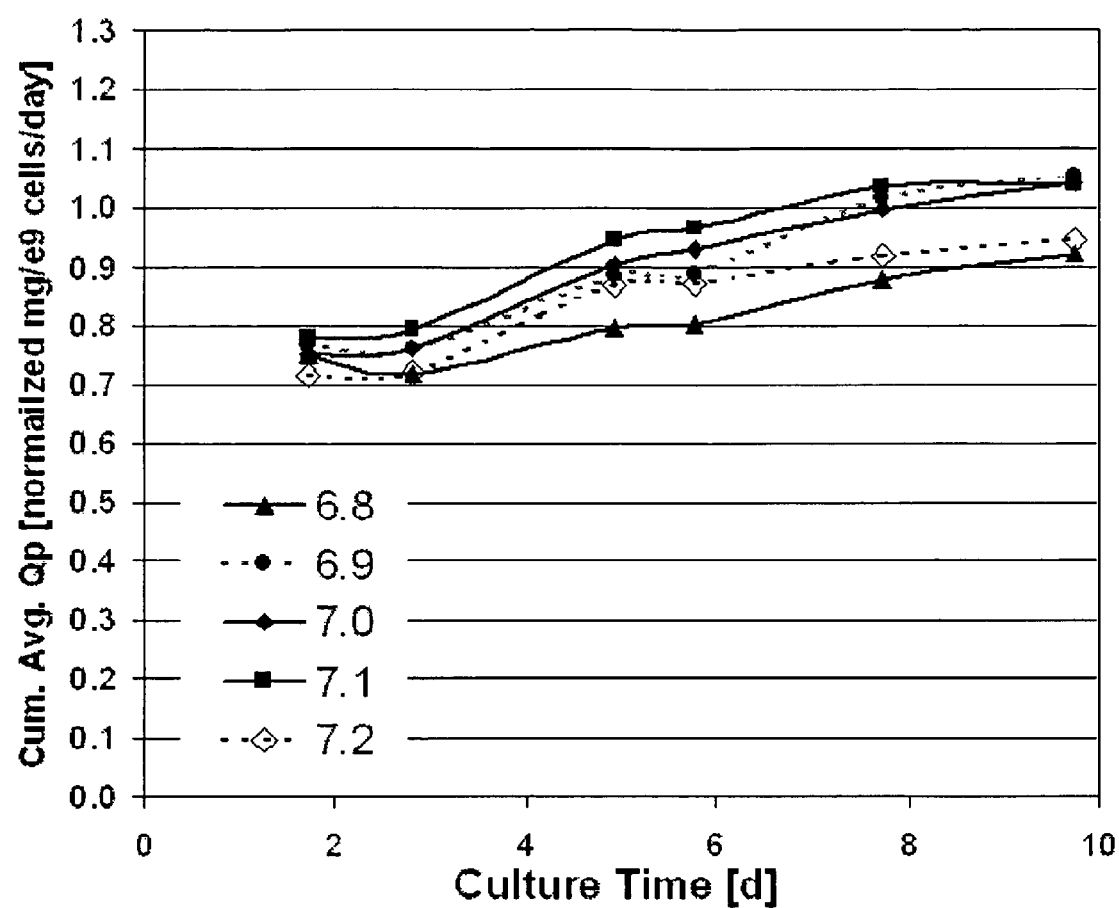
Figure 12B:
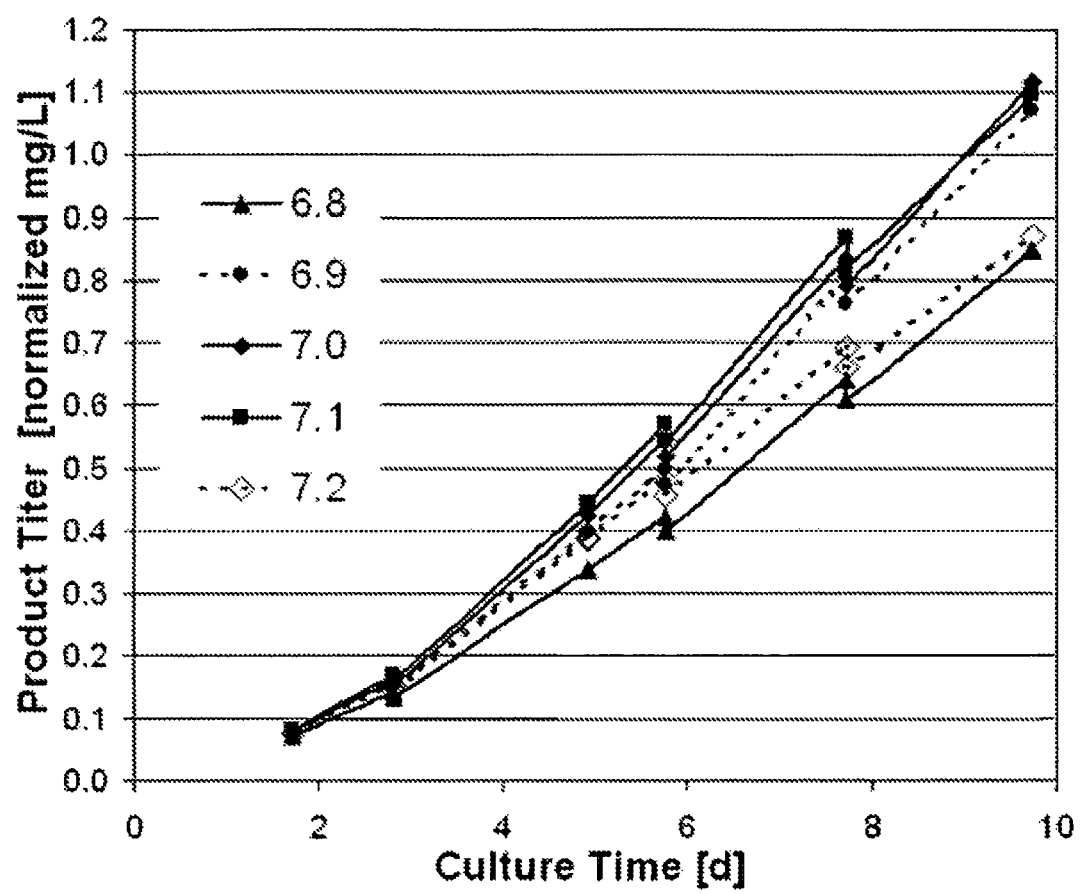

FIG. 12A represents cell specific productivities, represented by cumulative average Qp (X-axis; Cum. Avg. Qp [normalized mg/$e^9$ cells/day]), normalized to average harvest day cumulative average Qp, of the cell culture of CHO cells transfected with TNFR-Fc grown at pH set point of either 7.20 [◊], 7.10 [■], 7.00 [♦], 6.90 [●], or 6.80 [▲] over time (X-axis; culture time [d]).; while FIG. 12B represents TNFR-Fc titer (X-axis; product titer [normalized mg/L]), normalized to average harvest day titer, of the same cells over time (culture time [d]).

Figure 13A:
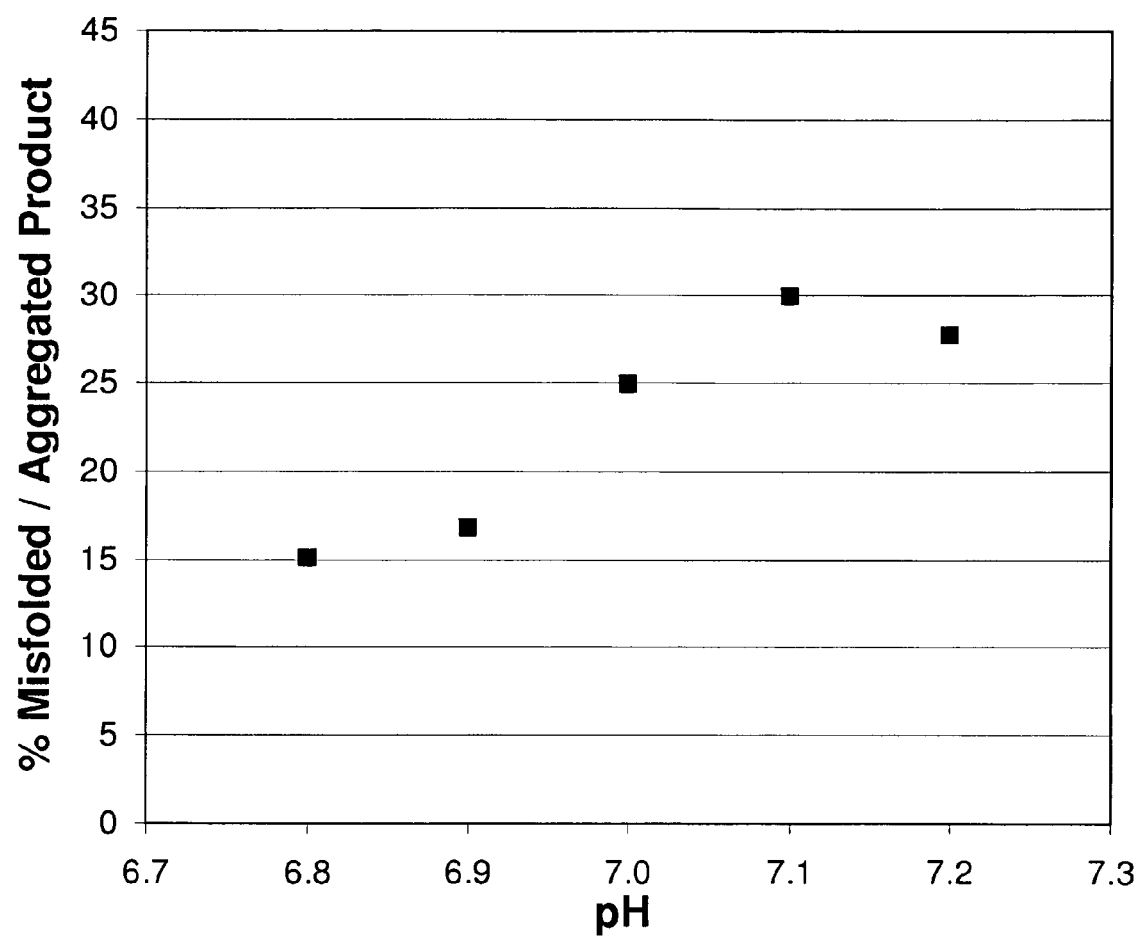
Figure 13B:
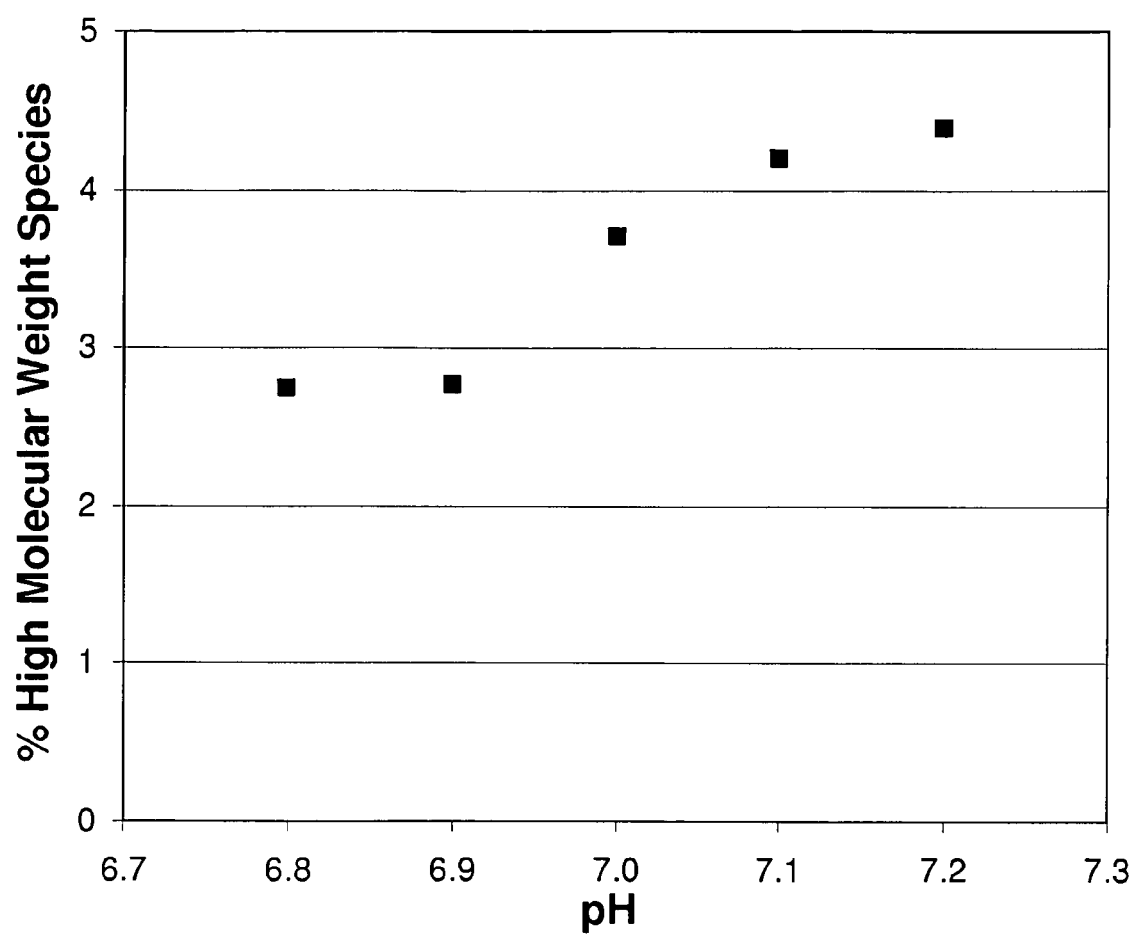

FIG. 13A represents the effect of varying the pH set point of the culture (X-axis; pH) of CHO cells transfected with TNFR-Fc on the production of misfolded/aggregated TNFR-Fc (Y-axis; % misfolded/aggregated product). FIG. 13B represents the effect of varying the pH set point of the cell culture (X-axis; pH) on the production of HMWA (Y-axis; % high molecular weigh species).

Figure 14A:
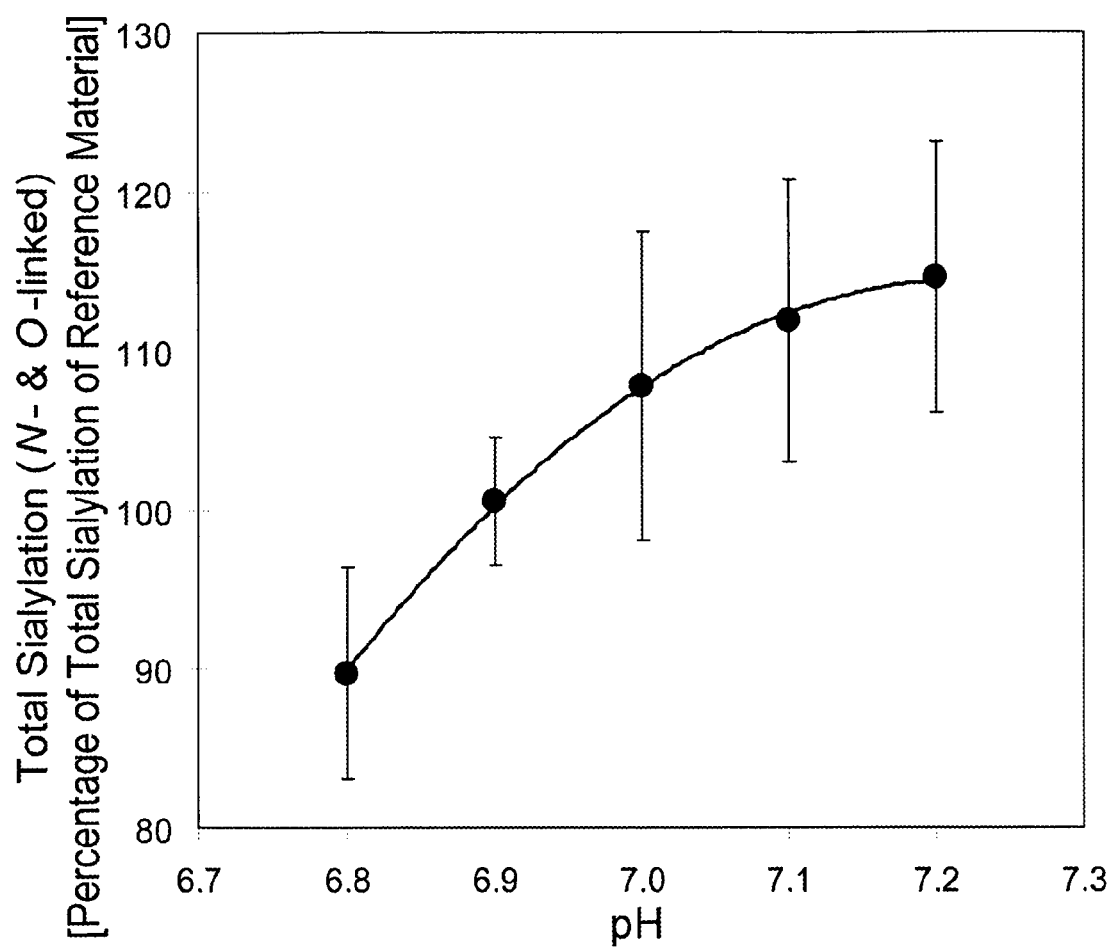
Figure 14B:
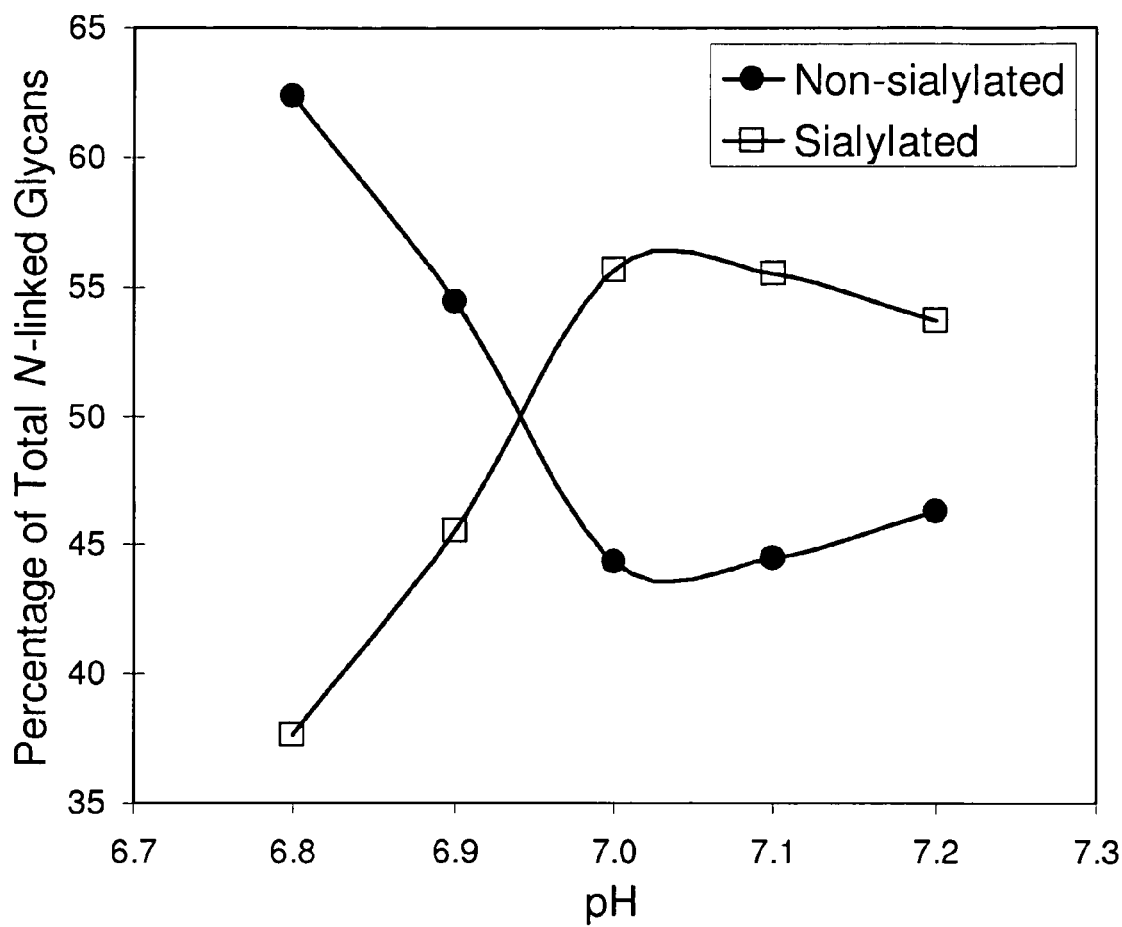

The effect of varying the pH set point (X-axis; pH) in the culture of CHO cells transfected with the TNFR-Fc on the percentage of total sialylation of TNFR-Fc (Y-axis; percentage of total sialylation of reference material) is demonstrated in FIG. 14A. FIG. 14B demonstrates the effect of varying cell culture pH set point (X-axis; pH) in the cell culture of the same cells on the percentage of total sialylated (□) or non-sialylated (●) N-linked glycans (Y-axis; Percentage of Total N-linked Glycans)

Figure 15:
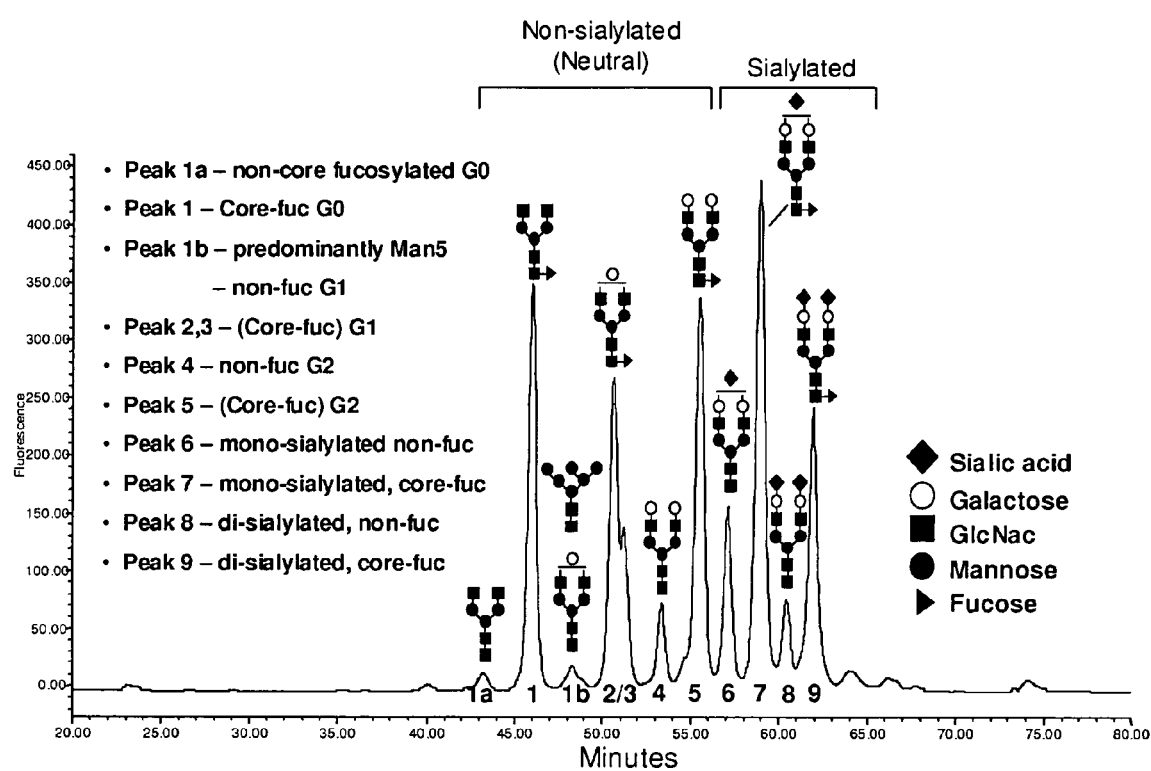

FIG. 15 depicts a typical fluorescence (Y-axis; fluorescence, measured in mV) versus retention time (X-axis; minutes) profile depicting N-linked glycan sialylation as observed by subjecting hydrazine released 2-aminobenzamide-(2-AB)-labeled protein glycoforms to Normal Phase Chromatography.

Figure 16:
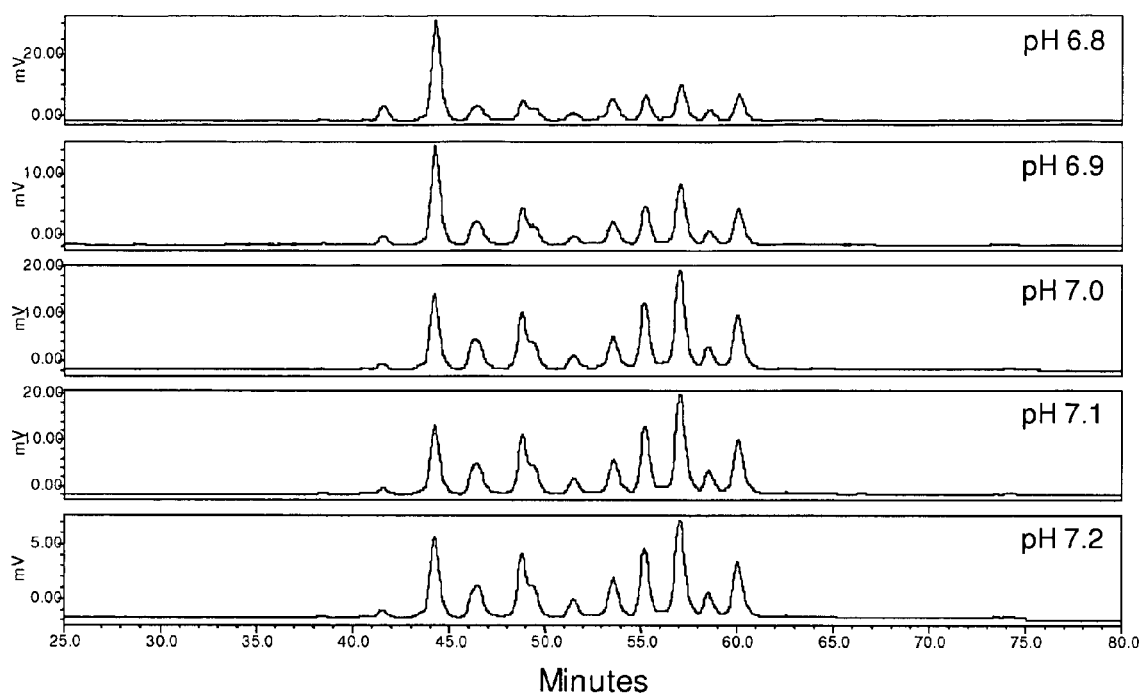

FIG. 16 depicts the fluorescence (Y-axis; mV) versus retention time (X-axis; minutes) profiles depicting N-linked glycan sialylation as observed by subjecting hydrazine released 2-aminobenzamide-(2-AB)-labeled protein glycoforms to Normal Phase Chromatography of cell culture of CHO cells transfected with TNFR-Fc at varying pH set points of the culture.

FIG. 17 represents (A) viable cell density (Y-axis; cells/mL), (B) total cell density, which includes both viable and non-viable cells, (Y-axis; cells/mL), (C) cell viability (Y-axis), and (D) integrated viable cell numbers (IVC) (Y-axis; e9 cells*day/L) of the cell culture of sIL-13R overexpressing cells grown at 37.0° C. [♦], 33.0° C. [■], 32.0° C. [●], 31.0° C. [◊], 29.0° C. [Δ], or RT [□] over time (X-axis; culture time [d]).

Figure 18:
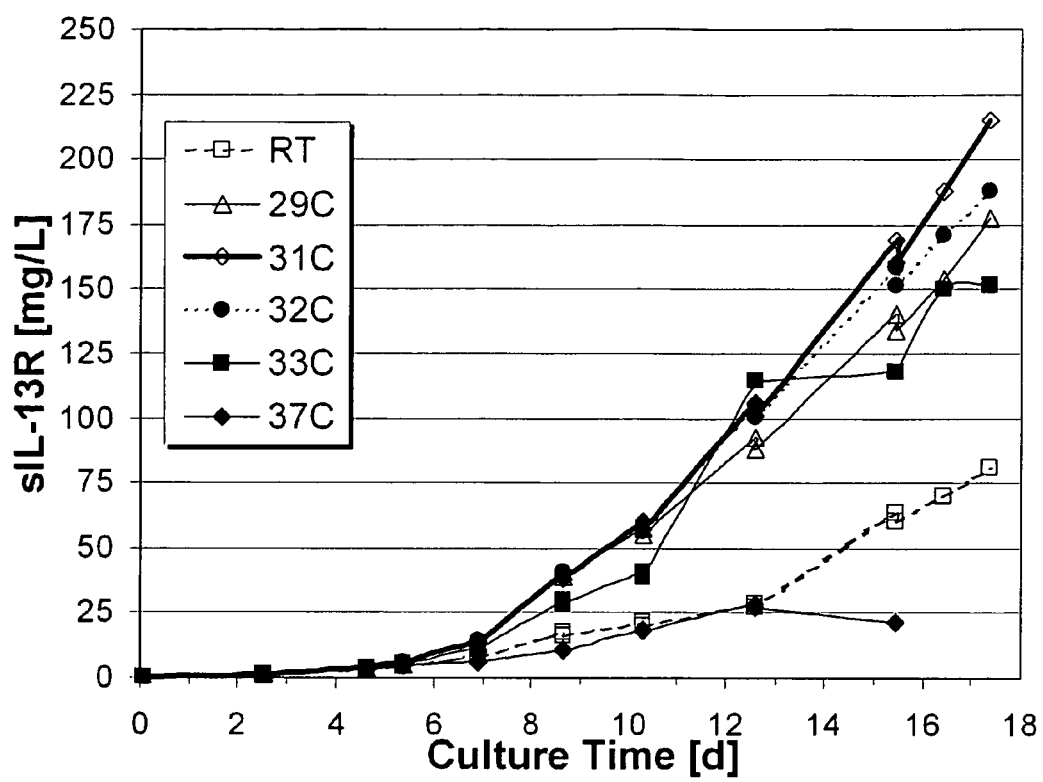

FIG. 18 represents sIL-13R titer, both dimer and HMWA, (Y-axis; sIL-13R [mg/L]) for cell cultures overexpressing sIL-13R, grown at 37.0° C. [♦], 33.0° C. [■], 32.0° C. [●], 31.0° C. [◊], 29.0° C. [Δ], or RT [□] overtime (X-axis; culture time [d]).

Figure 19A:
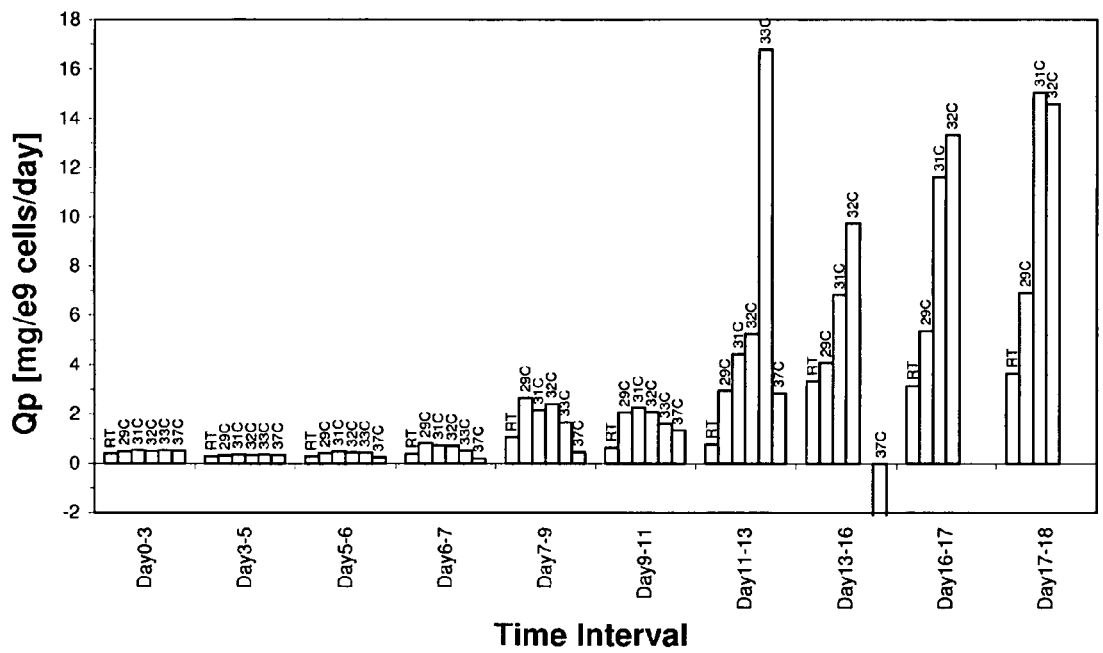
Figure 19B:
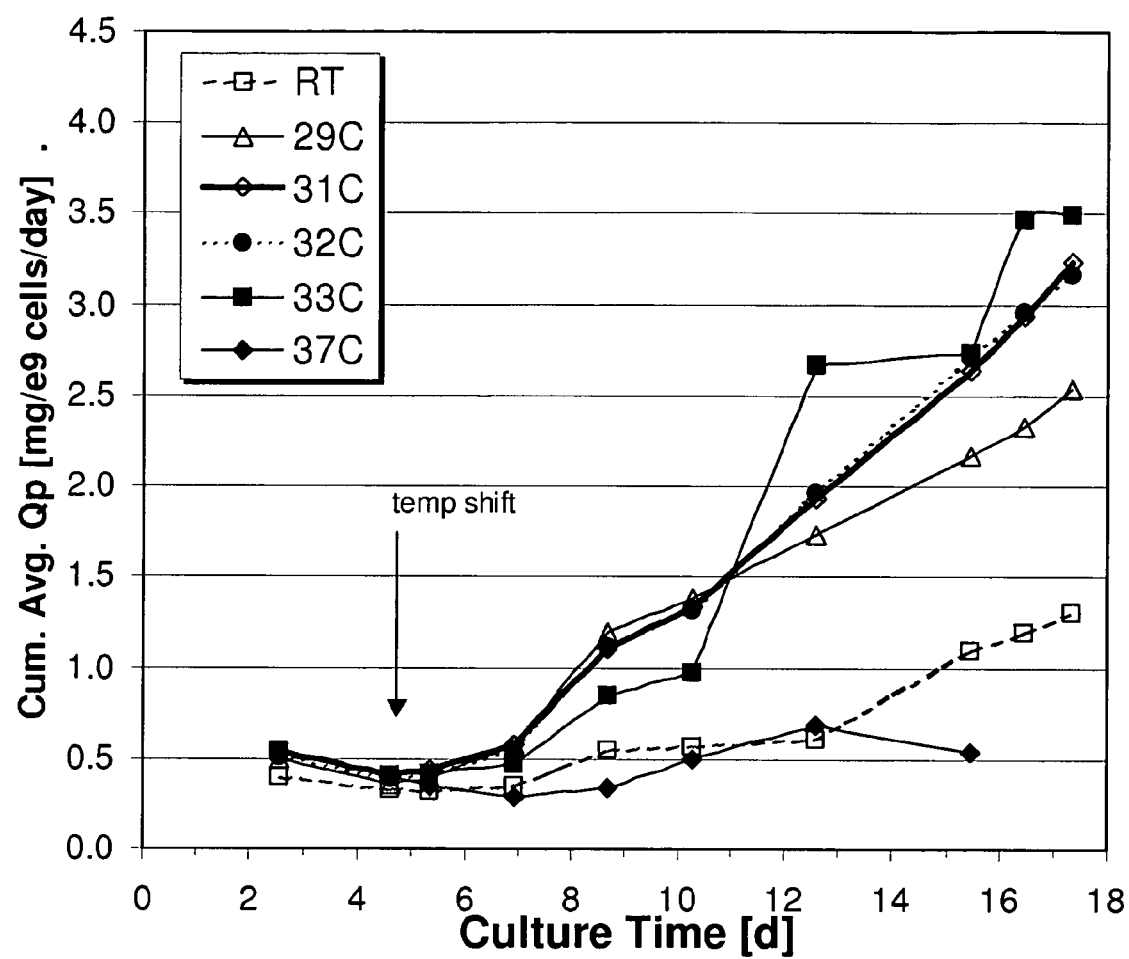

FIG. 19A represents daily specific sIL-13R production rate (Y-axis; Qp [ug/e9 cells/d]) during various time intervals (X-axis) for cell cultures overexpressing sIL-13R, grown at 37.0° C., 33.0° C., 32.0° C., 31.0° C., 29.0° C., or RT. FIG. 19B represents cumulative average cell specific productivities (Y-axis; Cum. Avg. Qp [mg/e9 cells/day]) over time (X-axis; culture time [d]) for cell cultures overexpressing sIL-13R, grown at 37.0° C., 33.0° C., 32.0° C., 31.0° C., 29.0° C., or RT.

Figure 20:
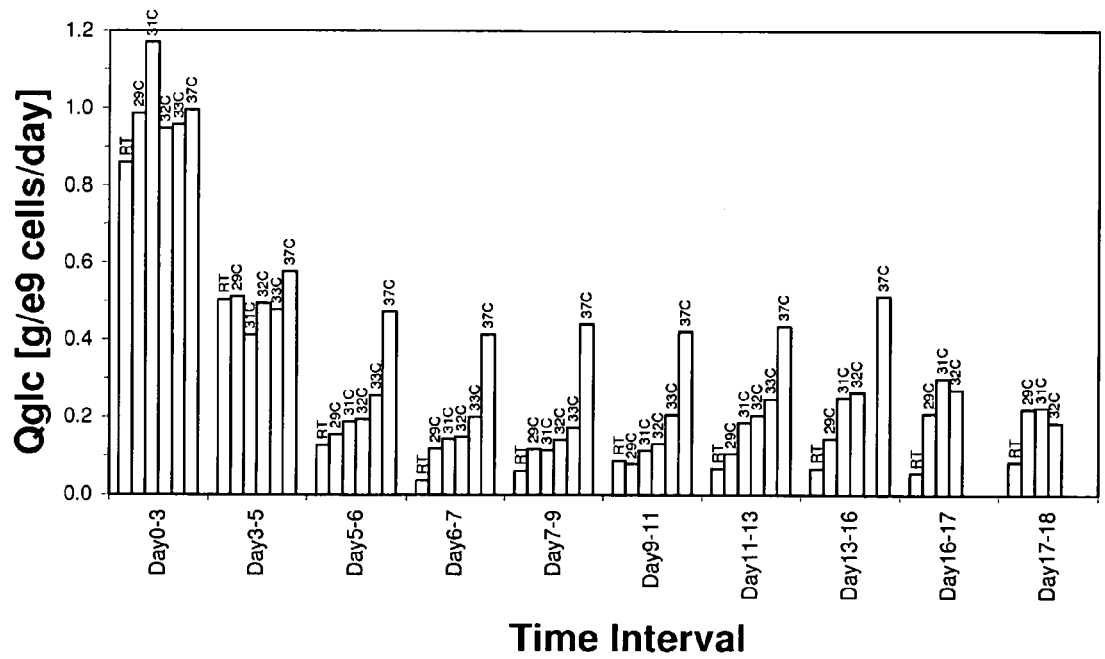
Figure 21:
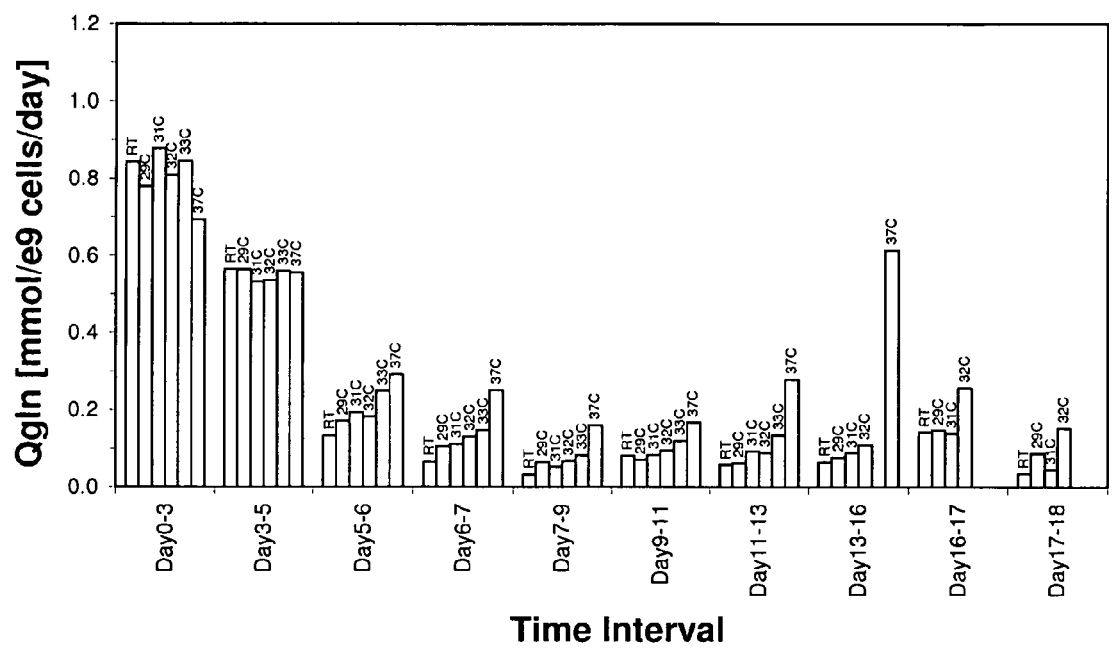

FIG. 20 represents daily specific glucose consumption rate (Y-axis; Qglc [g/e$^9$ cell/d]) for different time intervals (X-axis) for cell cultures overexpressing sIL-13R, grown at 37.0° C., 33.0° C., 32.0° C., 31.0° C., 29.0° C., or RT FIG. 21 represents daily specific glutamine consumption rate (Y-axis; Qgln [mmol/e9 cell/d]) for different time intervals (X-axis) for cell cultures overexpressing sIL-13R, grown at 37.0° C., 33.0° C., 32.0° C., 31.0° C., 29.0° C., or RT.

Figure 22:
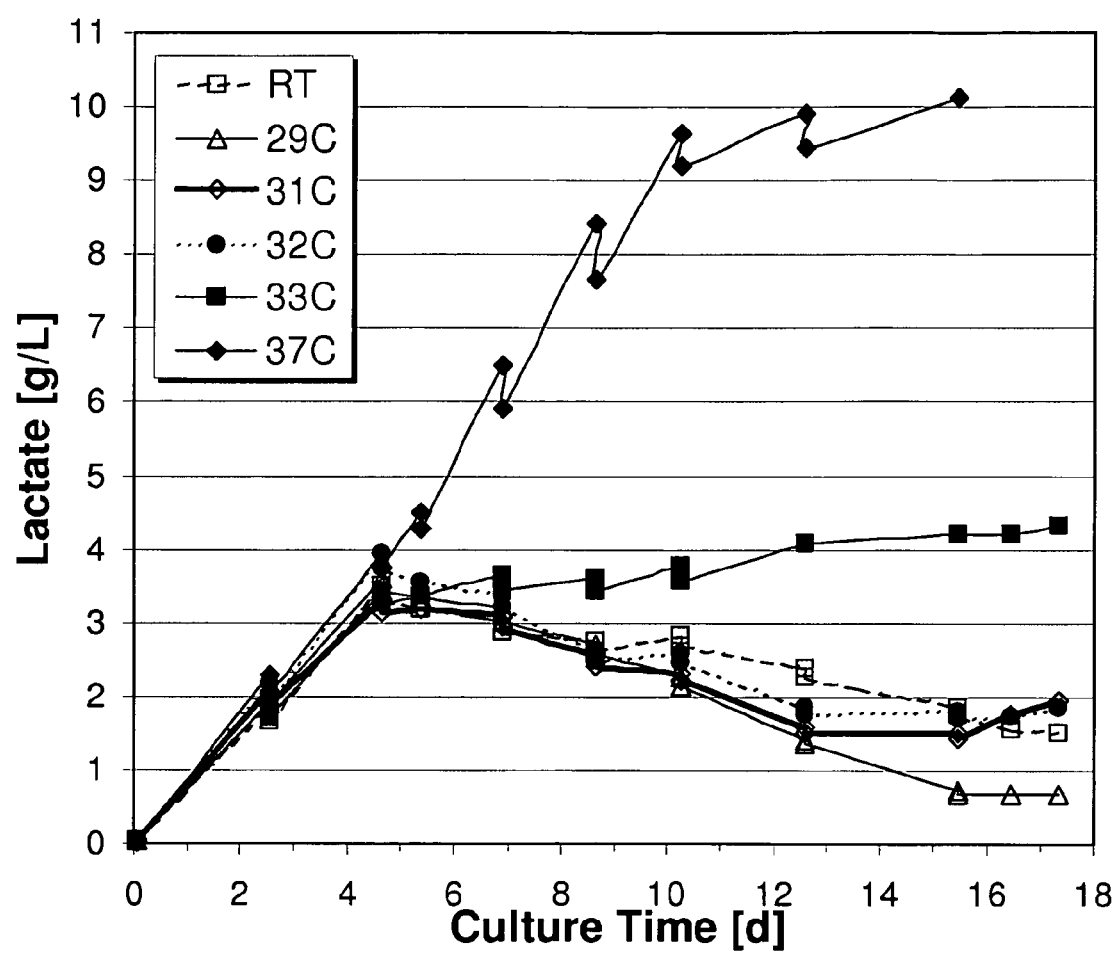

FIG. 22 represents lactate concentration (Y-axis; lactate [g/L]) in the cell culture medium of the cells overexpressing sIL-13R, grown at 37.0° C. [♦], 33.0° C. [■], 32.0° C. [●], 31.0° C. [◇], 29.0° C. [Δ], or RT [□] overtime (X-axis; culture time [d]).

Figure 23:
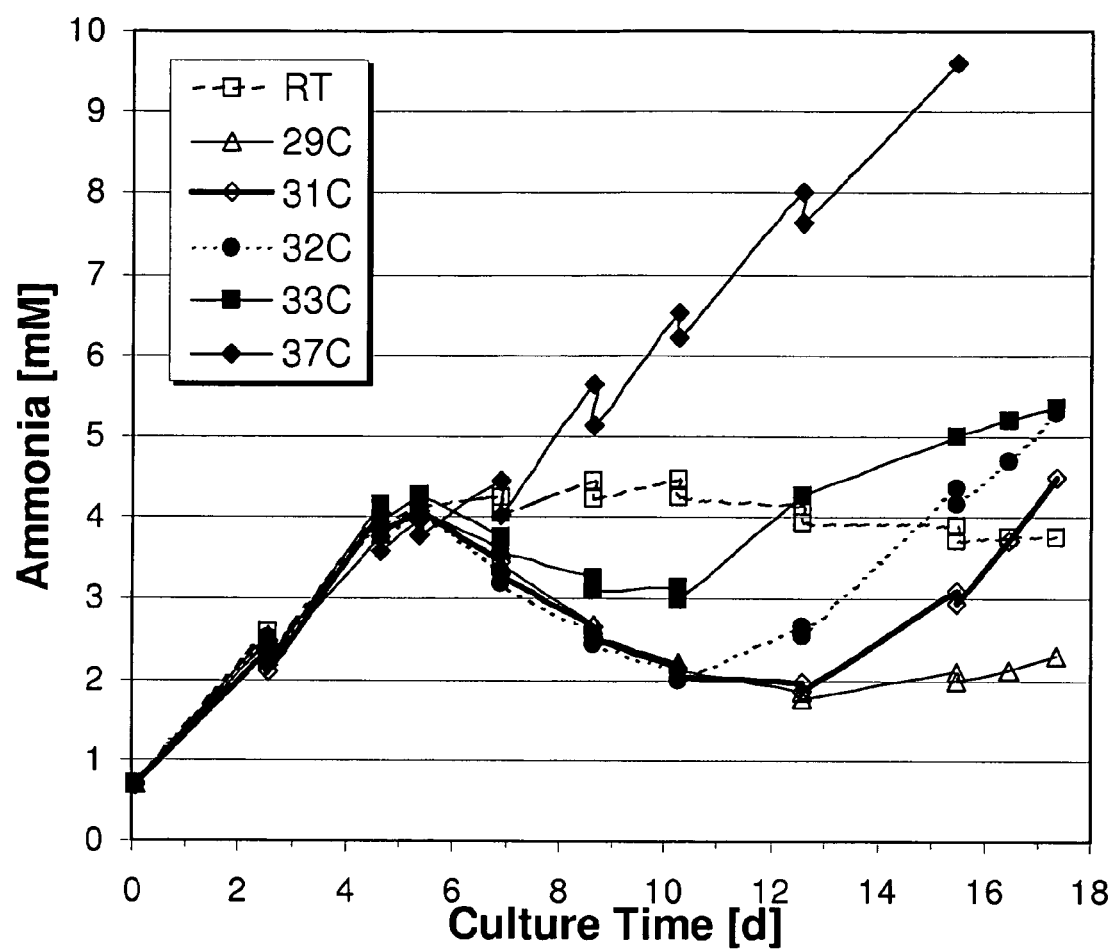

FIG. 23 represents ammonium concentration (Y-axis; ammonia [mM]) in the cell culture medium of the cells overexpressing sIL-13R, grown at 37.0° C. [♦], 33.0° C. [■], 32.0° C. [●], 31.0° C. [◇], 29.0° C. [Δ], or RT [□] overtime (X-axis; culture time [d]).

Figure 24:
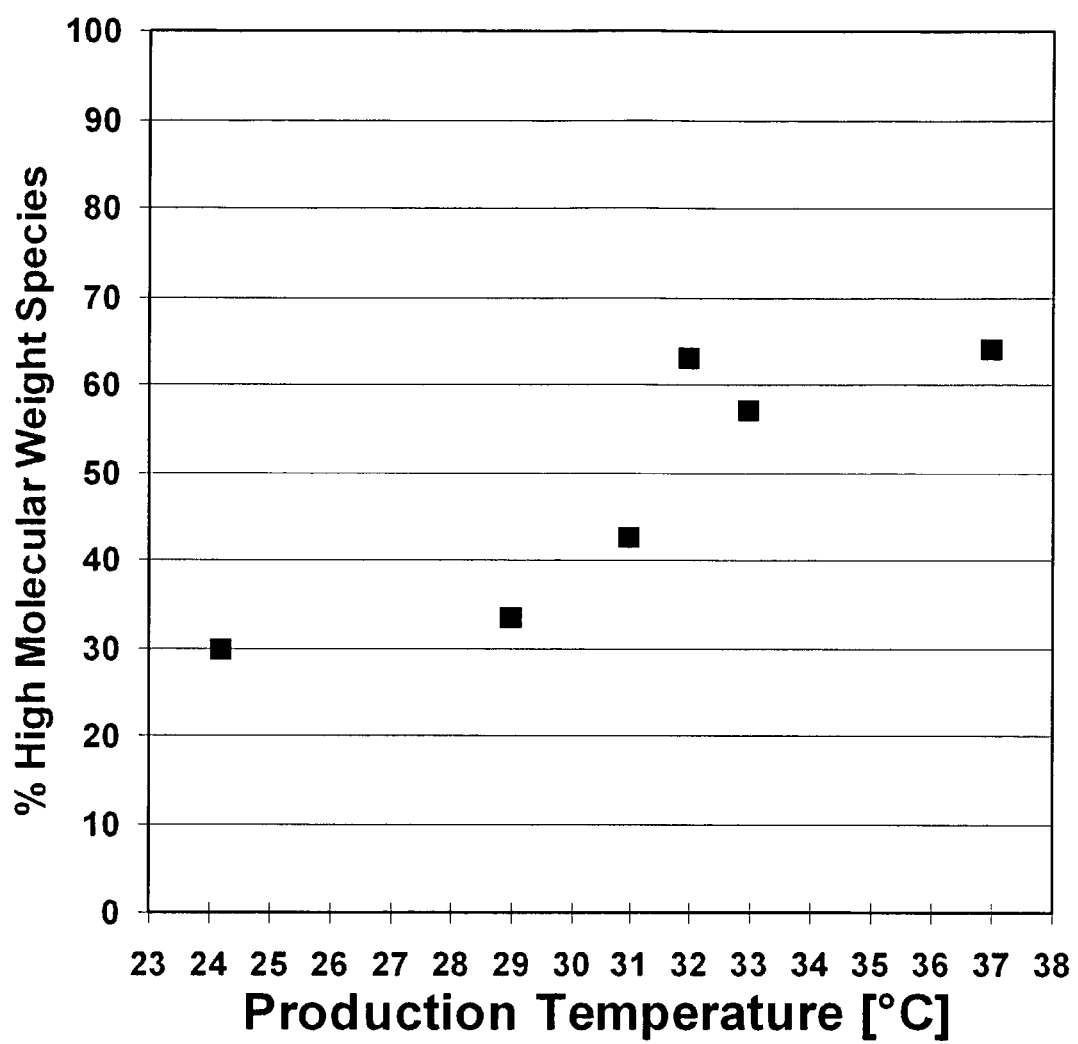

FIG. 24 represents the effect of cell culture temperature (X-axis; production temperature [° C.]) on the production of HMWA (Y-axis; % High Molecular Weight Species) on day 9 of culture of cells overexpressing sIL-13R.

Figure 25:
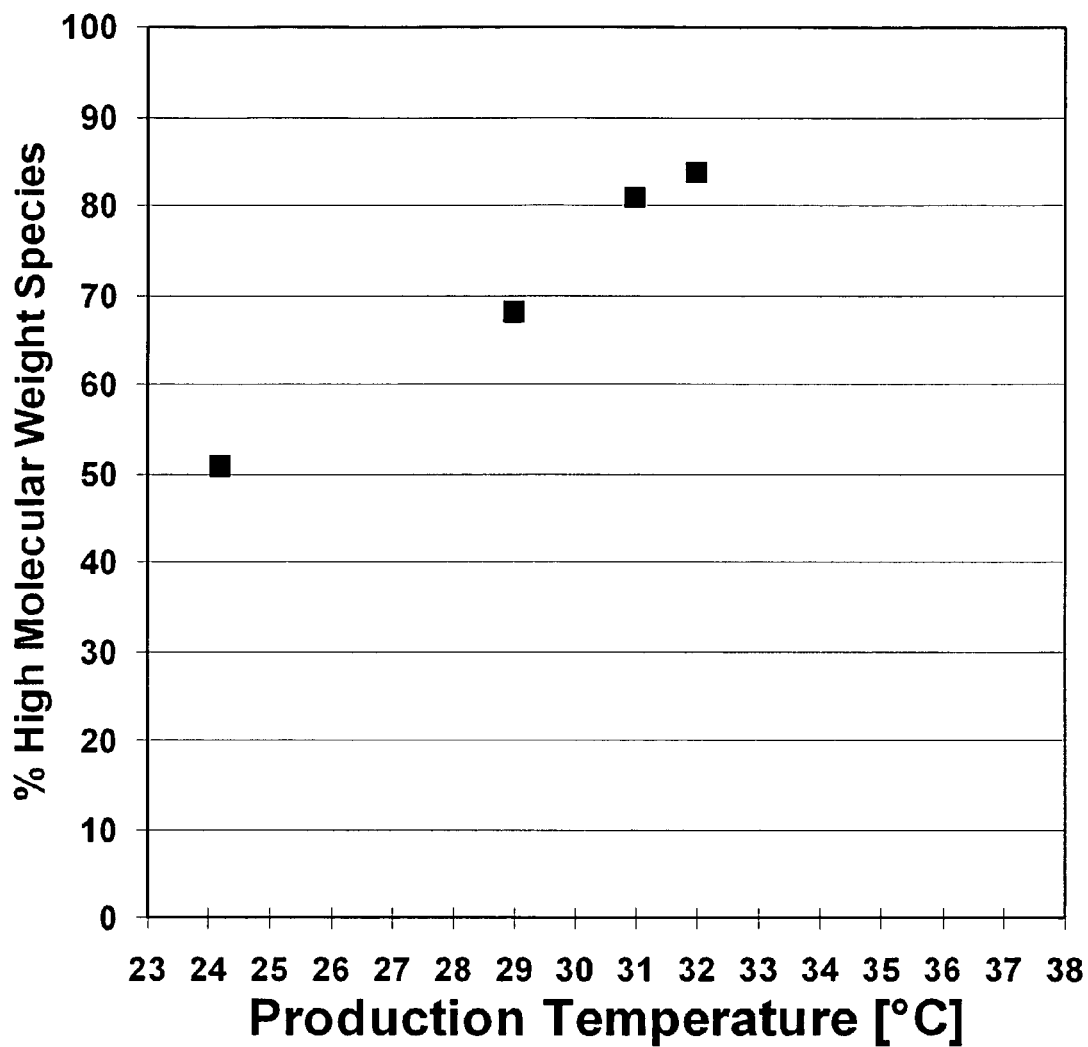

FIG. 25 represents the effect of cell culture temperature (X-axis; production temperature [° C.]) on the production of HMWA (Y-axis; % High Molecular Weight Species) on day 18 of culture of cells overexpressing sIL-13R.

Figure 26A:
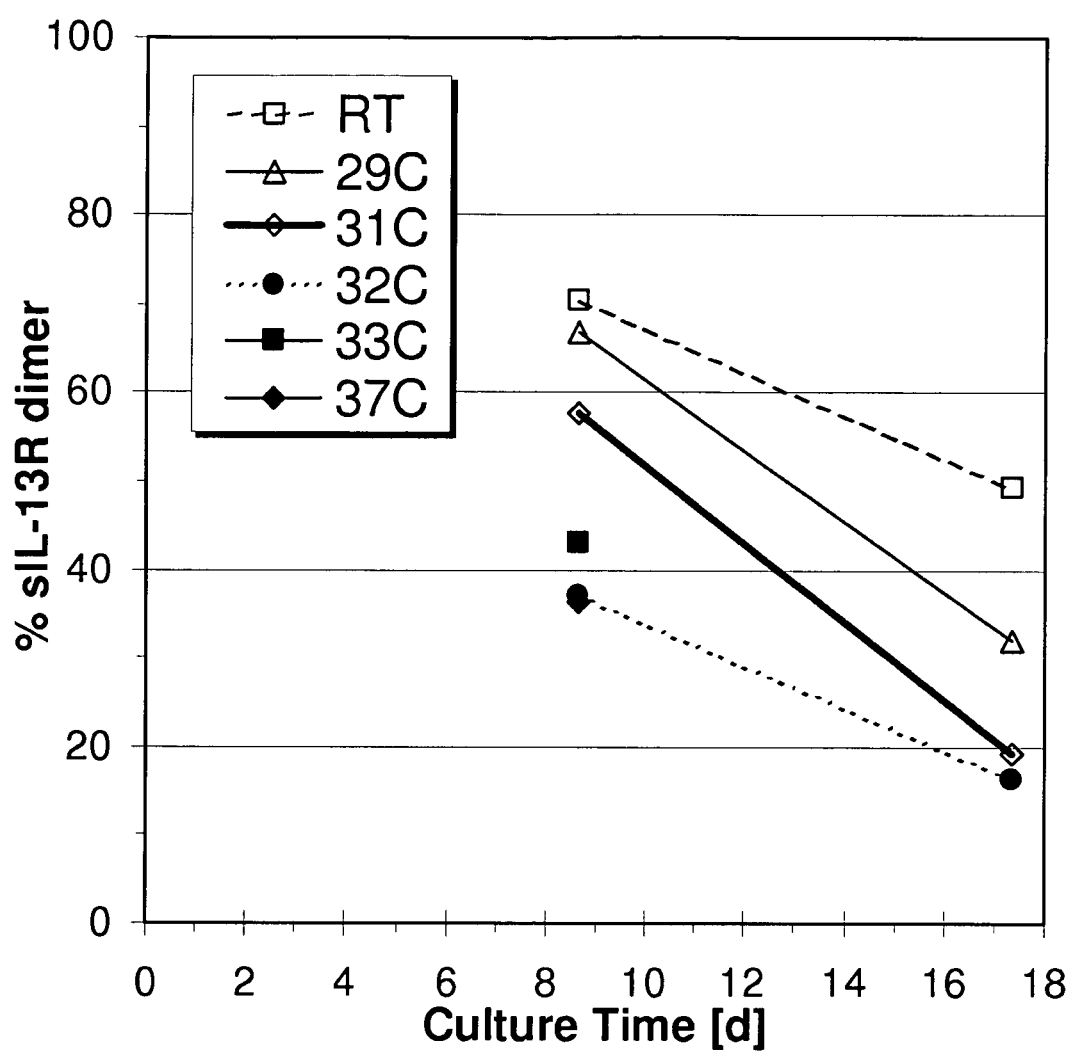
Figure 26B:
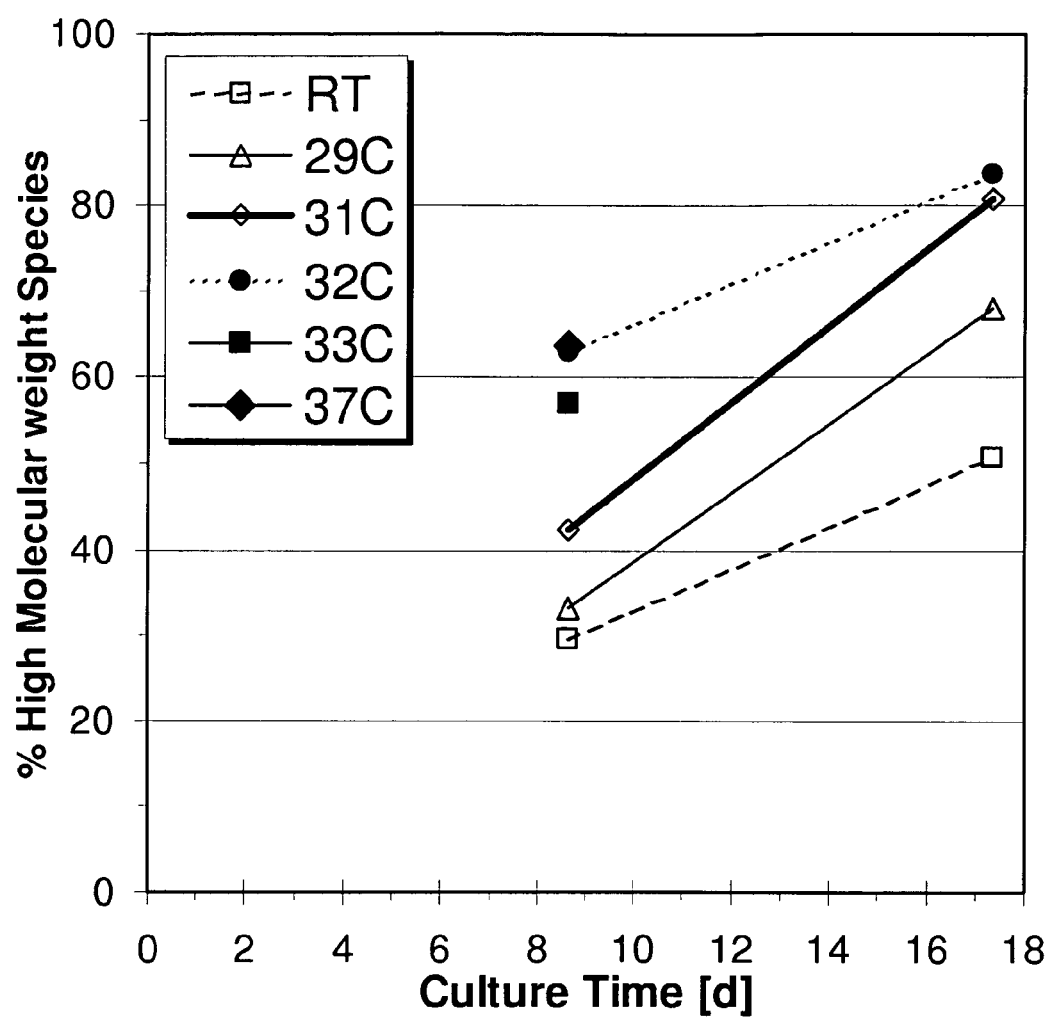

FIG. 26A represents percentage of the sIL-13R dimer (Y-axis; % sIL-13R dimer) recovered from the total sIL-13R protein produced in the conditioned media of sIL-13R overexpressing cells grown at either 37.0° C. [♦], 33.0° C. [■], 32.0° C. [●], 31.0° C. [◇], 29.0° C. [Δ], or RT [□] over time (X-axis; culture time [d]). FIG. 26B represents the percentage of HMWA (Y-axis; % High Molecular Weight Species) relative to total sIL-13R in the conditioned medium of sIL-13R overexpressing cells over time (X-axis; culture time [d]).

Figure 27:
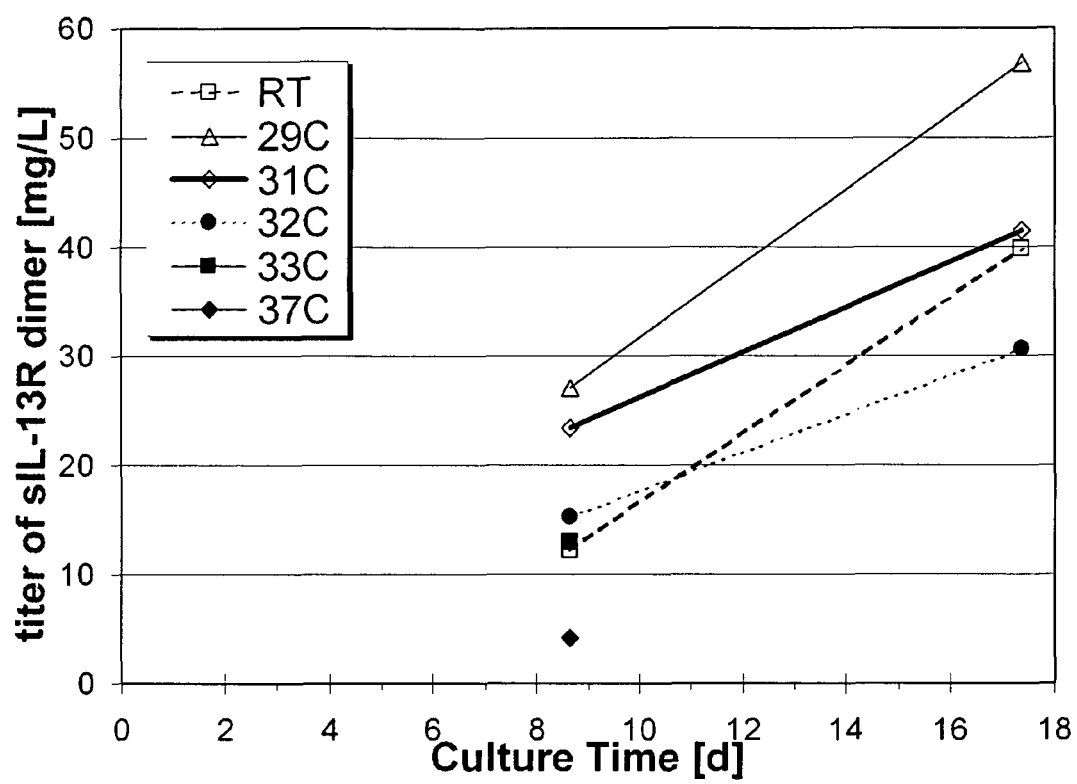

FIG. 27 represents the sIL-13R dimer titer (Y-axis; sIL-13R dimer only [mg/L]) in the conditioned media of cells grown either 37.0° C. [♦], 33.0° C. [■], 32.0° C. [●], 31.0° C. [◇], 29.0° C. [Δ], or RT [□] over time (X-axis; culture time [d]).

DETAILED DESCRIPTION OF THE INVENTION

The prevailing wisdom for producing therapeutic proteins in a mammalian cell culture is that the temperature during the production phase should be at least 30.0° C. and the pH should be at least 7.00. However, growing cells in a cell culture during a production phase at temperatures above 30.0° C. and at a pH above 7.00 can lead to increased protein aggregation (also referred to herein as high molecular weight aggregate, or HMWA, formation) and protein misfolding, and thus production of lower quantity of functional and usable protein.

The present invention provides a novel method of protein production in a cell culture, wherein the method results in decreased protein misfolding and/or decreased protein aggregation. In another aspect the invention provides for methods of controlling the level of protein glycosylation.

Proteins Produced by Methods of the Invention

As used herein, the phrases "polypeptide" or "polypeptide product" are synonymous with the terms "protein" and "protein product," respectively, and, as is generally understood in the art, refer to at least one chain of amino acids linked via sequential peptide bonds. In certain embodiments, a "protein of interest" or a "polypeptide of interest" or the like is a protein encoded by an exogenous nucleic acid molecule that has been transfected or transformed into a host cell, e.g., transiently or stably transfected or transformed into a host cell. In certain embodiments, wherein an exogenous DNA with which the host cell has been transfected or transformed codes for the "protein of interest," the nucleic acid sequence of the exogenous DNA determines the sequence of amino acids. This sequence may be a sequence that occurs in nature, or may alternatively be a sequence engineered by man. In certain embodiments, a "protein of interest" is a protein encoded by a nucleic acid molecule that is endogenous to the host cell. The expression of such an endogenous protein of interest may be altered by transfecting a host cell with an exogenous nucleic acid molecule that may, for example, contain one or more regulatory sequences and/or encode a protein that enhances expression of the protein of interest. In the embodiments of the present invention, a polypeptide of interest is produced in the cell culture, e.g., for subsequent purification.

The term "glycoprotein," "glycosylated protein" and the like refers to proteins that have sugar moieties, e.g., oligosaccharide moieties, attached to either their asparagine side chains (N-glycosylation) or their serine and/or threonine side chains (O-glycosylation). For instance, one common type of protein N-glycosylation is protein sialylation (also known as N-glycan sialylation). The majority of secretory and membrane proteins (e.g., membrane receptors) are glycosylated in the ER and/or the Golgi apparatus. It is known in the art that glycosylation controls protein folding and release in the ER. Additionally, multiple steps of glycosylation/deglycosylation occur in the Golgi. Present understanding of protein glycosylation processes in both ER and Golgi are reviewed in Helenius et al. (2001) *Science* 291:2364-69; Parodi (2000) *Biochem. J.* 348:1-13; and Parodi (2000) *Annu. Rev. Biochem.* 69:69-93. Thus, in certain embodiments of the present invention, the polypeptide of interest is a glycoprotein of interest, and the glycoprotein of interest is produced in the cell culture, e.g., for subsequent purification. In one embodiment of the present invention, the glycoprotein of interest is a receptor, and may be a soluble receptor.

Methods and compositions of the present invention may be used to produce any protein of interest including, but not limited to, proteins having pharmaceutical, diagnostic, agricultural, and/or any of a variety of other properties that are useful in commercial, experimental and/or other applications. In addition, a protein of interest can be a protein therapeutic. Namely, a protein therapeutic (or a therapeutic protein) is a protein that has a biological effect on a region in the body on which it acts or on a region of the body on which it remotely acts via intermediates. In certain embodiments, proteins produced using methods and/or compositions of the present invention may be processed and/or modified, before administering to a subject as a therapeutic protein.

The present invention may be used to culture cells for the advantageous production of any therapeutic protein, such as pharmaceutically or commercially relevant enzymes, receptors, receptor fusions, soluble receptors, soluble receptor fusions, antibodies (e.g., monoclonal and/or polyclonal antibodies), antigen-binding fragments of an antibody, Fc fusion proteins, SMIPs, cytokines, hormones, regulatory factors, growth factors, coagulation/clotting factors, or antigen-binding agents. The above list of proteins is merely exemplary in nature, and is not intended to be a limiting recitation. One of ordinary skill in the art will know of other proteins that can be produced in accordance with the present invention, and will be able to use methods disclosed herein to produce such proteins.

The term "antibody" includes a protein comprising at least one, and typically two, VH domains or portions thereof, and/or at least one, and typically two, VL domains or portions thereof. In certain embodiments, the antibody is a tetramer of two heavy immunoglobulin chains and two light immunoglobulin chains, wherein the heavy and light immunoglobulin chains are inter-connected by, e.g., disulfide bonds. The antibodies, or a portion thereof, can be obtained from any origin, including, but not limited to, rodent, primate (e.g., human and non-human primate), camelid, shark as well as recombinantly produced, e.g., chimeric, humanized, and/or in vitro generated, e.g., by methods well known to those of skill in the art.

This invention also encompasses "antigen-binding fragments of antibodies", which include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized variable domain, e.g., a VHH domain; (vii) a single chain Fv (scFv); (viii) a bispecific antibody; and (ix) one or more antigen binding fragments of an immunoglobulin fused to an Fc region. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-26; Huston et al. (1988) Proc. Natl. Acad. Sci. U.S.A. 85:5879-83). Such single chain antibodies are also intended to be encompassed within the term "antigen-binding fragment" of an antibody. These antibody fragments are obtained using conventional techniques known to those skilled in the art, and the fragments are evaluated for function in the same manner as are intact antibodies.

The invention also encompasses single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, cow and shark. According to one aspect of the invention, a single domain antibody as used herein is a naturally occurring single domain antibody known as heavy chain antibody devoid of light chains. Such single domain antibodies are disclosed in WO 9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention. Single domain antibodies also include shark IgNARs; see, e.g., Dooley et al., Proc. Natl. Acad. Sci. U.S.A., 103:1846-1851 (2006).

Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

In embodiments where the protein is an antibody or a fragment thereof, it can include at least one, or two full-length heavy chains, and at least one, or two light chains. Alternatively, the antibodies or fragments thereof can include only an antigen-binding fragment (e.g., an Fab, F(ab')2, Fv or a single chain Fv fragment). The antibody or fragment thereof can be a monoclonal or single specificity antibody. The antibody or fragment thereof can also be a human, humanized, chimeric, CDR-grafted, or in vitro generated antibody. In yet other embodiments, the antibody has a heavy chain constant region chosen from, e.g., IgG1, IgG2, IgG3, or IgG4. In another embodiment, the antibody has a light chain chosen from, e.g., kappa or lambda. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). Typically, the antibody or fragment thereof specifically binds to a predetermined antigen, e.g., an antigen associated with a disorder, e.g., a neurodegenerative, metabolic, inflammatory, autoimmune and/or a malignant disorder.

Proteins described herein, optionally, further include a moiety that enhances one or more of, e.g., stability, effector cell function or complement fixation. For example, an antibody or antigen-binding protein can further include a pegylated moiety, albumin, or a heavy and/or a light chain constant region.

Antibodies are generally made, for example, via traditional hybridoma techniques (Kohler et al., Nature 256:495 499 (1975)), recombinant DNA methods (U.S. Pat. No. 4,816,567), or phage display techniques using antibody libraries (Clackson et al., Nature 352:624 628 (1991); Marks et al., J. Mol. Biol. 222:581 597 (1991)). For various other antibody production techniques, see Antibodies: A Laboratory Manual, eds. Harlow et al., Cold Spring Harbor Laboratory, 1988.

Further, the antibodies may be tagged with a detectable or functional label. These labels include radiolabels (e.g., 131I or 99Tc), enzymatic labels (e.g., horseradish peroxidase or alkaline phosphatase), and other chemical moieties (e.g., biotin).

"Small Modular Immunopharmaceutical" or (SMIP™) drugs (Trubion Pharmaceuticals, Seattle, Wash.) are single-chain polypeptides composed of a binding domain for a cognate structure such as an antigen, a counterreceptor or the like, a hinge region polypeptide having either one or no cysteine residues, and immunoglobulin CH2 and CH3 domains (see also www.trubion.com). SMIPs and their uses and applications are disclosed in, e.g., U.S. Published Patent Application Nos. 2007/002159, 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

In one embodiment of the invention, the protein of interest is a soluble receptor, e.g., a soluble receptor fusion protein. Membrane proteins, e.g., receptors, are usually glycosylated proteins. Therefore, the methods of the present invention are particularly beneficial in producing nonaggregated, properly folded and glycosylated soluble receptor fusion proteins.

Soluble proteins, e.g., soluble receptors, can be produced according to methods well known in the art. In one embodiment of the invention, a soluble receptor comprises an extracellular region of the receptor, or a fragment of the extracellular region of the receptor. In another embodiment of the invention, a soluble receptor comprises two polypeptides. The first polypeptide comprises a full-length receptor; alternatively, the first polypeptide comprises less than the full length of the receptor, e.g., an extracellular portion of the receptor. In one embodiment of the invention, the first polypeptide is a full-length cytokine receptor; alternatively the first polypeptide is less than the full length of the cytokine receptor, e.g., an extracellular portion of the cytokine receptor. Such a soluble receptor can also comprise an additional polypeptide, e.g., a GST, Lex-A, MBP polypeptide sequence or an immunoglobulin chain, including, e.g., an Fc fragment, a heavy chain constant region of the various isotypes, including: IgG1, IgG2, IgG3, IgG4, IgM, IgA1, IgA2, IgD, and IgE.

In one embodiment of the invention, a second polypeptide is preferably soluble. In some embodiments, the second polypeptide enhances the half-life, (e.g., the serum or circulatory half-life) of the linked polypeptide. In preferred embodiments, the second polypeptide includes at least a region of an immunoglobulin polypeptide. Immunoglobulin fusion polypeptides are known in the art and are described in, e.g., U.S. Pat. Nos. 5,516,964; 5,225,538; 5,428,130; 5,514,582; 5,714,147; and 5,455,165. Soluble fusion proteins are known to be susceptible to aggregation during production, and therefore the methods according to the invention provide a particular benefit in connection with cell cultures that produce proteins of this type.

In some embodiments, the second polypeptide comprises a full-length immunoglobulin polypeptide. Alternatively, the second polypeptide comprises less than the full length of immunoglobulin polypeptide, e.g., a heavy chain, light chain, Fab, Fab$_2$, Fv, or Fc. The second polypeptide can include the heavy chain of an immunoglobulin polypeptide. The second polypeptide can include the Fc region of an immunoglobulin polypeptide.

In one embodiment of the invention, a soluble receptor fusion protein comprises a tumor necrosis factor inhibitor. In certain embodiments, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991, each of which is incorporated herein by reference in its entirety) are expressed in accordance with systems and methods of the present invention (for review, see Naismith and Sprang, J. Inflamm. 47(1-2): 1-7, 1995-96, incorporated herein by reference in its entirety). According to some embodiments, a tumor necrosis factor inhibitor comprises a soluble TNF receptor. In certain embodiments, TNF inhibitors of the present invention are soluble forms of TNFRI and TNFRII. In certain embodiments, TNF inhibitors of the present invention are soluble TNF binding proteins. In certain embodiments, TNF inhibitors of the present invention are TNFR fusion proteins, e.g., TNFR-Ig or TNFR-Fc. As used herein, "etanercept," refers to a TNFR-Fc, which is a dimer of two molecules of the extracellular portion of the p75 TNF-alpha receptor, each molecule consisting of a 235 amino acid Fc portion of human IgG1. In accordance with the invention, cells expressing TNFR-Fc are grown in a cell culture at a reduced temperature and/or reduced pH to decrease the amount of misfolded protein and/or high molecular weight aggregates during the production of TNFR-Fc. In certain embodiments, cells expressing TNFR-Fc are grown in a cell culture at a reduced temperature and/or reduced pH to modulate glycosylation during the production of TNFR-Fc.

In another embodiment of the invention, the soluble receptor fusion protein is the sIL-13R. As used herein, soluble IL-13 receptor (sIL-13R) refers to a recombinant fusion protein which includes extracellular domain (ECD) of the human interleukin (IL)-13-alpha2 receptor and the Fc region of the human IgG1 heavy chain. sIL-13R is composed of two identical polypeptide chains (i.e., dimer of two polypeptide chains) which appear to be linked by intermolecular disulfide bonds. sIL-13R soluble receptor fusion protein and its uses are disclosed in U.S. Pat. No. 5,710,023, incorporated herein in its entirety by reference.

In some embodiments, the second polypeptide has less effector function than the effector function of an Fc region of a wild-type immunoglobulin heavy chain. Fc effector function includes, for example, Fc receptor binding, complement fixation and T cell-depleting activity (see, for example, U.S. Pat. No. 6,136,310). Methods for assaying T cell-depleting activity, Fc effector function, and antibody stability are known in the art. In one embodiment, the second polypeptide has low or no affinity for the Fc receptor. In an alternative embodiment, the second polypeptide has low or no affinity for complement protein C1q.

The fusion proteins, e.g., soluble receptor fusion proteins, may additionally include a linker sequence joining the soluble receptor or a fragment thereof to the second moiety. For example, the fusion protein can include a peptide linker, e.g., a peptide linker of about 2 to 20, more preferably about 5 to 10, amino acids in length.

In other embodiments, additional amino acid sequences can be added to the N- or C-terminus of the fusion protein to facilitate expression, detection and/or isolation or purification. For example, soluble receptor fusion protein may be linked to one or more additional moieties, e.g., GST, His6 tag, FLAG tag. For example, the fusion protein may additionally be linked to a GST fusion protein in which the fusion protein sequences are fused to the C-terminus of the GST (i.e., glutathione S-transferase) sequences. Such fusion proteins can facilitate the solubility, i.e., increase accurate folding, and thus improve purification of the fusion protein.

Methods of Protein Production in the Cell Culture

The terms "culture" and "cell culture" as used herein refer to a cell population that is contacted with a cell culture medium under conditions suitable to survival and/or growth of the cell population. As used herein, these terms may refer to the combination comprising the cell population (e.g., the animal cell culture) and the medium with which the population is in contact.

The cells used in the present invention may be recombinant host cells, e.g., eukaryotic host cells, i.e., cells transfected with an expression construct containing a nucleic acid that encodes a polypeptide of interest, including animal cells. The phrase "animal cells" encompasses invertebrate, nonmammalian vertebrate (e.g., avian, reptile and amphibian), and mammalian cells. Nonlimiting examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori* (silkworm/silk moth). In preferred embodiments the cell culture is a mammalian cell culture.

A number of mammalian cell lines are suitable host cells for recombinant expression of polypeptides of interest. Mammalian host cell lines include, for example, COS, PER.C6, TM4, VER0076, MDCK, BRL-3A, W138, Hep G2, MMT, MRC 5, FS4, CHO, 293T, A431, 3T3, CV-1, C3H10 T1/2, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2C12 cells, as well as transformed primate cell lines, hybridomas, normal diploid cells, and cell strains derived from in vitro culture of primary tissue and primary explants. Any eukaryotic cell that is capable of expressing the polypeptide of interest may be used in the disclosed methods. Numerous cell lines are available from commercial sources, such as the American Type Culture Collection (ATCC). In one embodiment of the invention, the cell culture, e.g., the large-scale cell culture, employs CHO cells.

Although in certain embodiments the cell culture comprises mammalian cells, one skilled in the art will understand that it is possible to recombinantly produce polypeptides of interest in lower eukaryotes such as yeast, or in prokaryotes such as bacteria. One skilled in the art would know that the culture conditions for yeast and bacterial cell cultures will differ from the culture conditions of animals cells, and will understand how these conditions will need to be adjusted in order to optimize cell growth and/or protein production.

Suitable bacterial strains include *Escherichia coli*, *Bacillus subtilis*, *Salmonella typhimurium*, or any bacterial strain capable of expressing the polypeptide of interest. Expression in bacteria may result in formation of inclusion bodies incorporating the recombinant protein. Thus, refolding of the recombinant protein may be required in order to produce active, or more active, material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment that allows correct formation of disulfide bonds (a redox system). General methods of refolding are known in the art and disclosed in, e.g., Kohno (1990) *Meth. Enzymol.* 185:187-95, EP 0433225, and U.S. Pat. No. 5,399,677.

Suitable yeast strains for polypeptide production include *Saccharomyces cerevisiae*, *Schizosaccharomyces pombe*, *Pichia pastoris*, *Kluyveromyces* strains, *Candida*, or any yeast strain capable of expressing polypeptide of interest.

The term "bioreactor" as used herein refers to any vessel used for the growth of a eukaryotic cell culture, e.g., an animal cell culture (e.g., a mammalian cell culture). The bioreactor can be of any size as long as it is useful for the culturing of cells, e.g., mammalian cells. Typically, the bioreactor will be at least 30 ml and may be at least 1, 10, 100, 250, 500, 1000, 2500, 5000, 8000, 10,000, 12,000 liters or more, or any intermediate volume. The internal conditions of the bioreactor, including but not limited to pH and temperature, are typically controlled during the culturing period. The term "production bioreactor" as used herein refers to the final bioreactor used in the production of the polypeptide or protein of interest. The volume of a large-scale cell culture production bioreactor is generally greater than about 100 ml, typically at least about 10 liters, and may be 500, 1000, 2500, 5000, 8000, 10,000, 12,000 liters or more, or any intermediate volume. A suitable bioreactor or production bioreactor may be composed of (i.e., constructed of) any material that is suitable for holding cell cultures suspended in media under the culture conditions of the present invention and is conducive to cell growth and viability, including glass, plastic or metal; the material(s) should not interfere with expression or stability of the produced product, e.g., a therapeutic protein product. One of ordinary skill in the art will be aware of, and will be able to choose, suitable bioreactors for use in practicing the present invention.

The terms "medium," "cell culture medium," and "culture medium" as used herein refer to a solution containing nutrients that nourish growing animal cells, e.g., mammalian cells, and can also refer to medium in combination with cells. The term "inoculation medium" refers to the medium that is used to form a cell culture. Inoculation medium may or may not differ in composition from the medium used during the rest of the cell growth phase. Typically, medium solutions provide, without limitation, essential and nonessential amino acids, vitamins, energy sources, lipids, and trace elements required by the cell for at least minimal growth and/or survival. The solution may also contain components that enhance growth and/or survival above the minimal rate, including hormones and growth factors. The solution is preferably formulated to a pH and salt concentration optimal for cell survival and proliferation. In at least one embodiment, the medium is a defined medium. Defined media are media in which all components have a known chemical structure. In other embodiments of the invention, the medium may contain an amino acid(s) derived from any source or method known in the art, including, but not limited to, an amino acid(s) derived either from single amino acid addition(s) or from a peptone or protein hydrolysate addition(s) (including animal or plant source(s)). In yet other embodiments of the invention, the medium used during the cell growth phase may contain concentrated medium, i.e., medium that contains higher concentration of nutrients than is normally necessary and normally provided to a growing culture. One skilled in the art will recognize which cell media, inoculation media, etc. is appropriate to culture a particular cell, e.g., animal cell (e.g., CHO cells), and the amount of glucose and other nutrients (e.g., glutamine, iron, trace D elements) or agents designed to control other culture variables (e.g., the amount of foaming, osmolality) that the medium should contain (see, e.g., Mather, J. P., et al. (1999) "Culture media, animal cells, large scale production," *Encyclopedia of Bioprocess Technology: Fermentation, Biocatalysis, and Bioseparation*, Vol. 2:777-85; U.S. Published Patent Application No. 2006/0121568; both of which are hereby incorporated by reference herein in their entireties). The present invention also contemplates variants of such known media, including, e.g., nutrient-enriched variants of such media. The term "cell density" as used herein refers to the number of cells present in a given volume of medium.

The term "viable cell density" as used herein refers to the number of live cells present in a given volume of medium under a given set of experimental conditions.

The term "cell viability" as used herein refers to the ability of cells in culture to survive under a given set of culture conditions or experimental variations. The term as used herein also refers to that portion of cells that are alive at a particular time in relation to the total number of cells, living and dead, in the culture at that time.

The terms "integrated viable cell density," "integrated viable cell number" or "IVC" as used herein refer to the average density of viable cells over the course of the culture multiplied by the amount of time the culture has run. When the amount of protein produced is proportional to the number of viable cells present over the course of the culture, integrated viable cell density is a useful tool for estimating the amount of protein produced over the course of the culture.

The methods of the present invention are applicable to cells grown in a batch culture, fed batch culture, perfusion culture, modified fed-batch culture (see U.S. Provisional Application No. 60/954,922), batch refeed culture, or any combination thereof.

The term "batch culture" as used herein refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. The provided components typically comprise nutritional supplements for the cells that have been depleted during the culturing process. A fed-batch culture is typically stopped at some point and the cells and/or components in the medium are harvested and optionally purified.

The term "perfusion culture" as used herein refers to a method of culturing cells in which additional fresh medium is provided, either continuously over some period of time or intermittently over some period of time, to the culture (subsequent to the beginning of the culture process), and simultaneously spent medium is removed. The fresh medium typically provides nutritional supplements for the cells that have been depleted during the culturing process. Polypeptide product, which may be present in the spent medium, is optionally purified. Perfusion also allows for removal of cellular waste products (flushing) from the cell culture growing in the bioreactor.

The term "modified fed-batch culture" as used herein refers to a method of culturing cells which combines both the fed-batch culture method and the perfusion culture method. The modified fed-batch culture method is described in U.S. Provisional Application No. 60/954,922, incorporated herein in its entirety by reference.

The invention can also be practiced with batch re-feed processes. It is believed that reduced pH will provide a better handle for reducing protein misfolding and/or aggregation and for modifying glycosylation in this type of cell culture.

In one embodiment of the present invention, the method comprises first inoculating the cell culture with the inoculation medium during the growth phase of the cell culture, and subsequently switching cells into the production phase, wherein the temperature and/or pH of the cell culture is adjusted to a reduced temperature and/or a reduced pH.

Growth phase, as used herein, refers to a stage in the cell culture wherein the cells are grown to achieve the cell density optimal for protein production.

In another embodiment, following growth phase, the cells may be switched into the production phase, which may occur at different temperature and/or different pH than the growth phase, for example, reduced temperature and/or reduced pH. In embodiments, the cell culture may be switched from growth phase to production phase one day after the inoculation. In other embodiments, the cell culture may be switched from growth phase to production phase five days after the inoculation. When shifting the cell culture from the growth to the production phase, the shift may be relatively gradual. Alternatively, the shift may be abrupt. With gradual change, the temperature and/or pH may be steadily adjusted, e.g., decreased. Alternatively, the temperature and/or pH may be adjusted by discrete intervals.

Production phase of the cell culture is a stage in the cell culture wherein the cells are grown under conditions optimal for producing the polypeptide of interest, e.g., a therapeutic protein. During the production phase, the reduced temperature and/or pH of the cell culture may be selected based on the temperature and/or pH at which the cell culture remains viable, at which high level of protein is produced, at which production and accumulation of metabolic waste products, e.g., lactic acid and ammonia, is minimized, at which the product quality of the protein has been appropriately controlled, and/or any combination of these or other factors deemed important by the practitioner.

In an alternative embodiment of the invention, the method of the invention comprises inoculating the cell culture at a reduced temperature and/or reduced pH, so no temperature or pH shift is necessary at the initiation of the production phase. A skilled artisan would know to monitor the temperature and the pH of the cell culture such that the temperature and the pH do not deviate from the established temperature and pH set points. For instance, a skilled artisan will know to use a base, e.g., sodium carbonate base, to prevent cultures from deviating below the set pH.

In the examples hereinbelow, the cell culture medium started at a pH above the target pH set point and no deliberate adjustment to pH set point occurred. However, the use of a pH adjustment during the course of the cell culture could also be included as would be understood by those of skill in the art. Similarly, initiating the culture at low temperature without an adjustment is also possible. For example, the process may be comprised of a production phase only.

"Reduced temperature," as used herein, refers to a temperature below the conventional temperature for cell growth (the temperature at which the cell are typically grown) for that type of cell. For example, in embodiments of the present invention, where the cells are mammalian cells, the cell culture in the production phase is preferably in a range of 24.0° C. to less than 30.0° C., and more preferably in a range of 27.0° C. to less than 30.0° C. For example, reduced temperature of the cell culture is 24.0° C., 24.5° C., 25.0° C., 25.5° C., 26.0° C., 26.5° C. 27.0° C., 27.5° C., 28.0° C., 28.5° C., 29.0° C., 29.5° C., 29.6° C., 29.7° C., 29.8° C., and 29.9° C. In the most preferred embodiment of the invention described herein, reduced temperature of the cell culture is a temperature of about 29.5° C. Reduced temperature for cells other than mammalian may be determined on a case by case basis by a person of ordinary skill in the art.

"Reduced pH," as used herein, refers to a pH set point below the conventional pH for cell growth (the pH at which the cells are typically grown) of that particular cell type. In embodiments of the present invention, where the cells are mammalian cells, reduced pH of the cell culture in the production phase is below 7.00. In embodiments of the invention, reduced pH of the cell culture is in a range of 6.50 to less than 7.00, preferably in a range of 6.80 to less than 7.00. For example, reduced pH of the cell culture is 6.80, 6.85, 6.90, 6.95, 6.96, 6.97, 6.98, and 6.99. In the most preferred embodiment of the invention, reduced pH of the cell culture is about 6.95. Reduced pH for cells other than mammalian may be determined on a case by case basis by a person of ordinary skill in the art.

A skilled artisan will understand that depending on the cell type of the cell culture, conventional temperature and pH (as distinguished from the reduced temperature and pH) will differ. For example, conventional temperature and pH for most mammalian cells, e.g., CHO cells, is above 30.0° C. (such as, for example, 37.0° C.) and above 7.00 (such as, for example, 7.20), respectively. A skilled artisan will also understand that because conventional temperature and pH for other cell types, e.g., insect cells, will differ from the conventional temperature for mammalian cells, the methods of the invention will utilize a different reduced temperature and a different reduced pH for such cells.

In certain embodiments of the present invention, the practitioner may find it beneficial or necessary to periodically monitor particular conditions of the growing cell culture. As nonlimiting examples, it may be beneficial or necessary to monitor, e.g., temperature, pH, dissolved oxygen, cell density, cell viability, integrated viable cell density, lactate levels, ammonium levels, glucose levels, glutamine levels, osmolality, titer of the expressed polypeptide, etc. Numerous techniques are well known to those of skill in the art for measuring such conditions/criteria. For example, cell density may be measured using a hemocytometer, an automated cell-counting device (e.g., a Coulter counter, Beckman Coulter Inc., Fullerton, Calif.), or cell-density examination (e.g., CEDEX®, Innovatis, Malvern, Pa.). Viable cell density may be determined by staining a culture sample with Trypan blue. Lactate, ammonium, glucose and glutamine levels, as well as dissolved oxygen and pH may be measured, e.g., with the BioProfile 400 Chemistry Analyzer (Nova Biomedical, Waltham, Mass.), which takes measurements of key nutrients, metabolites, and gases in cell culture media. Dissolved oxygen and pH may also be measured using, e.g., a blood gas analyzer (e.g., a Bayer Rapidlab 248 pH/blood gas analyzer (Bayer HealthCare LLC, East Walpole, Mass.)). Temperature, pH, and dissolved oxygen may also be measured by, e.g., various types of in-situ probes. Osmolality of the cell culture may be measured by, e.g., a freezing point osmometer. HPLC can be used to determine, e.g., the levels of lactate, ammonium, or the expressed polypeptide or protein. In one embodiment of the invention, the levels of expressed polypeptide can be determined by using, e.g., protein A HPLC. Alternatively, the level of the expressed polypeptide or protein can be determined by standard techniques such as Coomassie staining of SDS-PAGE gels, Western blotting, Bradford assays, Lowry assays, biuret assays, and UV absorbance. It may be necessary to monitor the posttranslational modifications of the expressed polypeptide or protein, e.g., glycosylation. It also may be beneficial to monitor other posttranslational modifications of the protein, e.g., phosphorylation, etc. In order to monitor certain cell culture conditions, it may be necessary to remove small aliquots of the culture for analysis. One of ordinary skill in the art will understand that such removal may potentially introduce contamination into the cell culture, and will take appropriate care to minimize the risk of such contamination.

In one embodiment of the invention, a practitioner will monitor integrated viable cell number at the reduced cell culture temperature and/or reduced pH. Preferably, growing cells at the reduced temperature and/or reduced pH reduces integrated viable cell density by 20%, more preferably less than 20% (e.g., 15%). In another embodiment of the invention, a practitioner will monitor cell viability at the reduced cell culture temperature and/or reduced pH. Preferably, growing cells at the reduced temperature and/or reduced pH reduces cell viabilities by less than 15%, more preferably by less than 5%.

Glucose is a primary source of energy for the cell culture. Significant deviations in glucose consumption in the cell culture could indicate a negative effect of cell culture conditions on the health of the cell culture. Thus, in a preferred embodiment of the invention, growing cells at the reduced temperature and/or reduced pH results in minimal change, e.g., reduction, in glucose consumption of the cell culture.

Glutamine is an alternative source of energy for the cell culture, and is an important source of nitrogen for various molecules, e.g., amino acids, in the cell culture. Thus, in a preferred embodiment of the invention, growing cells at the reduced temperature and/or reduced pH results in a minimal change, e.g., reduction, in the glutamine consumption of the cell culture.

In another embodiment of the invention, a practitioner will monitor waste product production, e.g., lactate and ammonia production, in the cell culture. Thus, in a preferred embodiment of the invention, growing cells at the reduced temperature and/or pH results in a minimal change, e.g., increase, in production of lactate and ammonia. In some embodiments of the invention, growing cells at a reduced temperature an/or pH can minimize lactate and ammonia production.

Additionally, in a preferred embodiment of the present invention, growing cells at a reduced temperature and/or pH results in minimal reduction in cumulative average productivity and product titer. The term "titer" as used herein refers to the total amount of polypeptide of interest, e.g., a glycoprotein of interest, produced by a cell culture (e.g., an animal cell culture), divided by a given amount of medium volume; thus "titer" refers to a concentration. Titer is typically expressed in units of milligrams of polypeptide per liter of medium. Preferably, any reduction in cell productivity and product titer experienced in the cell culture is offset by decreased production of aggregated or misfolded protein product, e.g., decreased production of HMWA.

As used herein, the term "aggregated protein" refers to the protein groupings, i.e., high molecular weight aggregates, that produce nonfunctional, sub-optimal or undesired protein product. The term "misfolded protein" refers to an improperly folded protein, often a protein that can no longer display normal biological activity, e.g., normal enzymatic activity. One skilled in the art will know that protein aggregates may comprise either or both correctly folded and/or misfolded proteins. Aggregated or misfolded proteins are commonly formed in overexpressing cell culture, e.g., a cell culture overexpressing a protein of interest, e.g., a glycoprotein of interest. For instance, aggregation can be caused either by nonspecific hydrophobic interactions of unfolded polypeptide chains or by interaction of folding intermediates. In one embodiment of the invention, growing cells at the reduced temperature and/or reduced pH results in at least 50% reduction in protein misfolding/aggregation, preferably about 60% reduction in protein misfolding/aggregation. One skilled in the art will know the techniques required to monitor protein aggregation/misfolding, e.g., hydrophobic interaction HPLC (HIC-HPLC).

The term "high molecular weight aggregate" (HMWA) refers to undesirable byproduct of protein production which results from association between at least two proteins. "High molecular weight aggregate" may be an association between at least two of the same proteins and/or association between the protein of interest and other proteins found in the cell culture, e.g., host cell proteins. The association may arise by any method including, but not limited to, covalent, noncovalent, disulfide, and/or nonreducible crosslinking. One skilled in the art will understand that when a protein is active in a multimer form (e.g., a dimer form), i.e., when more than one polypeptide chain is required for protein activity, the term "high molecular weight aggregates" will refer to an association between two or more of such multimer forms. In one embodiment of the invention, a protein that is active in a multimer form is a receptor, e.g., a cytokine receptor (e.g., sIL-13R). In one embodiment, growing cells at a reduced temperature and/or pH results in at least about a 10% reduction, preferably about a 40% reduction, more preferably about a 50% reduction, and even more preferably about an 80% or more reduction in high molecular weight aggregates, or any intermediate values. One skilled in the art will know the techniques required to monitor production of high molecular weight aggregates, e.g., size-exclusion high performance liquid chromatography (SEC-HPLC).

In another aspect of the invention, temperature and/or pH in a cell culture are used to change protein glycosylation, e.g., protein sialylation, to a predetermined level. For example, decreasing pH and/or temperature of the cell culture may lead to the decrease in both N- and O-linked glycosylation, e.g., decrease in N-glycan sialylation). Change in protein glycosylation (e.g., sialylation) can affect stability, enzymatic activity, circulation lifetime, and immunogenicity of the therapeutic protein. One skilled in the art may monitor the degree of glycosylation (e.g., sialylation) to ensure that the changing temperature and/or pH achieves a desired type and level of protein glycosylation. Chromatographic techniques, e.g., Normal Phase Chromatography (NPC), may be used to monitor protein glycosylation of the protein product.

At the end of the production phase, the cells are harvested and the polypeptide of interest is collected and purified. Preferably, at the end of the production phase, the polypeptide of interest displays reduced misfolding and/or aggregation, while retaining an acceptable glycosylation pattern. In one embodiment of the invention, the polypeptide of interest at the end of the production process is in a soluble form (e.g., the polypeptide of interest is a soluble receptor, e.g., a soluble cytokine receptor). Such soluble forms of the polypeptide can be purified from conditioned media.

Membrane-bound forms of the polypeptide can be purified by preparing a total membrane fraction from the expressing cells and extracting the membranes with a nonionic detergent such as TRITON® X-100 (EMD Biosciences, San Diego, Calif.). Cytosolic or nuclear proteins may be prepared by lysing the host cells (via mechanical force, Parr-bomb, sonication, detergent, etc.), removing the cell membrane fraction by centrifugation, and retaining the supernatant.

The polypeptide can be purified using other methods known to those skilled in the art. For example, a polypeptide produced by the disclosed methods can be concentrated using a commercially available protein concentration filter, for example, an AMICON® or PELLICON® ultrafiltration unit (Millipore, Billerica, Mass.). Following the concentration step, the concentrate can be applied to a purification matrix such as a gel filtration medium. Alternatively, an anion exchange resin (e.g., a MonoQ column, Amersham Biosciences, Piscataway, N.J.) may be employed; such resin contains a matrix or substrate having pendant diethylaminoethyl (DEAE) or polyethylenimine (PEI) groups. The matrices used for purification can be acrylamide, agarose, dextran, cellulose or other types commonly employed in protein purification. Alternatively, a cation exchange step may be used for purification of proteins. Suitable cation exchangers include various insoluble matrices comprising sulfopropyl or carboxymethyl groups (e.g., S-SEPHAROSE® columns, Sigma-Aldrich, St. Louis, Mo.).

The purification of the polypeptide from the culture supernatant may also include one or more column steps over affinity resins, such as concanavalin A-agarose, AF-HEPARIN650, heparin-TOYOPEARL® or Cibacron blue 3GA SEPHAROSE® (Tosoh Biosciences, San Francisco, Calif.); hydrophobic interaction chromatography columns using such resins as phenyl ether, butyl ether, or propyl ether; or immunoaffinity columns using antibodies to the labeled protein. Finally, one or more HPLC steps employing hydrophobic HPLC media, e.g., silica gel having pendant methyl or other aliphatic groups (e.g., Ni-NTA columns), can be employed to further purify the protein. Alternatively, the polypeptides may be recombinantly expressed in a form that facilitates purification. For example, the polypeptides may be expressed as a fusion with proteins such as maltose-binding protein (MBP), glutathione-S-transferase (GST), or thioredoxin (TRX); kits for expression and purification of such fusion proteins are commercially available from New England BioLabs (Beverly, Mass.), Pharmacia (Piscataway, N.J.), and Invitrogen (Carlsbad, Calif.), respectively. The proteins can also be tagged with a small epitope (e.g., His, myc or Flag tags) and subsequently identified or purified using a specific antibody to the chosen epitope. Antibodies to common epitopes are available from numerous commercial sources. Some or all of the foregoing purification steps in various combinations or with other known methods, can be employed to purify a polypeptide of interest, e.g., a therapeutic protein, produced by the methods of the present invention.

Pharmaceutical Compositions

In certain embodiments of the invention, proteins produced according to one or more methods of the present invention can be useful in the preparation of pharmaceuticals. Proteins produced according to one or more methods of the present invention may be administered to a subject or may first be formulated for delivery by any available route including, but not limited to, e.g., parenteral (e.g., intravenous), intradermal, subcutaneous, oral, nasal, bronchial, ophthalmic, transdermal (topical), transmucosal, rectal, and vaginal routes. Inventive pharmaceutical compositions typically include a purified protein expressed from a mammalian cell line, a delivery agent (e.g., a cationic polymer, peptide molecular transporter, surfactant, etc., as described above) in combination with a pharmaceutically acceptable carrier. As used herein the language "pharmaceutically acceptable carrier" includes nontoxic materials that do not interfere with the effectiveness of the biological activity of the active ingredient(s), e.g., solvents, dispersion media, coatings, antibacterial and antifungal agents, isotonic and absorption delaying agents, and the like, compatible with pharmaceutical administration. The characteristics of the carrier will depend on the route of administration. Supplementary active compounds can also be incorporated into the compositions.

A pharmaceutical composition is formulated to be compatible with its intended route of administration. When the therapeutic protein produced according to one or more methods of the present invention is administered in an oral form, the pharmaceutical composition will be in the form of a tablet, capsule, powder, solution or elixir. When administered in tablet form, the pharmaceutical composition of the invention may additionally contain a solid carrier such as a gelatin or an adjuvant. The tablet, capsule, and powder will contain from about 5 to 95% binding agent, and preferably from about 25 to 90% binding agent. When administered in liquid form, a liquid carrier such as water, petroleum, oils of animal or plant origin, such as sesame oil, peanut oil (taking into consideration the occurrence of allergic reactions in the population), mineral oil, or soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition contains from about 0.5 to 90% by weight of the binding agent, and preferably from about 1 to 50% by weight of the binding agent.

When the therapeutic protein produced according to one or more methods of the present invention is administered by intravenous, cutaneous or subcutaneous injection, the therapeutic protein will be in the form of a pyrogen-free, parenterally acceptable aqueous solution. The preparation of such parenterally acceptable protein solutions, having due regard to pH, isotonicity, stability, and the like, is within the skill of those in the art. A preferred pharmaceutical composition for intravenous, cutaneous, or subcutaneous injection should contain, in addition to the therapeutic protein, an isotonic vehicle such as sodium chloride injection, Ringer's injection, dextrose injection, dextrose and sodium chloride injection, lactated Ringer's injection, or other vehicle as known in the art. The pharmaceutical composition of the present invention may also contain stabilizers, preservatives, buffers, antioxidants, or other additive known to those of skill in the art.

Additional formulation of the pharmaceutical compositions comprising the therapeutic proteins produced by one or more methods of the present invention will be known to those skilled in the art. One of ordinary skill in the art will also be aware of unit dosage formulations appropriate for proteins produced according to the present invention.

The entire contents of all references, patents, and patent applications cited throughout this application are hereby incorporated by reference herein.

EXAMPLES

The Examples which follow are set forth to aid in the understanding of the invention but are not intended to, and should not be construed to, limit the scope of the invention in any way. The Examples do not include detailed descriptions of conventional methods, e.g., cloning, transfection, and basic aspects of methods for overexpressing proteins in cell lines. Such methods are well known to those of ordinary skill in the art.

Example 1

TNFR-Fc Protein Production

Example 1.1: Effects of Reduced Temperature on Cell Culture Performance of Recombinant CHO Cells and on Product Quality of TNFR-Fc Fusion Protein Example 1.1.1: Materials and Methods Chinese Hamster Ovary (CHO) cells overexpressing recombinant glycoprotein TNFR-Fc were inoculated at identical concentrations and conditions in four separate bench-scale bioreactors at 37.0° C. Cells were grown in a fed-batch culture for one day, followed by a temperature-shift to either 30.0° C., 29.0° C., 28.0° C., or 27.0° C. The initial pH set point lower limit of the culture was 7.00. A cell sample was removed from the culture each day to measure various conditions of the cells culture, e.g., integrated viable cell numbers, cell viabilities, residual glucose profile, residual glutamine profile, lactate and ammonia concentrations, cumulative average cell productivity (Qp), product titer, levels of misfolded/aggregated product, levels of high molecular weight aggregates, levels of sialylation, and pH.

Integrated viable cell numbers (IVC) were calculated by measuring cell density using cell-density examination (e.g., CEDEX®, Innovatis, Malvern, Pa.) and were normalized to the average harvest day IVC. The average harvest day IVC was determined by calculating the arithmetic mean of the harvest day (e.g., day 10) integrated viable cell density for the all experimental conditions tested. All individual IVC values were then scaled to the average harvest IVC to generate normalized values.

Cell viabilities were measured by staining with Trypan blue using cell-density examination (e.g., CEDEX®, Innovatis, Malvern, Pa.). Additionally, the residual glucose profile and the residual glutamine profile in the cell culture were measured using the BioProfile Chemistry Analyzer (Nova Biomedical, Waltham, Mass.). Concentrations of the waste products, lactate and ammonia, were measured using the BioProfile Chemistry Analyzer (Nova Biomedical, Waltham, Mass.).

Cumulative average cell productivity (Qp) and product titer were measured using protein A HPLC and were normalized to the average harvest day cumulative average Qp and titer. The average harvest day titer was determined by calculating the arithmetic mean of the harvest day (e.g., day 10) titer for all experimental conditions tested. All individual titer values were then scaled to the average harvest day titer to generate normalized values. The average harvest day cumulative average Qp was determined by calculating the arithmetic mean of the harvest day cumulative average Qp for all experimental conditions tested. All individual values were then scaled to the average harvest day titer to generate normalized values.

Levels of misfolded/aggregated product were measured using HIC-HPLC, and levels of high molecular weight aggregates were measured using SEC-HPLC. Levels of total and N-linked glycan sialylation were measured by subjecting 2-aminobenzamide-(2-AB)-labeled protein glycoforms to Normal Phase Chromatography (NPC). The amount of total sialylation (N- and O-linked) was defined as the percentage relative to the amount of total sialylation of reference material, i.e., TNFR-Fc aliquot with known and preferable sialylation pattern. pH of the cell culture was determined by an off-line measurement via blood gas analyzer (Bayer Rapidlab 248 pH/blood gas analyzer (Bayer Healthcare LLC, East Walpole, Mass.)).

Example 1.1.2: Results

Figure 1A:
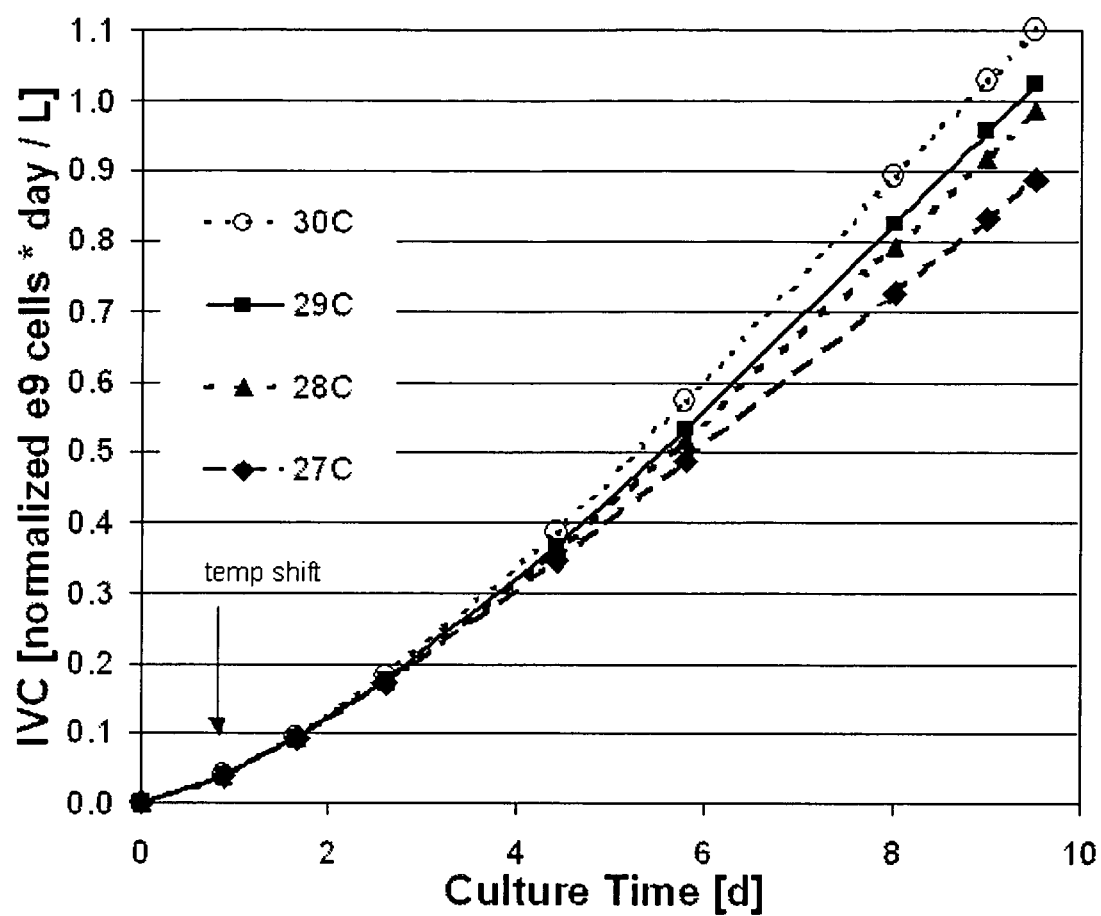
FIG. 1A represents integrated viable cell numbers (Y-axis; IVC [normalized $e^9$ cells*day/L]), normalized to average harvest day IVC, of CHO cells transfected with TNFR-Fc grown either at 27.0° C. [♦], 28.0° C. [▲], 29.0° C. [■], or 30.0° C. [○] over time (X-axis; culture time in days [d])
Figure 1B:
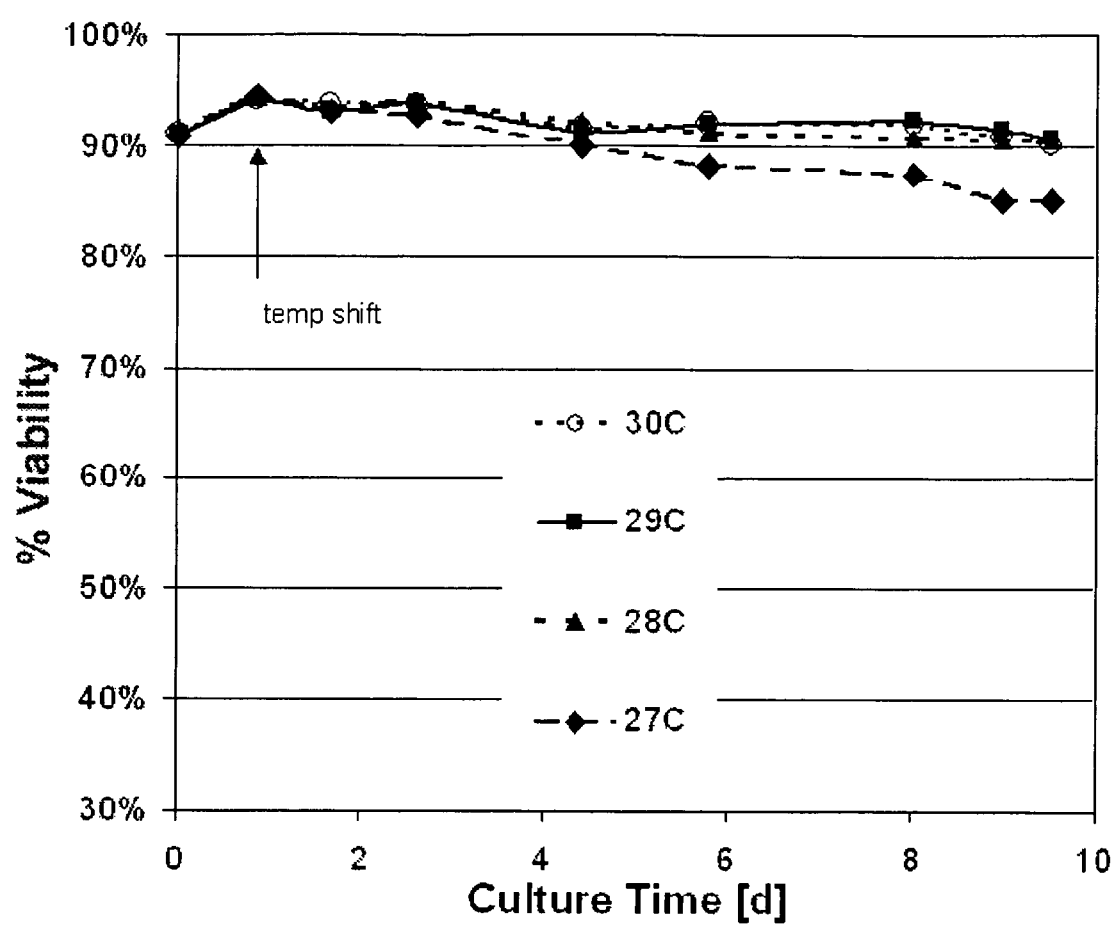
FIG. 1B represents cell viability (Y-axis) of the same cells over time (X-axis; culture time [d]).

Growing cells at a reduced temperature had minimal effects on IVC number. Specifically, lower operating temperatures resulted in a lower final IVC number; however, the effect of reducing cell culture temperature to 27° C. was minor—only about a 20% decrease in the IVC number was observed (FIG. 1A) Cell viabilities were not greatly affected by the decrease in temperature; the lowest temperature condition (i.e., 27° C.) had 5% lower harvest day viability (FIG. 1B).

Figure 2A:
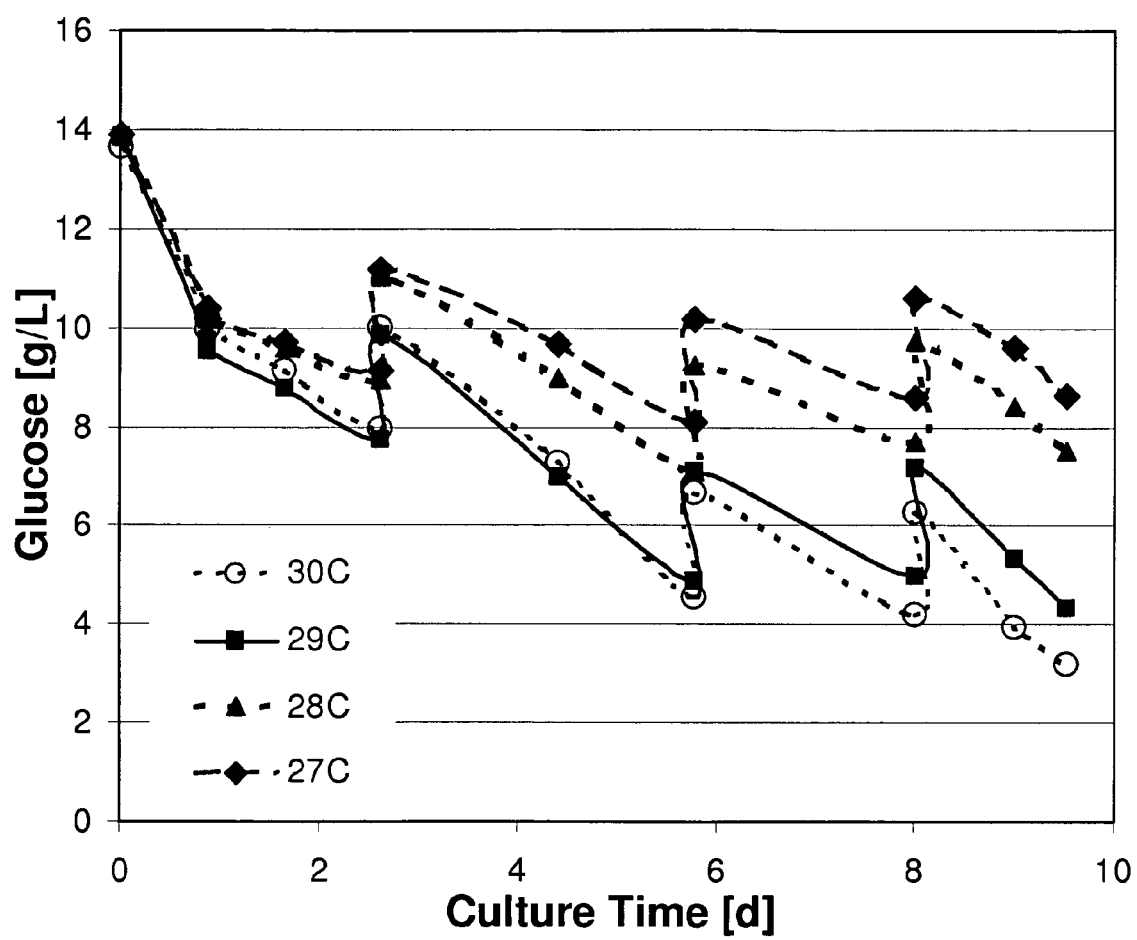
FIG. 2A represents the residual glucose profile (Y-axis; glucose [g/L]) in the cell culture of CHO cells transfected with TNFR-Fc grown either at 27.0° C. [♦], 28.0° C. [▲], 29.0° C. [■], or 30.0° C. [○] over time (X-axis; culture time [d])
Figure 2B:
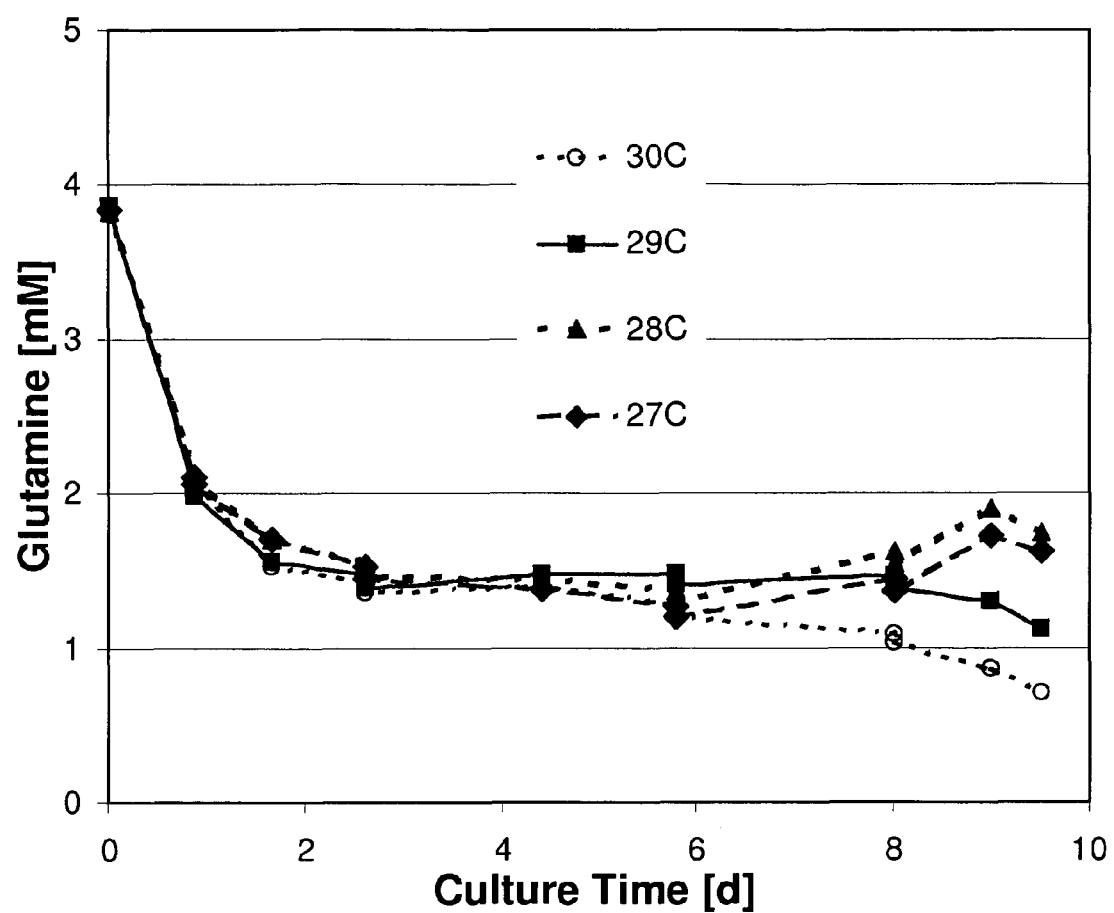
FIG. 2B represents the glutamine profile (Y-axis; glutamine [mM]) of the same cells over time (X-axis; culture time [d]).

Additionally, reduced operating temperatures resulted in a higher residual glucose profile, which indicated lower glucose consumption of the cell culture (FIG. 2A); however glutamine profiles were not significantly altered by reduced temperatures (FIG. 2B).

Figure 3A:
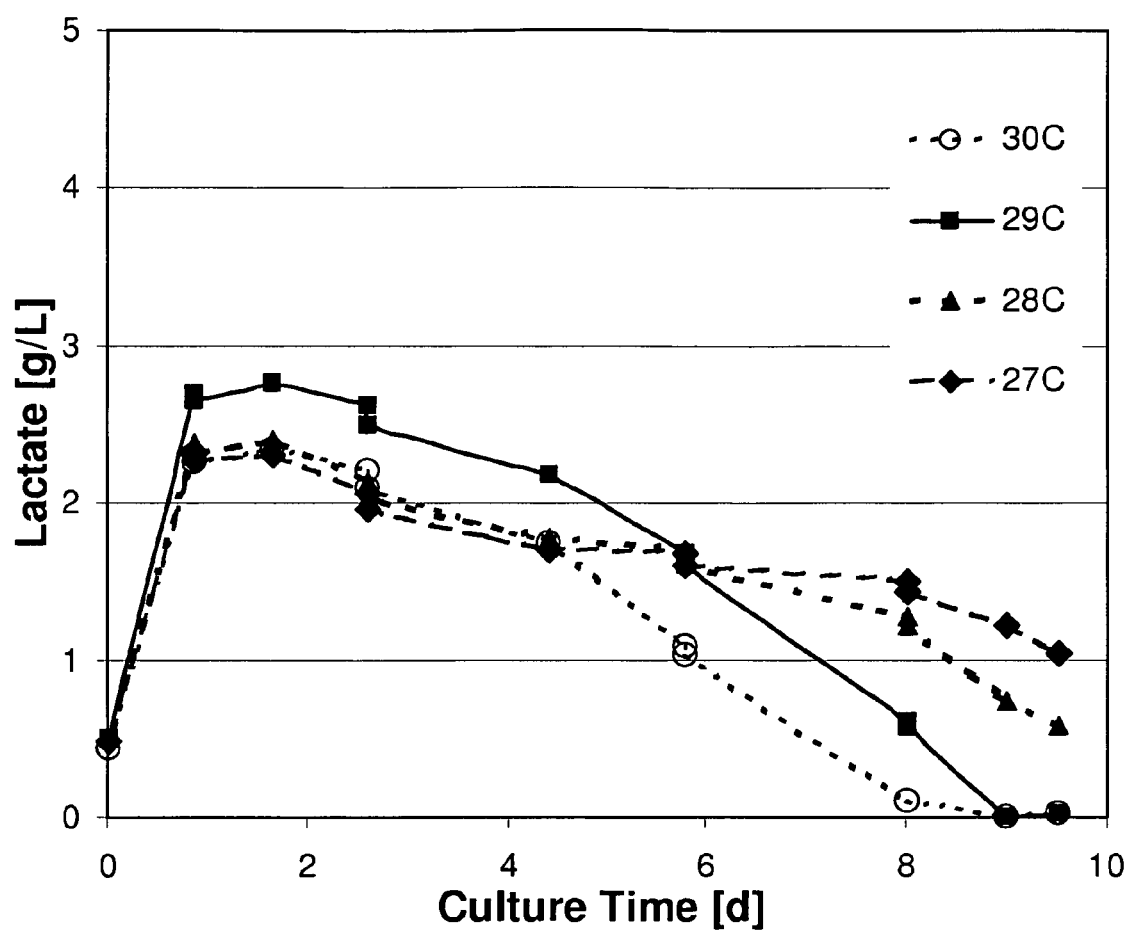
FIG. 3A represents lactate concentration in the media (Y-axis; lactate [g/L]) of the cell culture of CHO cells transfected with TNFR-Fc grown either at 27.0° C. [♦], 28.0° C. [▲], 29.0° C. [■], or 30.0° C. [○] over time (X-axis; culture time [d])
Figure 3B:
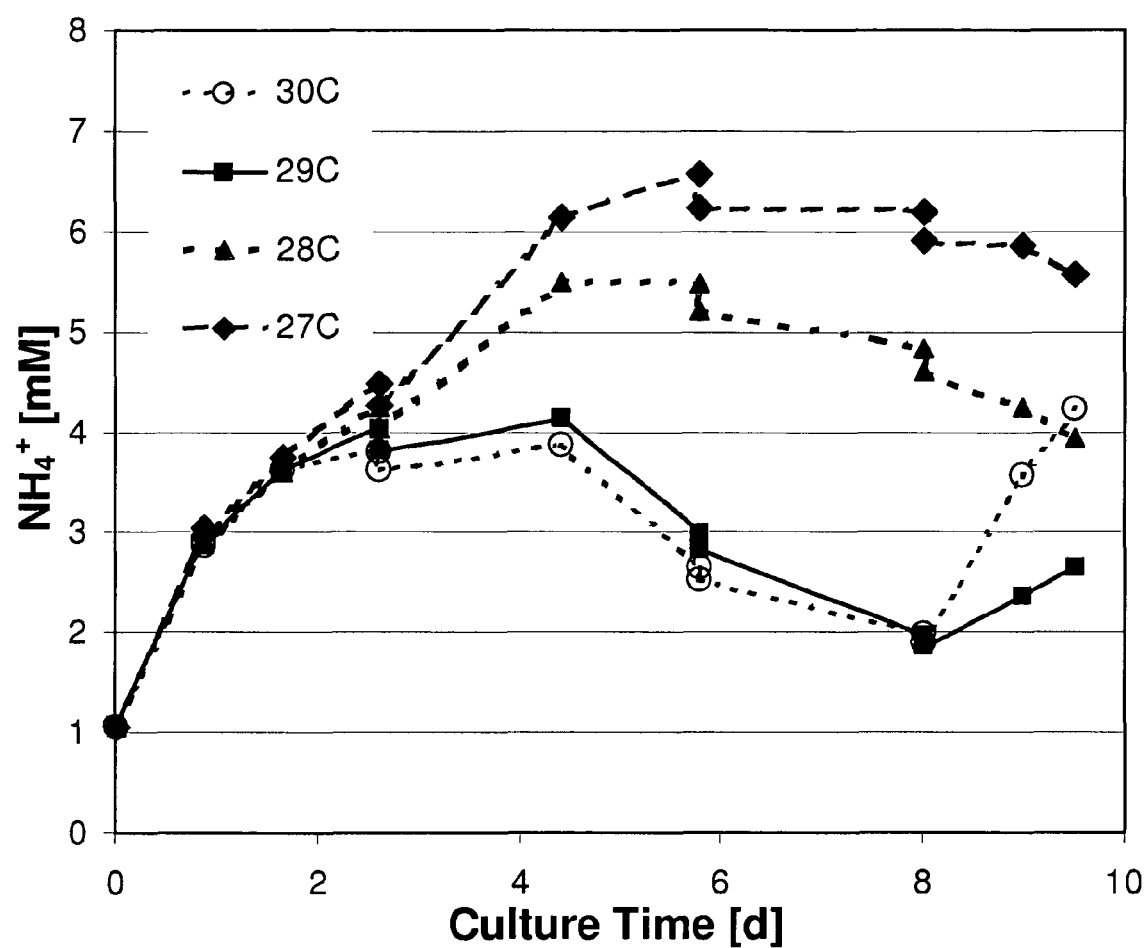
FIG. 3B represents the ammonium profile (Y-axis; $NH_4^+$ [mM]) of the same cells over time (X-axis; culture time [d]).
Figure 4A:
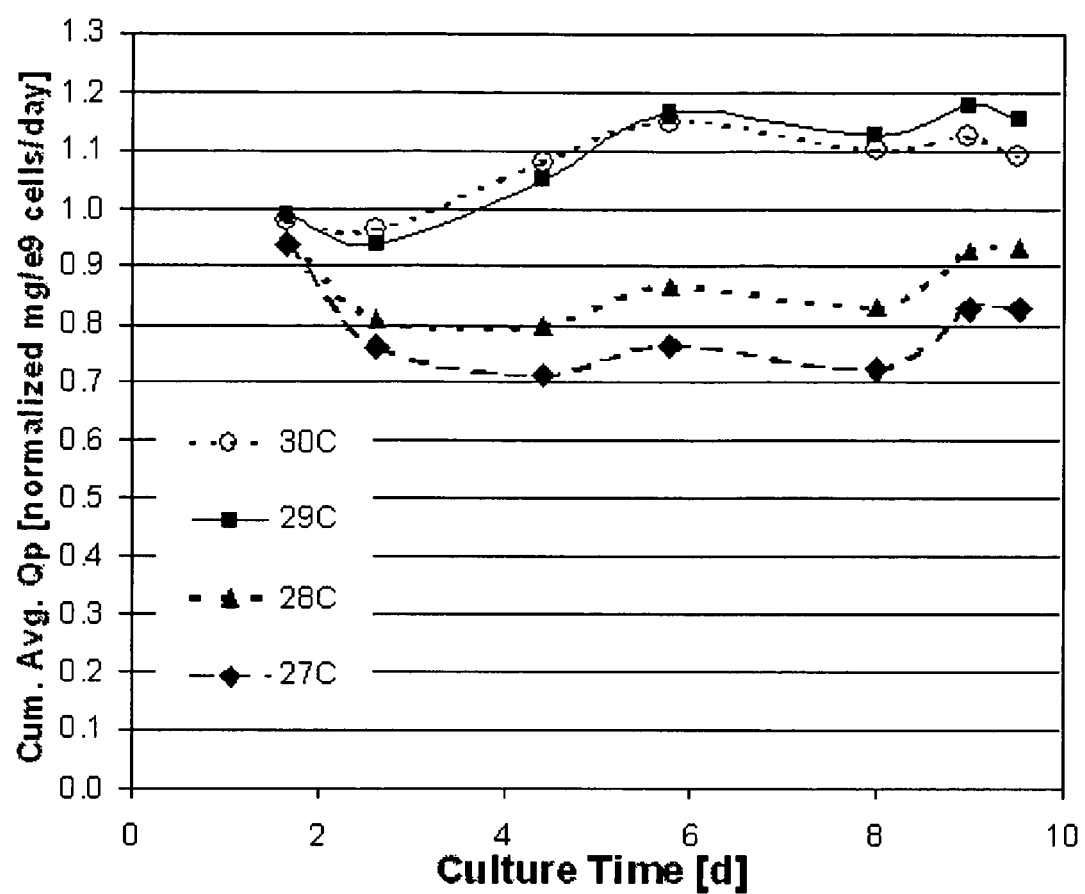
Figure 4B:
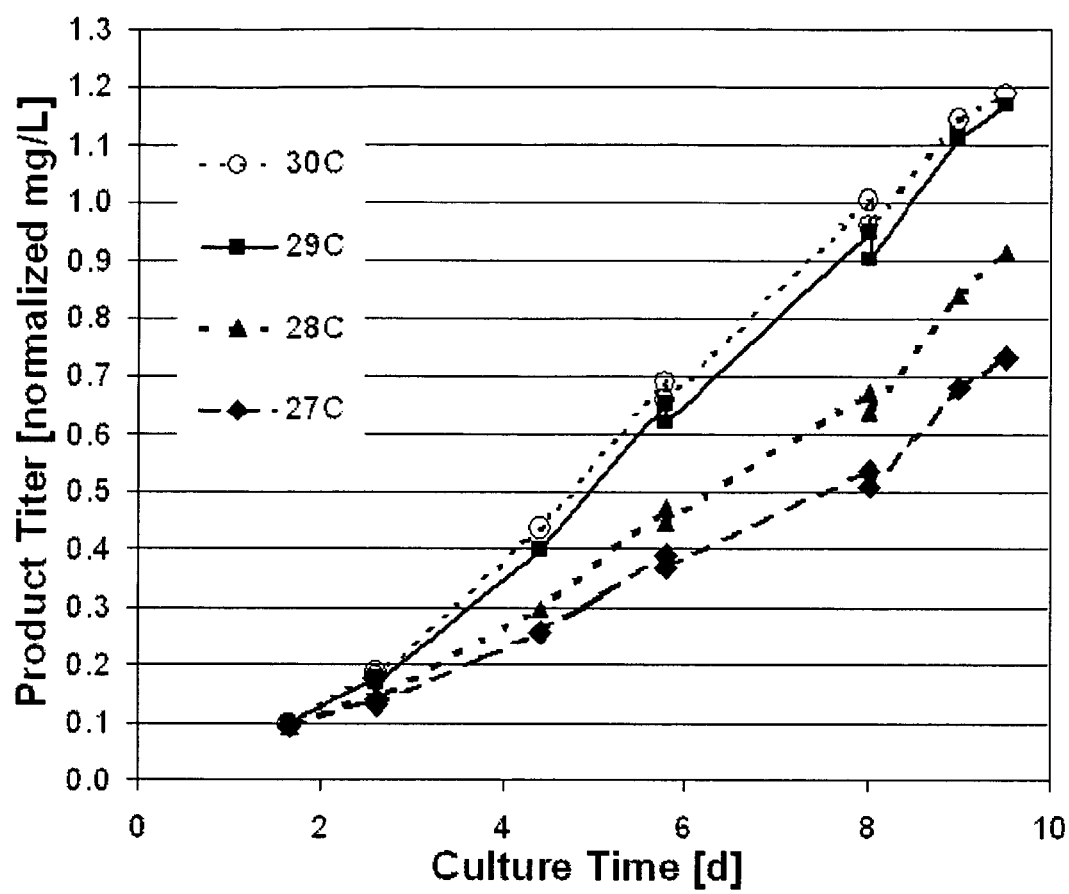
FIG. 4B represents TNFR-Fc titer (X-axis; product titer [normalized mg/L]), normalized to average harvest day titer, of the same cells over time (culture time [d]).

In some cases, late in the cell culture, lactic acid and ammonia may also be consumed by the cell culture. The cessation of the production of lactic acid and ammonia or the consumption of lactic acid and ammonia promote cell viability, cell productivity, and can have an effect of increasing polypeptide product titer. Growing cells at the reduced temperature had an effect of altering the net consumption of lactate in the later half of the fed-batch culture (FIG. 3A). Reduced temperatures also resulted in higher ammonia production (FIG. 3B). Reduced temperatures resulted in lower cell-specific productivities (lower Qp) (FIG. 4A) and lower product titer (FIG. 4B). Lower product titer is the result of lower cell specific productivity and lower integrated viable cell number. However, lower product titer and cell productivity was offset by a significantly decreased proportion of misfolded and aggregated product (FIG. 5A). Moreover, reducing temperature of the cell culture significantly decreased proportion of the high molecular weight aggregates in the cell culture (FIG. 5B). Therefore, reducing temperature resulted in improved TNFR-Fc protein product.

This decrease in temperature correlated with the decrease in total product sialylation (both N- and O-linked sialylation) (FIG. 6A). In fact, there was a direct relationship between reducing cell culture temperature and reducing the proportion of sialylated N-linked glycans (FIG. 6B), indicating that the production temperature must be chosen to balance the beneficial effect of reducing HMWA and protein misfolding and the unfavorable effect of reducing glycosylation. For instance, growing cells at a reduced temperature of 29.5° C. significantly reduced concentration of both misfolded and aggregated TNFR-Fc, while having minimal effects on TNFR-Fc glycosylation.

Differences in the net consumption of lactate between the cell cultures grown at different temperatures led to a difference in pH of the cell culture at the time of harvest (FIG. 7). This is due to the fact that larger net consumption of lactate (lactic acid) led to a larger rise in culture pH since acid was being removed from the environment.

Example 1.2: Effects of Reduced pH on Cell Culture Performance of Recombinant CHO Cells and on Product Quality of TNFR-Fc Fusion Protein Example 1.2.1: Materials and Methods CHO cells overexpressing recombinant glycoprotein TNFR-Fc were inoculated at identical concentrations at 37.0° C. and at pH set point of either 7.20, 7.10, 7.00, 6.90 or 6.80. Addition of sodium carbonate base was utilized to prevent cultures from deviating below the set point pH. No pH control was utilized above the set point pH. Bioreactors were temperature-shifted to 30.0° C. on day 1 (one day post inoculation, i.e., one day after the start of the experiment). Various conditions of the cell culture were measured as described in Example 1.1.1.

Example 1.2.2: Results

Growing cells at pH set points of 0.2 pH units away from pH 7.00 led to slightly decreased IVC; specifically, growing cells at pH of 6.80 led to about a 15% decrease in IVC compared to cells grown at pH of 7.00 (FIG. 8A). Additionally, growing cells at pH of 7.20 led to lower cell viability (FIG. 8B).

Additionally, lower operating pH set points resulted in lower glucose consumption (FIG. 9A). Glutamine profiles were not significantly altered by growing cells at pH set points of 6.80 to 7.10 (FIG. 9B).

Not surprisingly, higher operating pH set points led to higher production of lactate (FIG. 10A). At pH set point of 6.80, net consumption of lactate in the later half of the fed-batch did not occur. Lower operating pH set points resulted in higher ammonia production (FIG. 10B).

Differences in the net consumption of lactate in the later half of the experiment led to deviation of the pH of cultures from the operating pH set point, as only base, and not acid, addition was utilized to maintain pH (FIG. 11A). As a result of the differences in the pH set points, lactate profiles, and titrant additions, osmolarity also differed between the pH conditions (FIG. 11B).

Operating cultures at pH set points of 0.2 pH units away from pH 7.00 led to slightly lower cell-specific productivities (i.e., Qp) (FIG. 12A). Utilizing a pH set point of 6.80 or 7.20 resulted in lower product titers due to both lower cell-specific productivity and lower integrated viable cell numbers (FIG. 12B).

However, lower operating pH set points resulted in decreased product misfolding and aggregation (FIG. 13A). Additionally, significant reduction in the proportion of high molecular weight aggregates was observed at lower pH set points (FIG. 13B).

Lower operating pH set points resulted in lower total sialylation (both N- and O-linked glycans) (FIG. 14A), as well as a lower proportion of N-linked glycan sialylation (FIG. 14B). Because the amount of total sialylation (N- and O-linked) was defined as the percentage relative to the amount of total sialylation of reference material, any values below 100% represented reduction in total sialylation and values above 100% represented increase in total sialylation. The pattern of glycosylation can be depicted as the profile of glycans of the glycoprotein (FIG. 15). Growing cells at the reduced pH resulted in a significant alteration of the overall glycosylation profile (FIG. 16). While no new glycoforms were detected at the reduced pH, ratios of glycoforms present were significantly altered; growing cells at the reduced pH resulted in reduction of complex di- and mono-sialylated glycoforms. Because of the potentially unfavorable effect of the reduced pH on protein glycosylation, pH of the cell culture must be chosen in such as way that the detrimental effects on protein glycosylation are balanced by the beneficial effects on reduction of misfolded and/or aggregated proteins. For instance, growing cells at a reduced pH of 6.95 has significantly reduced the proportion of misfolded and aggregated TNFR-Fc protein, while having minimal effects on glycosylation of TNFR-Fc.

Example 1.3: Discussion

These studies demonstrate that within a temperature range of 27.0° C. to 30.0° C. or within a pH set point range of 6.80 to 7.20, cell growth and specific productivity of the cell culture can be significantly affected. However, while altering the temperature by as little as 1-2° C. and the pH set points by as little as 0.1-0.2, does not significantly affect cell growth and specific productivity, a significant (favorable) difference can be observed in protein folding and protein aggregation. Thus, small differences in cell culture conditions that do not significantly affect cell growth, viability or productivity, may significantly alter product quality, e.g., reduce protein folding and protein aggregation or affect glycosylation.

Example 2

Effects of Temperature on sIL-13R Production and Evaluation of a New sIL-13R Producing Cell Line Example 2.1: Materials and Methods Stably transfected Chinese Hamster Ovary (CHO) cells overexpressing recombinant glycoprotein sIL-13R were seeded in Applikon bioreactors at $3\times10^5$ cells/mL in an inoculation medium with Antifoam (Dow Corning Corporation, Midland, Mich.). Additional Antifoam was added as required. A concentrated nutrient medium was used as a feed medium. The pH set point lower limit was 6.80. The $dO_2$ set point was 23% utilizing 7% $CO_2$/93% air sparge gas, while agitation was 200 rpm. Bioreactors were temperature-shifted from 37.0° C. on day 5. The production phase temperature was either 37.0° C., 33.0° C., 32.0° C., 28.0° C., or room temperature (RT; about 24.0° C.). Feeding schedules for experimental conditions are summarized in Table 1. Feed volumes are listed as percentage of culture volume in bioreactor. The temperature shift for cell cultures occurred at about $6\times10^6$ cells/mL.

TABLE 1

Bioreactor Feed Schedules

| Experimental Condition: | 37.0° C. | 33.0° C. | 32.0° C. | 31.0° C. | 29.0° C. | RT |
|---|---|---|---|---|---|---|
| DAY | | | | | | |
| 3 | 10.2% | 10.2% | 10.2% | 10.2% | 10.2% | 10.2% |
| 5 | 5% | 5% | 5% | 5% | 5% | 5% |
| 6 | 5% | | | | | |
| 7 | 10.2% | 5% | 5% | 5% | 5% | 5% |
| 9 | 10.2% | 5% | 5% | 5% | 5% | 5% |
| 11 | 5% | 5% | 5% | 5% | 5% | 5% |
| 13 | 5% | | 5% | 5% | 5% | 5% |
| 16 | | | 5% | 5% | 5% | 5% |

Example 2.2. Results

Figure 17A:
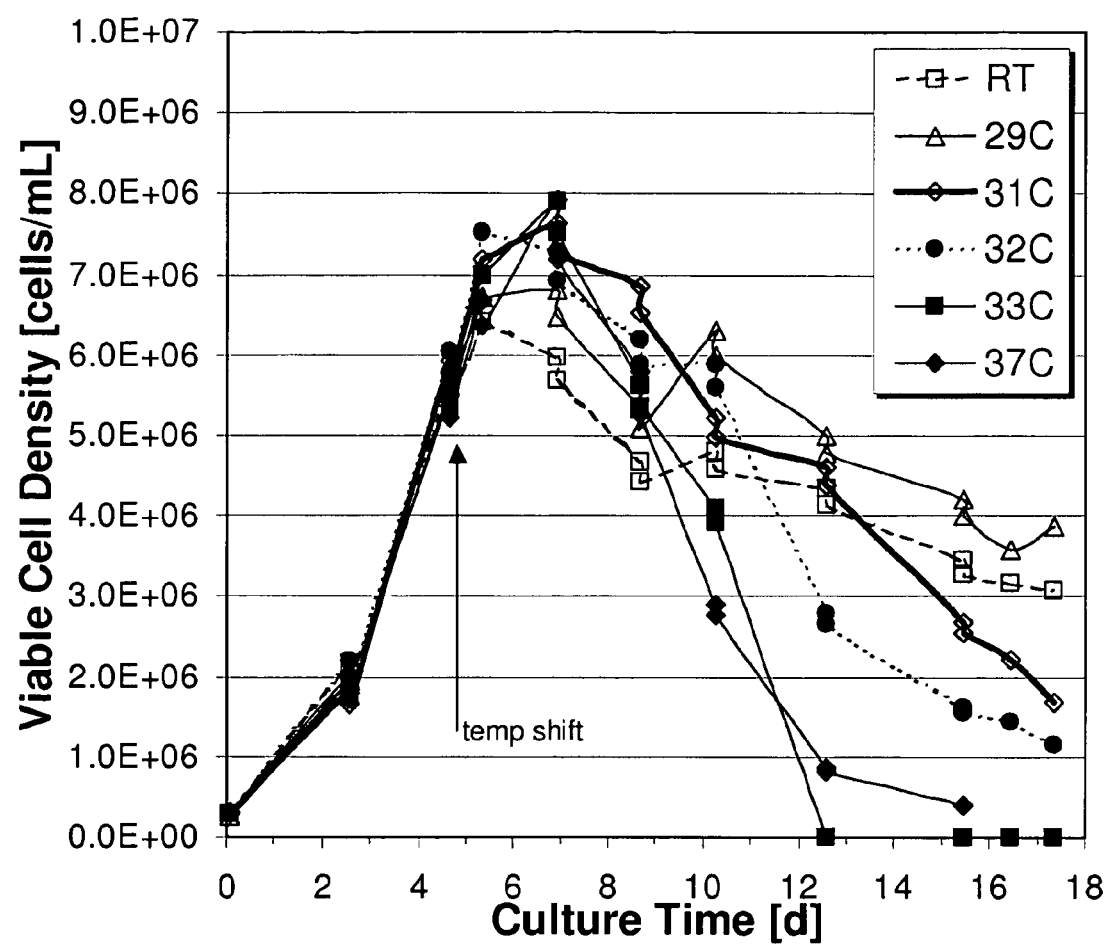
Figure 17B:
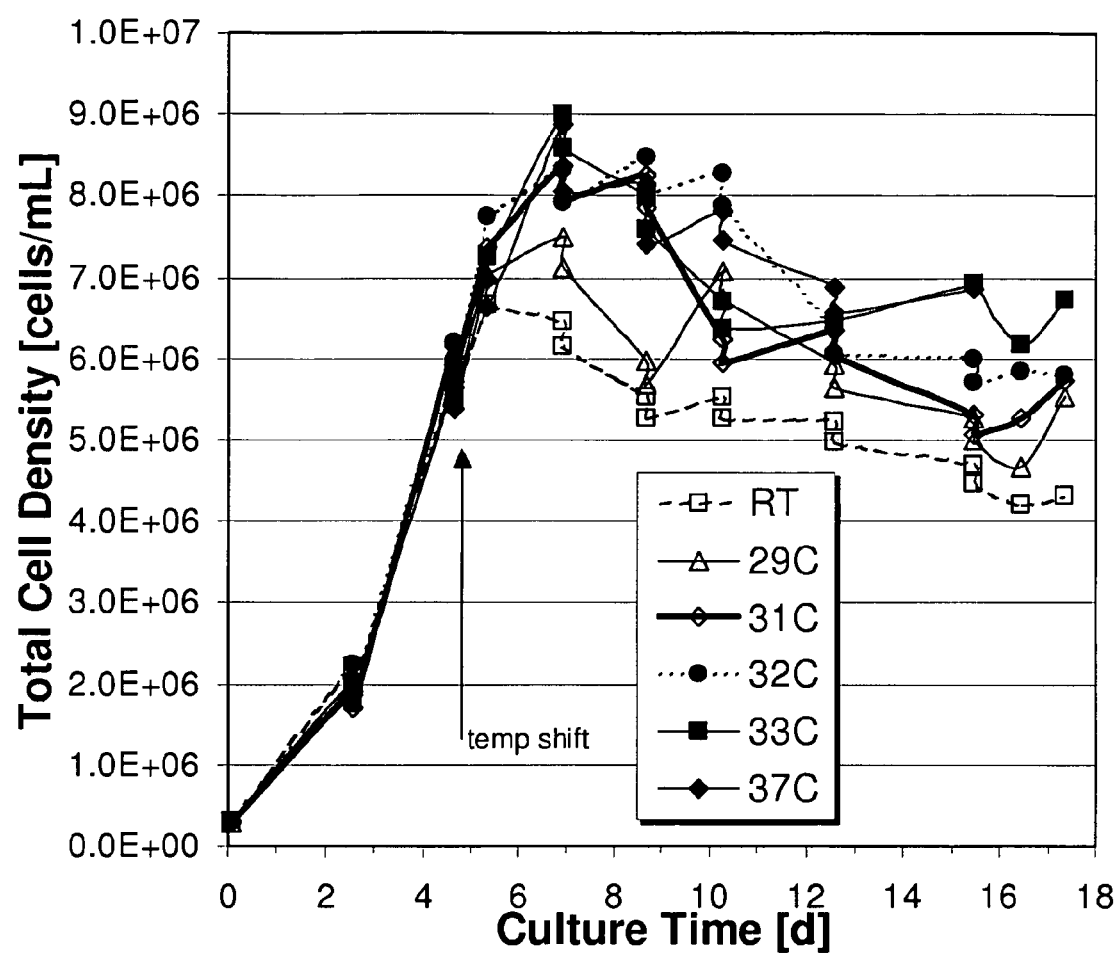
Figure 17C:
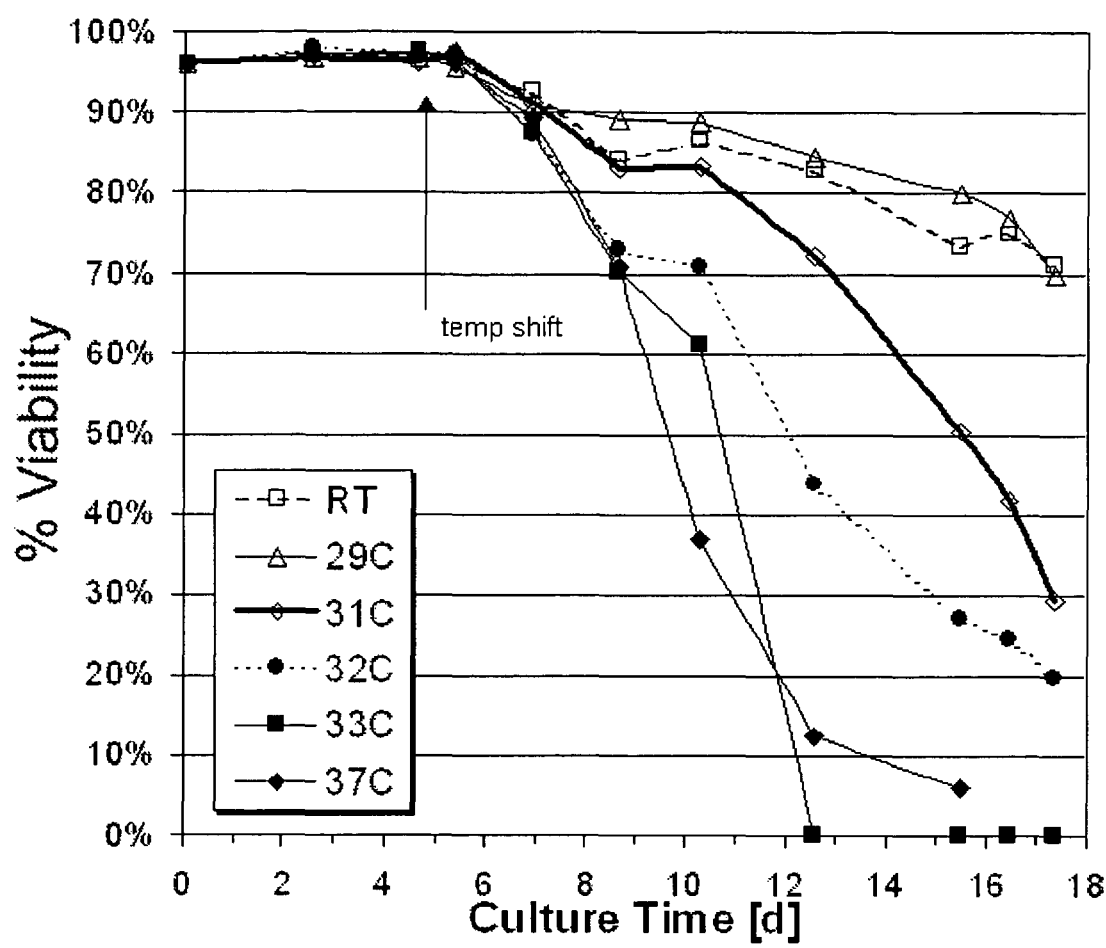
Figure 17D:
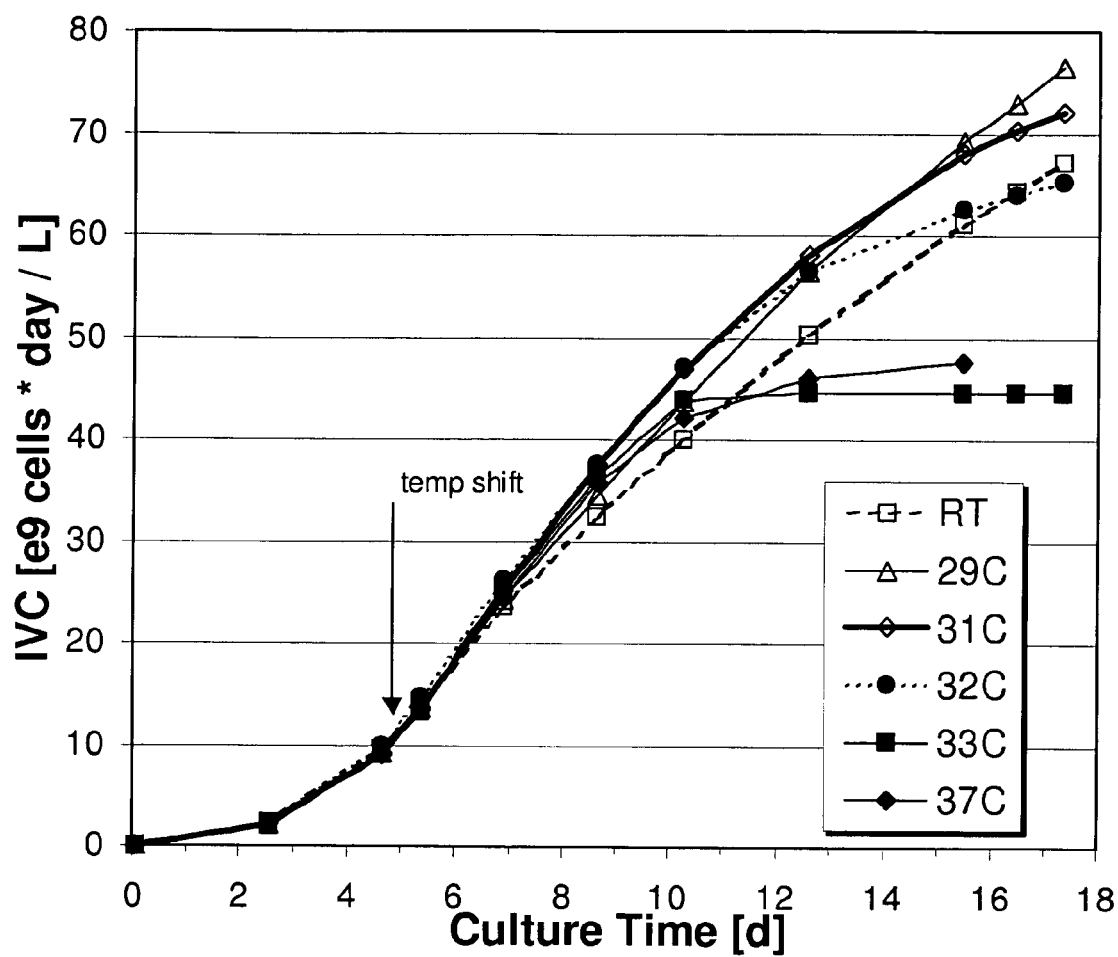

The viable cell densities achieved after the temperature shift were slightly lower at RT (about $6\times10^6$ cells/mL) and 29.0° C. (about $7\times10^6$ cells/mL) than at higher temperatures (about $8\times10^6$ cells/mL) (FIG. 17A). Similarly, the total cell densities achieved after the temperature shift were slightly lower at RT (about $6.5\times10^6$ cells/mL) and 29.0° C. (about $7.5\times10^6$ cells/mL) than at higher temperatures (about 8 to $9\times10^6$ cells/mL) (FIG. 17B). Viabilities were better maintained throughout the fed-batch at lower temperatures (FIG. 17C) The rate of decline in viability varied with the temperature; the viability profiles of the RT and 29.0° C. cultures were significantly higher than the remaining cultures at 31.0° C., 32.0° C., 33.0° C. and 37.0° C. (FIG. 17C).

At the end of the 18-day fed-batch culture, the highest titer (combined sIL-13R dimer and HMWA titer) was achieved by the 31.0° C. culture followed by the 32.0° C. culture (188 mg/L), 29.0° C. culture (178 mg/L), and 33.0° C. culture (151 mg/L) (FIG. 18). The RT and 37.0° C. cultures had significantly lower titers. The cell specific productivity, or daily specific sIL-13R production rate (Qp), of the sIL-13R-producing cell line was significantly diminished at RT and 37.0° C. (FIG. 19A). Additionally, the cumulative average specific productivities, or cumulative average Qp, were also lower at 37.0° C. and RT (FIG. 19B). Interestingly, the large increases in specific productivities seen toward the end of the 37.0° C., 33.0° C., 32.0° C., and 31.0° C. cultures corresponded with significant decreases in the culture viabilities (data not shown).

Specific glucose consumption (Qglc) declined with decreasing temperature (FIG. 20). Specific glutamine consumption (Qgln) also appeared to decline with decreasing temperature (FIG. 21). However, it should be noted that the data on specific glutamine consumption did not account for glutamine degradation in the media, which would occur to a greater extent with increasing temperature. Therefore, the impact of temperature on specific glutamine consumption may be skewed. Lactate concentration profiles for the RT, 29.0° C., 31.0° C., and 32.0° C. cultures were similar with lactate concentration peaking on or around the day of the temperature shift, then decreasing to between 0.7 and 2.0 g/L by day 18 (FIG. 22). For the 33.0° C. and 37.0° C. cultures, the lactate profiles were similar to the other cultures during the growth phase, but were significantly different during the production phase. For the 33.0° C. culture, lactate concentration did not decrease after the temperature shift, and instead remained essentially constant. For the 37.0° C. culture, lactate increased throughout the entire duration of the fed-batch.

Ammonia concentration varied during the production phase according to temperature (FIG. 23). For the 29.0° C. culture, the ammonia concentration peaked on or around the day of the temperature shift, decreased during the middle stage of the fed-batch, and then increased during the late stage of the fed-batch. With increasing temperature above 29.0° C., the increase in ammonia concentration in the late stage of the fed-batch was greater and occurred sooner. For the 37.0° C. culture, ammonia concentration increased throughout the entire course of the fed-batch. For the RT culture, the ammonia levels remained approximately constant after the temperature shift.

Samples of conditioned media from these bioreactor runs were analyzed for high molecular weight aggregates (HMWA) by size-exclusion chromatography (SEC) of batch-bound protein A eluates. A trend evident from the results of the cell line was the relative increase in the percentage of HMWA present in the conditioned medium with increasing temperature (FIG. 24 and FIG. 25). Thus, operating the cell culture at lower temperatures resulted in decreased sIL-13R product aggregation.

The decrease in percentage of sIL-13R dimer correlated with the increase in percentage of the HMWA. (FIGS. 26A and 26B). The RT culture had lower % HMWA than other cultures (FIG. 26B), as well as higher percentage of dimer formation. (FIG. 26A). The RT culture and the 31.0° C. culture yielded similar dimer only titer, while the 29.0° C. culture yielded the highest dimer only titer (FIG. 27).

In order to corroborate the conclusions from the SEC analysis, conditioned media samples were analyzed using Western blots. The qualitative differences in the amount of sIL-13R present as HMWA species versus dimer were examined. The Western blots demonstrate the trend that the amount HMWA aggregates present in the conditioned medium relative to the amount of dimer present increased with increasing temperature (data not shown).

These experiments demonstrate the importance of the interplay between the temperature-dependent variables of viability and viable cell density, specific productivity, and HMWA formation on volumetric productivity of sIL-13R dimer. Although the 31.0° C. culture achieved the highest titer (measurements included HMWA and dimer), cultures at lower temperatures (e.g., 29.0° C.) may yield comparable or improved volumetric productivity when measured in terms of dimer only.

What is claimed is:

1. A method of improving protein production in a cell culture comprising:
    (a) growing cells in the cell culture at a reduced temperature, wherein the reduced temperature is in a range of 27.0° C. to less than 30.0° C.; and
    (b) growing cells in the cell culture at a reduced pH, wherein the reduced pH is in a range of 6.80 to less than 7.00;
    wherein the cell culture is a mammalian cell culture;
    wherein the method reduces production of misfolded proteins and/or aggregated proteins; and
    wherein the protein produced is TNFR-Fc or sIL-13R.

2. The method of claim 1, wherein the cell culture is a large-scale cell culture.

3. The method of claim 1, wherein the cell culture is a fed-batch cell culture.

4. The method of claim 1, wherein the cell culture is a CHO cell culture.

5. The method of claim 1 wherein the reduced temperature is 29.5° C.

6. The method of claim 1, wherein the reduced pH is 6.95.

7. The method of claim 1, wherein the method modifies the level of protein glycosylation of the produced protein.

8. The method of claim 7, wherein the protein glycosylation is N-glycan sialylation.

9. The method of claim 1, further comprising a step of isolating the protein from the cell culture.

10. The method of claim 9, wherein the protein is further purified or processed for formulation.

11. The method of claim 10, wherein the protein is formulated into a pharmaceutical composition.

* * * * *